(12) United States Patent
Liu et al.

(10) Patent No.: US 7,994,337 B2
(45) Date of Patent: *Aug. 9, 2011

(54) BENZOTHIAZOLE AND AZABENZOTHIAZOLE COMPOUNDS USEFUL AS KINASE INHIBITORS

(75) Inventors: Chunjian Liu, Pennington, NJ (US); Katerina Leftheris, Skillman, NJ (US); James Lin, Lawrenceville, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 214 days.

This patent is subject to a terminal disclaimer.

(21) Appl. No.: 12/333,425

(22) Filed: Dec. 12, 2008

(65) Prior Publication Data

US 2009/0118272 A1    May 7, 2009

Related U.S. Application Data

(62) Division of application No. 11/494,234, filed on Jul. 27, 2006, now Pat. No. 7,473,784.

(60) Provisional application No. 60/704,351, filed on Aug. 1, 2005.

(51) Int. Cl.
  *A61K 31/428*    (2006.01)
  *C07D 417/04*    (2006.01)
(52) U.S. Cl. .................................. 548/161; 514/367
(58) Field of Classification Search .................. 548/161
  See application file for complete search history.

(56) References Cited

U.S. PATENT DOCUMENTS

| | | | |
|---|---|---|---|
| 4,200,750 | A | 4/1980 | Warner, Jr. et al. |
| 5,658,903 | A | 8/1997 | Adams et al. |
| 5,712,279 | A | 1/1998 | Biller et al. |
| 5,739,135 | A | 4/1998 | Biller et al. |
| 5,760,246 | A | 6/1998 | Biller et al. |

(Continued)

FOREIGN PATENT DOCUMENTS

| | | |
|---|---|---|
| WO | WO97/25045 | 7/1997 |
| WO | WO 00/12074 | 3/2000 |
| WO | WO 00/12497 | 3/2000 |

(Continued)

OTHER PUBLICATIONS

Das et al., "Discovery of 2-Amino-heteroaryl-benzothiazole-6-anilides as Potent p56$^{lck}$ Inhibitors", Biorganic and Medicinal Chemistry Letters, vol. 13, pp. 2587-2590, 2003.

(Continued)

*Primary Examiner* — Laura L. Stockton

(74) *Attorney, Agent, or Firm* — Laurelee A. Duncan

(57) ABSTRACT

A compound of Formula (I)

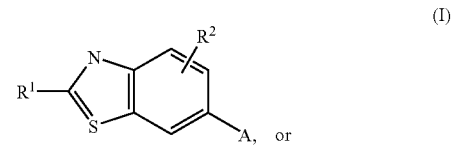

an enantiomer, diastereomer or a pharmaceutically-acceptable salt thereof, wherein A is independently selected from:

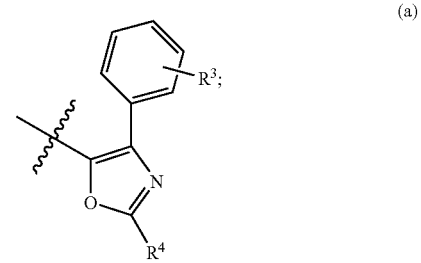

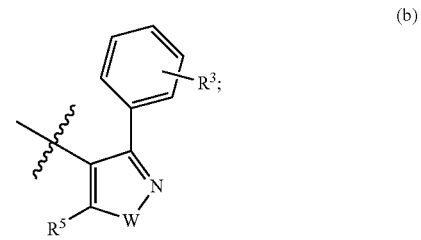

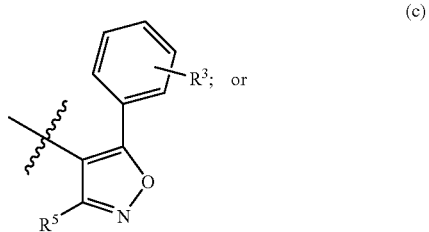

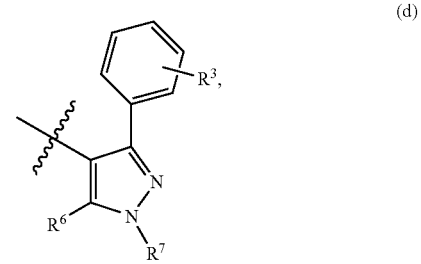

further wherein $R^1$, $R^2$, $R^3$, $R^4$, $R^5$, $R^6$, $R^7$, and W are as described herein.

13 Claims, No Drawings

U.S. PATENT DOCUMENTS

| | | | |
|---|---|---|---|
| 5,932,576 | A | 8/1999 | Anantanarayan et al. |
| 5,945,418 | A | 8/1999 | Bemis et al. |
| 5,977,103 | A | 11/1999 | Adams et al. |
| 6,087,496 | A | 7/2000 | Anantanarayan et al. |
| 6,130,235 | A | 10/2000 | Mavunkel et al. |
| 6,147,080 | A | 11/2000 | Bemis et al. |
| 6,184,231 | B1 | 2/2001 | Hewawasam et al. |
| 6,251,914 | B1 | 6/2001 | Adams et al. |
| 6,277,989 | B1 | 8/2001 | Chakravarty et al. |
| 6,548,529 | B1 | 4/2003 | Robl et al. |
| 6,706,720 | B2 | 3/2004 | Atwal et al. |
| 2004/0039033 | A1 | 2/2004 | Atwal et al. |

FOREIGN PATENT DOCUMENTS

| | | |
|---|---|---|
| WO | WO 00/56738 | 9/2000 |
| WO | WO01/01986 | 1/2001 |
| WO | WO 01/27089 | 4/2001 |
| WO | WO 01/34605 | 5/2001 |
| WO | WO2004/014900 | 2/2004 |

OTHER PUBLICATIONS

Database Accession No. 2004:150106 abstract, Chemical Abstracts Service, Columbus, Ohio, El-Sharief et al., "1,4-Phenylenediisothiocyanate in the synthesis of bis(thiourea, benzothiazole, quinazoline, 1,3-benzoxazine, and imidazolidiniminothiones) derivatives", XP00002414255 retrieved from STN, Phosphorus, Sulfur and the Related Elements, 179 (2), 267-275, 2004.

Database Accession No. 1997:255643 abstract, Chemical Abstracts Service, Columbus, Ohio, Ambat et al., "A facile synthesis of 2-(methylamino)-benzothiazoles", XP002414256 retrieved from STN, Synthetic Communications, 27 (9), 1487-1493, 1997.

Garin et al., "Synthesis of Unsymmetrical Diheteroarylbenzenes: Benzazole and Quinazoline Derivatives", Journal of Heterocyclic Chemistry, vol. 28, No. 2, 359-363, 1991.

Database Accession No. 1991:23845 abstract, Chemical Abstracts Service, Columbus, Ohio, Shirke et al., "Synthesis and antitubercular activity of some new 2-(substituted arylamino)-5,6-disubstituted/6-substituted benzothiazoles", XP002414257 retrieved from STN, Indian Drugs, 27 (6), 350-353, 1990.

Database Accession No. 1983:539834 abstract, Chemical Abstracts Service, Columbus, Ohio, Pande et al., "Synthesis of 2-arylaminobenzothiazoles and aryl isothiocyanates as antitubercular agents", XP002414258 retrieved from STN, Indian Journal of Chemistry, Section B, Organic Chemistry Including Medicinal Chemistry, 22B (3), 311-312, 1983.

Database Accession No. 1978:170021 abstract, Chemical Abstracts Service, Columbus, Ohio, Vinkler et al., "The formation of 1,3-benzothiazole derivatives from 2,2'-diaminodiphenyl disulfide. Sulfocyanation of 2,2'-diaminodiphenyl sulfide and its reaction with N-aryl isothiocyanates", XP002414259 retrieved from STN, ACTA Chimica Academiae Scientiarum Hungaricae, 94 (4), 357-361, 1977.

Ahn, S., et al., "Potent Tetracyclic Guanine Inhibitors of PDE1 and PDE5 Cyclic Guanosine Monophosphate Phosphodiesterases with Oral Antihypertensive Activity", J. Med. Chem., vol. 40, pp. 2196-2210, (1997).

Greene, T. W., "Protective Groups in Organic Synthesis", 2nd Edition, John Wiley & Sons, Inc., New York, Table of Contents, (1991).

Henry, J. R., et al., "p38 mitogen-activated protein kinase as a target for drug discovery", Drugs of the Future, vol. 24(12), pp. 1345-1354, (1999).

Moreland, L. W., et al., "Etanercept Therapy in Rheumatoid Arthritis", Ann. Intern. Med., vol. 130, pp. 478-486, (1999).

Raingeaud, J., et al., "MKK3- and MKK6-Regulated Gene Expression is Mediated by the p38 Mitogen-Activated Protein Kinase Signal Transduction Pathway", Molecular and Cellular Biology, vol. 16(3), pp. 1247-1255, (1996).

Rankin, E. C. C., et al., "The Therapeutic Effects of an Engineered human Anti-Tumour Necrosis Factor Alpha Antibody (CDP571) in Rheumatoid Arthritis", British Journal of Rheumatology, vol. 34, pp. 334-342, (1995).

Salituro, F. G., et al., "Inhibitors of p38 MAP Kinase: Therapeutic Intervention in Cytokine-Mediated Diseases", Current Medicinal Chemistry, vol. 6, pp. 807-823, (1999).

BENZOTHIAZOLE AND AZABENZOTHIAZOLE COMPOUNDS USEFUL AS KINASE INHIBITORS

RELATED APPLICATION

This application is a divisional application of U.S. application Ser. No. 11/494,234, filed Jul, 27, 2006, now issued as U.S. Pat. No. 7,473,784, which claims the benefit of priority benefit of United States Provisional Application No. 60/704, 351, filed Aug. 1, 2005, the contents of which are herein incorporated by reference.

FIELD OF THE INVENTION

This invention relates to benzothiazole and azabenzothiazole compounds, more particularly, to benzothiazole and aza-benzothiazole compounds useful for treating kinase-associated conditions, such as p38 kinase-associated conditions. The invention further pertains to pharmaceutical compositions containing at least one compound according to the invention useful for treating kinase-associated conditions, such as p38 kinase-associated conditions, and methods of inhibiting the activity of kinase in a mammal.

BACKGROUND OF THE INVENTION

A large number of cytokines participate in the inflammatory response, including IL-1, IL-6, IL-8 and TNF-α. Overproduction of cytokines such as IL-1 and TNF-α are implicated in a wide variety of diseases, including inflammatory bowel disease, rheumatoid arthritis, psoriasis, multiple sclerosis, endotoxin shock, osteoporosis, Alzheimer's disease, and congestive heart failure, among others [Henry et al., Drugs Fut., 24:1345-1354 (1999); Salituro et al., Curr. Med. Chem., 6:807-823 (1999)]. Evidence in human patients indicates that protein antagonists of cytokines are effective in treating chronic inflammatory diseases, such as, for example, monoclonal antibody to TNF-α (Enbrel) [Rankin et al., Br. J. Rheumatol., 34:334-342 (1995)], and soluble TNF-α receptor-Fc fusion protein (Etanercept) [Moreland et al., Ann. Intern. Med., 130:478-486 (1999)].

The biosynthesis of TNF-α occurs in many cell types in response to an external stimulus, such as, for example, a mitogen, an infectious organism, or trauma. Important mediators of TNF-α production are the mitogen-activated protein (MAP) kinases, and in particular, p38 kinase. These kinases are activated in response to various stress stimuli, including, but not limited to, proinflammatory cytokines, endotoxin, ultraviolet light, and osmotic shock.

One important MAP kinase is p38 kinase, also known as cytokine suppressive anti-inflammatory drug binding protein (CSBP) or IK. Activation of p38 requires dual phosphorylation by upstream MAP kinase kinases (MKK3 and MKK6) on threonine and tyrosine within a Thr-Gly-Tyr motif characteristic of p38 isozymes. There are four known isoforms of p38, i.e., p38α, p38β, p38γ, and p38δ. The α and β isoforms are expressed in inflammatory cells and are key mediators of TNF-α production. Inhibiting the p38α and β enzymes in cells results in reduced levels of TNF-α expression. Also, administering p38α and β inhibitors in animal models of inflammatory disease has proven that such inhibitors are effective in treating those diseases. Accordingly, the p38 enzymes serve an important role in inflammatory processes mediated by IL-1 and TNF-α.

Compounds that reportedly inhibit p38 kinase and cytokines, such as IL-1 and TNF-α for use in treating inflammatory diseases, are disclosed in U.S. Pat. Nos. 6,277,989 and 6,130, 235 to Scios, Inc; U.S. Pat. Nos. 6,147,080 and 5,945,418 to Vertex Pharmaceuticals Inc; U.S. Pat. Nos. 6,251,914, 5,977, 103 and 5,658,903 to Smith-Kline Beecham Corp.; U.S. Pat. Nos. 5,932,576 and 6,087,496 to G.D. Searle & Co.; WO 00/56738 and WO 01/27089 to Astra Zeneca; WO 01/34605 to Johnson & Johnson; WO 00/12497 (quinazoline derivatives as p38 kinase inhibitors); WO 00/56738 (pyridine and pyrimidine derivatives for the same purpose); WO 00/12497 (discusses the relationship between p38 kinase inhibitors); and WO 00/12074 (piperazine and piperidine compounds useful as p38 inhibitors).

The present invention provides certain benzothiazole and aza-benzothiazole compounds useful as kinase inhibitors, particularly kinases p38α and β. Each of the patent applications, patents, and publications referred to herein is incorporated herein by reference.

SUMMARY OF THE INVENTION

The instant invention generally pertains to compounds of Formula (I),

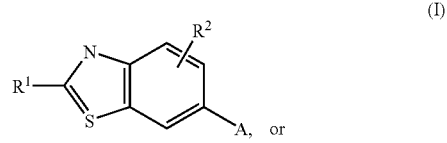

an enantiomer, diastereomer or a pharmaceutically-acceptable salt thereof, wherein:

$R^1$ is hydrogen, hydroxyl, halo, amino, substituted amino, alkyl, substituted alkyl, cycloalkyl, aryl or heterocyclo;

$R^2$ is hydrogen, halo, cyano, $C_1$-$C_4$ alkyl or $C_3$-$C_6$ cycloalkyl; and A is independently selected from:

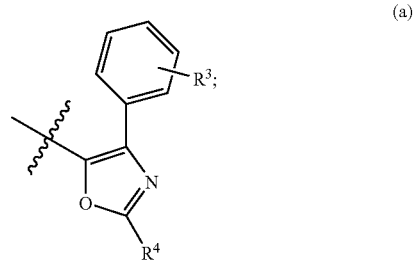

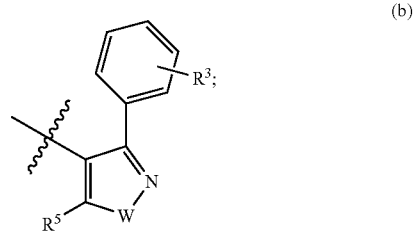

3
-continued (c)

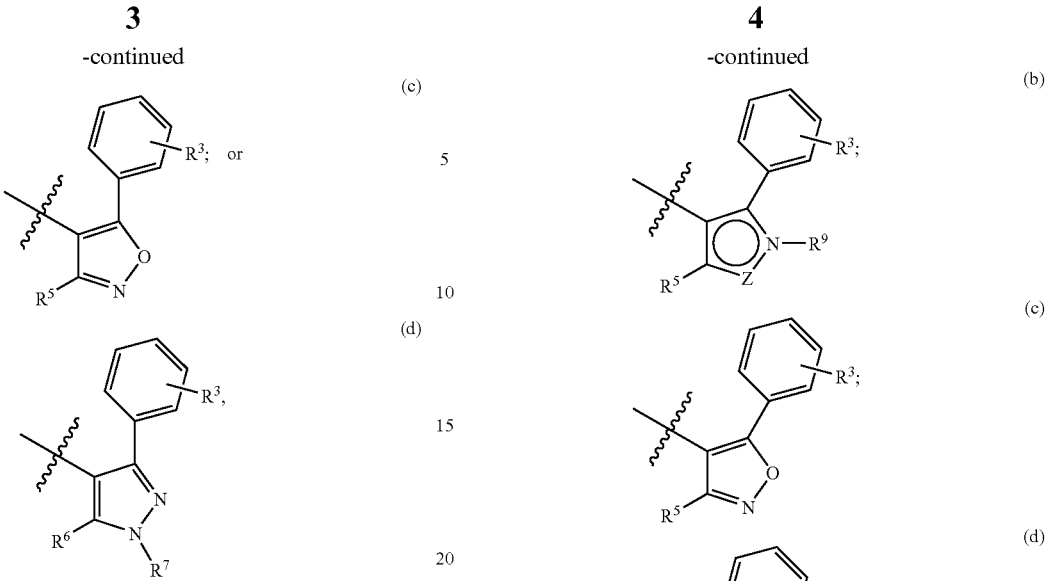

(d)

wherein
R³, R⁴, R⁵, R⁶, R⁷ and W are as defined hereinbelow.

The invention further pertains to pharmaceutical compositions containing compounds of Formula (I), and to methods of treating conditions associated with the activity of kinase, such as p38 (α and β), comprising administering to a mammal a pharmaceutically-acceptable amount of a compound of Formula (I).

The instant invention also relates to compounds of Formula (II), (II)

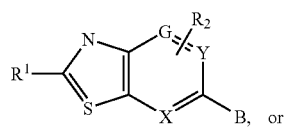

an enantiomer, diastereomer, or a pharmaceutically-acceptable salt thereof, wherein:

$R^1$ is hydrogen, halo, amino, substituted amino, alkyl, substituted alkyl, cycloalkyl, aryl or heterocyclo;

$R^2$ is hydrogen, halo, cyano, $C_1$-$C_4$ alkyl or $C_3$-$C_6$ cycloalkyl;

each of G, X and Y is independently CH or N, wherein at each occurrence at least one of G, X or Y is N and the other two of G, X or Y are CH; and B is independently selected from:

(a)

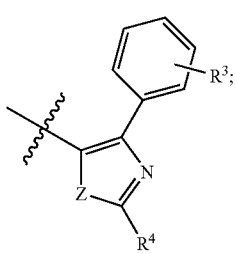

4
-continued (b)

(c)

(d)

(e)

wherein
R³, R⁴, R⁵, R⁸, R⁹ and Z are as defined hereinbelow.

The invention further pertains to pharmaceutical compositions containing compounds of Formula (II), and to methods of treating conditions associated with the activity of kinase, such as p38 (α and β), comprising administering to a mammal a pharmaceutically-acceptable amount of a compound of Formula (II).

DETAILED DESCRIPTION OF THE INVENTION

Listed below are definitions of various terms used to describe this invention. These definitions apply to the terms as they are used throughout this specification, unless otherwise limited in specific instances, either individually or as part of a larger group.

The terms "alkyl" and "alk" refers to a straight or branched chain alkane (hydrocarbon) radical containing from 1 to 12 carbon atoms, preferably 1 to 6 carbon atoms. Exemplary groups include, but are not limited to, methyl, ethyl, propyl, isopropyl, n-butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, and the like.

"Substituted alkyl" refers to an alkyl group substituted with one or more substituents, preferably 1 to 4 substituents, at any available point of attachment on the alkyl straight or branched chain. Exemplary substituents include one or more of the following groups: halo (e.g., a single halo substituent or multiple halo substituents forming, in the latter case, groups such as a perfluoroalkyl group or an alkyl group bearing $Cl_3$ or $CF_3$), nitro, cyano, hydroxy, alkoxy, haloalkoxy (e.g., trifluoromethoxy), —O-aryl, —O-heterocyclo, —O-alkylene-aryl, —O-haloalkyl, alkylthio, carboxy (i.e., —COOH), alkoxycarbonyl, alkylcarbonyloxy, carbamoyl, substituted carbamoyl, carbamate, substituted carbamate, urea, substituted urea, amidinyl, substituted amindinyl, aryl, heterocycle, cycloalkyl, —$NR^cR^d$, —$OC(=O)NR^cR^d$, —$C(=O)NR^cR^d$, —$NR^eC(=O)NR^cR^d$, —$NR^eC(O)—NR^cR^d$, —$N(R^e)S(O)_2NR^cR^d$, —$N(R^e)P(O)_2NR^cR^d$, (wherein each of $R^c$ and $R^d$ is independently selected from hydrogen, alkyl, aryl, and heterocyclo, and $R^e$ is hydrogen, alkyl, or phenyl); and —$SR^f$, —$S(=O)R^g$, —$S(O)_2R^g$, —$NR^eS(O)_2—R^g$, —$P(O)_2—R^g$, —$NR^eP(O)_2—R^g$, —$NR^eC(=O)R^f$, —$NR^eC(O)_2R^f$, —$OC(=O)R^f$, —$OC(=O)OR^f$, —$C(=O)OR^f$ or —$C(=O)R^f$ (wherein $R^e$ is defined as immediately above, $R^f$ is hydrogen, alkyl, aryl or heterocyclo, and $R^g$ is alkyl, aryl, or heterocyclo). In the aforementioned substituents, in each instance, the alkyl, aryl, heterocyclo or cycloalkyl groups ($R^e$, $R^d$, $R^e$, $R^f$, and $R^g$) in turn can be optionally substituted with one to four, preferably one to three further groups, selected from $R^k$, —O—$R^k$, cyano, nitro, haloalkyl, haloalkoxy, halo, —$NR^kR^m$, —$OC(=O)NR^kR^m$, —$C(=O)NR^kR^m$, —$NR^kC(=O)R^m$, —$SR^k$, —$S(=O)R^n$, —$S(O)_2R^n$, —$OC(=O)R^k$, —$C(=O)OR^k$, —$C(=O)R^k$, phenyl, benzyl, phenyloxy, or benzyloxy, or a lower alkyl substituted with one to two of —O—$R^k$, cyano, nitro, haloalkyl, haloalkoxy, halo, —$NR^kR^m$, —$OC(=O)NR^kR^m$, —$C(=O)NR^kR^m$, —$NR^kC(=O)R^m$, —$SR^k$, —$S(=O)R^n$, —$S(O)_2R^n$, —$OC(=O)R^k$, —$C(=O)OR^k$, —$C(=O)R^k$, phenyl, benzyl, phenyloxy, or benzyloxy, wherein $R^k$ and $R^m$ are selected from hydrogen, lower alkyl, hydroxy(lower alkyl), halo(lower alkyl), cyano (lower alkyl), and amino(lower alkyl), and $R^n$ is lower alkyl.

As used herein, "alkylene" refers to a bivalent alkyl radical having the general formula —$(CH_2)_n$—, where n is 1 to 10. Non-limiting examples include methylene, dimethylene, trimethylene, tetramethylene, pentamethylene, and hexamethylene. The term "lower alkylene" herein refers to those alkylene groups having from about 1 to about 6 carbon atoms. "Substituted alkylene" refers to an alkylene group substituted with one or more substituents, preferably 1 to 4 substituents, at any available point of attachment. Exemplary substituents include, but are not limited to, alkyl, substituted alkyl, and those groups recited above as exemplary alkyl substituents.

When the term alkyl is used as a subscript following another particularly-named group, as in "arylalkyl," "substituted arylalkyl," "cycloalkylalkyl," etc., or as in hydroxy (lower alkyl), this refers to an alkyl group having one or two (preferably one) substituents selected from the other, particularly-named group. Thus, for example, arylalkyl includes benzyl, biphenyl and phenylethyl. A "substituted arylalkyl" will be substituted on the alkyl portion of the radical with one or more groups selected from those recited above for alkyl, and/or will be substituted on the aryl portion of the radical with one or more groups selected from those recited below for substituted aryl.

The term "alkenyl" refers to a straight or branched chain hydrocarbon radical containing from 2 to 12 carbon atoms and at least one carbon-carbon double bond. Exemplary groups include ethenyl or allyl. "Substituted alkenyl" refers to an alkenyl group substituted with one or more substituents, preferably 1 to 4 substituents, at any available point of attachment. Exemplary substituents include, but are not limited to, alkyl, substituted alkyl, and those groups recited above as exemplary alkyl substituents.

The term "alkenylene" refers to a straight or branched chain bivalent hydrocarbon radical containing from 2 to 12 carbon atoms and at least one carbon-carbon double bond. Exemplary groups include ethenylene or allylene. "Substituted alkenylene" refers to an alkenylene group substituted with one or more substituents, preferably 1 to 4 substituents, at any available point of attachment. Exemplary substituents include, but are not limited to, alkyl, substituted alkyl, and those groups recited above as exemplary alkyl substituents.

The term "alkynyl" refers to a straight or branched chain hydrocarbon radical containing from 2 to 12 carbon atoms and at least one carbon to carbon triple bond. Exemplary groups include ethynyl. "Substituted alkynyl" refers to an alkynyl group substituted with one or more substituents, preferably 1 to 4 substituents, at any available point of attachment. Exemplary substituents include, but are not limited to, alkyl, substituted alkyl, and those groups recited above as exemplary alkyl substituents.

The term "alkynylene" refers to a straight or branched chain bivalent hydrocarbon radical containing from 2 to 12 carbon atoms and at least one carbon to carbon triple bond. Exemplary groups include ethynylene. "Substituted alkynylene" refers to an alkynylene group substituted with one or more substituents, preferably 1 to 4 substituents, at any available point of attachment. Exemplary substituents include, but are not limited to, alkyl, substituted alkyl, and those groups recited above as exemplary alkyl substituents.

The term "cycloalkyl" refers to a fully saturated cyclic hydrocarbon group containing from 1 to 3 rings and 3 to 8 carbons per ring. Exemplary groups include cyclopropyl, cyclobutyl, cyclopentyl, and cyclohexyl. The term "cycloalkyl" also includes groups having a carbon-carbon bridge of one to two bridgehead carbon atoms, and bicyclic and tricyclic groups in which at least one of the rings is a saturated, carbon-containing ring, in which case the second or third ring may be carbocyclic or heterocyclic, provided that the point of attachment is to the cycloalkyl group. The further rings may be attached to the saturated, carbon-containing ring in a spiro or fused fashion. "Substituted cycloalkyl" refers to a cycloalkyl group substituted with one or more substituents, preferably 1 to 4 substituents, at any available point of attachment. Exemplary substituents include, but are not limited to, alkyl, substituted alkyl, oxo(=O), and those groups recited above as exemplary alkyl substituents.

The term "cycloalkylene" refers to a bivalent cycloalkyl group as defined above. Exemplary groups include cyclopropylene, cyclobutylene, cyclopentylene and cyclohexylene. "Substituted cycloalkylene" refers to a cycloalkylene group substituted with one or more substituents, preferably 1 to 4 substituents, at any available point of attachment selected from those recited for substituted cycloalkyl.

The term "cycloalkenyl" refers to a partially unsaturated cyclic hydrocarbon group containing 1 to 3 rings and 4 to 8 carbons per ring. Exemplary groups include cyclobutenyl, cyclopentenyl, and cyclohexenyl. The term "cycloalkenyl" also includes bicyclic and tricyclic groups in which at least one of the rings is a partially unsaturated, carbon-containing ring and the second or third ring may be carbocyclic or heterocyclic, provided that the point of attachment is to the cycloalkenyl group. "Substituted cycloalkenyl" refers to a cycloalkenyl group substituted with one or more substituents, preferably 1 to 4 substituents, at any available point of attachment selected from those recited above for cycloalkyl groups.

The term "cycloalkenylene" refers to a bivalent cycloalkenyl group, as defined above. Exemplary groups include cyclobutenylene, cyclopentenylene, and cyclohexenylene. "Substituted cycloalkenylene" refers to a cycloalkenylene group substituted with one or more substituents, preferably 1 to 4 substituents, at any available point of attachment, selected from those recited for substituted cycloalkyl. The terms "alkoxy" or "alkylthio" refer to an alkyl group as described above bonded through an oxygen linkage (—O—) or a sulfur linkage (—S—), respectively. The terms "substituted alkoxy" or "substituted alkylthio" refer to a substituted alkyl group as described above bonded through an oxygen or sulfur linkage, respectively. "Thiol" refers to —SH.

The term "alkoxycarbonyl" refers to an alkoxy group bonded through a carbonyl group (i.e., —C(=O)—O-alkyl). The term "alkylcarbonyl" refers to an alkyl group bonded through a carbonyl group (i.e., —C(=O)alkyl).

The term "alkylcarbonyloxy" refers to an alkylcarbonyl group bonded through an oxygen linkage (i.e., —O—C(=O)-alkyl).

The term "amido" refers to the group —NHC(=O)H, and amidinyl refers to the group —C(=NH)(NH$_2$). A "substituted amido" refers to the group —NR$^p$C(=O)R$^q$, and a "substituted amidinyl" refers to the group —C(=NR$^p$)(NR$^q$R$^r$), wherein R$^p$, R$^q$, and R$^r$ are selected from hydrogen, alkyl, substituted alkyl, cycloalkyl, substituted cycloalkyl, aryl, substituted aryl, heterocyclo, and substituted heterocyclo, provided that at least one of R$^p$, R$^q$, and R$^r$ is other than hydrogen.

The term "aryl" encompasses monocyclic and polycyclic aryl groups. The term "monocyclic aryl" refers to phenyl, and the term "polycyclic aryl" refers to napthyl and anthracenyl, to phenyl rings having at least a second ring fused thereto, and to napthyl rings having a third ring fused thereto. In the case of a polycyclic aryl consisting of a phenyl ring having a second or third ring fused thereto, or a napthyl ring having a third ring fused thereto, the additional rings may be aromatic or non-aromatic carbocyclic or heterocyclic rings, provided that in such cases the point of attachment will be to the carbocyclic aromatic ring. Additionally, a ring carbon atom of the second and third further rings may be replaced with a carbonyl [—C(=O)group] (e.g., when such rings are non-aromatic). "Substituted aryl" refers to an aryl group substituted by one or more substituents, preferably 1 to 4 substituents (more preferably 1 or 2), at any point of attachment of any ring, selected from alkyl, substituted alkyl, and the substituents recited above for substituted alkyl groups.

Accordingly, examples of aryl groups include:

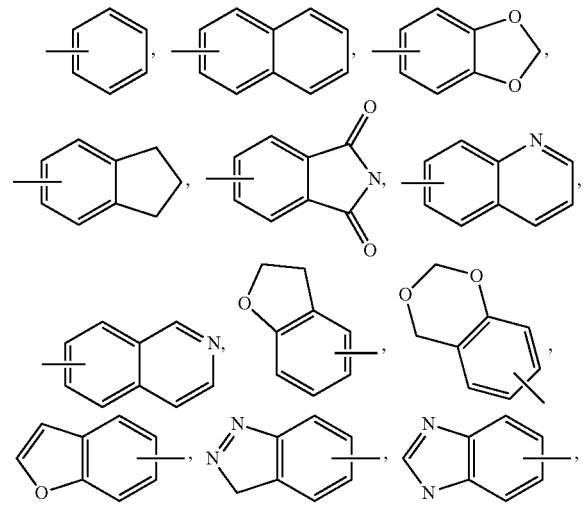

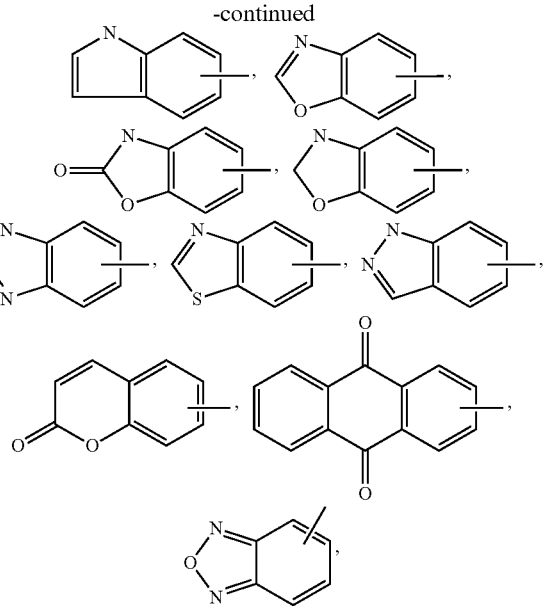

and the like.

The term "arylene" refers to bivalent aryl groups as defined above.

"Carbamoyl" refers to the group —C(=O)—NR$^h$R$^i$, wherein R$^h$ and R$^i$ are selected from hydrogen, alkyl, cycloalkyl, aryl, and heterocyclo.

"Carbamate" refers to the group —O—C(=O)—NR$^h$R$^i$, and "urea" refers to the groups NH—C(=O)—NR$^h$R$^i$ and N(alkyl)-C(=O)—NR$^h$R$^i$, wherein R$^h$ and R$^i$ are selected from the same groups recited for carbamoyl.

"Substituted carbamoyl," "substituted carbamate," and "substituted urea" refer to the groups —C(=O)—NR$^h$R$^i$, —O—C(=O)—NR$^h$R$^i$, and —N(R$^j$)—C(=O)—NR$^h$R$^i$, respectively, wherein R$^h$, R$^i$, and R$^j$ are selected from hydrogen, alkyl, substituted alkyl, cycloalkyl, substituted cycloalkyl, aryl, substituted aryl, heterocyclo, and substituted heterocyclo, provided that at least one of R$^h$, R$^i$, and R$^j$ is substituted alkyl, substituted cycloalkyl, substituted aryl, or substituted heterocyclo.

The terms "heterocycle", "heterocyclic" and "heterocyclo" refer to fully saturated, partially unsaturated, or fully unsaturated, including aromatic (i.e., "heteroaryl") cyclic groups (for example, 3 to 7 membered monocyclic, 7 to 11 membered bicyclic, or 10 to 16 membered tricyclic ring systems) which have at least one heteroatom in at least one carbon atom-containing ring. Thus, the term "heteroaryl" is a subset of heterocyclo groups. Each ring of the heterocyclic group containing a heteroatom may have 1, 2, 3, or 4 heteroatoms selected from nitrogen atoms, oxygen atoms and/or sulfur atoms, where the nitrogen and sulfur heteroatoms may optionally be oxidized and the nitrogen heteroatoms may optionally be quaternized. (The term "heteroarylium" refers to a heteroaryl group bearing a quaternary nitrogen atom and thus a positive charge.) Additionally, one or more (preferably one) carbon ring atoms of the heterocyclo ring may, as valence allows, be replaced with carbonyl group, i.e., —C(=O)—. The heterocyclic group may be attached to the remainder of the molecule at any heteroatom or carbon atom of the ring or ring system.

Exemplary monocyclic heterocyclic groups include ethylene oxide, azetidinyl, pyrrolidinyl, pyrrolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolodinyl, 2-oxoazepinyl, azepinyl, hexahydrodiazepinyl, 4-piperidonyl, pyridyl, pyrazinyl, pyrimidinyl, pyridazinyl, triazinyl, triazolyl, tetrazolyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl, and the like.

Exemplary bicyclic heterocyclic groups include indolyl, isoindolyl, benzothiazolyl, benzodioxolyl, benzoxazolyl, benzoxadiazolyl, benzothienyl, quinuclidinyl, quinolinyl, tetrahydroisoquinolinyl, isoquinolinyl, benzimidazolyl, benzopyranyl, indolizinyl, benzofuryl, benzofurazanyl, chromonyl, coumarinyl, benzopyranyl, cinnolinyl, quinoxalinyl, indazolyl, pyrrolopyridyl, furopyridinyl (such as furo[2,3-c]pyridinyl, furo[3,2-b]pyridinyl] or furo[2,3-b]pyridinyl), dihydrobenzodioxinyl, dihydrodioxidobenzothiophenyl, dihydroisoindolyl, dihydroindolyl, dihydroquinolinyl, dihydroquinazolinyl (such as 3,4-dihydro-4-oxo-quinazolinyl), triazinylazepinyl, tetrahydroquinolinyl and the like. Exemplary tricyclic heterocyclic groups include carbazolyl, benzidolyl, phenanthrolinyl, dibenzofuranyl, acridinyl, phenanthridinyl, xanthenyl and the like.

The term "heterocyclene" refers to bivalent heterocycle groups as defined above.

"Substituted heterocycle," "substituted heterocyclic," and "substituted heterocyclo" (such as "substituted heteroaryl") refer to heterocycle, heterocyclic or heterocyclo groups substituted with one or more substituents, preferably 1 to 4 substituents, at any available point of attachment, wherein the substituents are selected from those recited above for substituted cycloalkyl groups.

The term "quaternary nitrogen" refers to a tetravalent positively charged nitrogen atom including, for example, the positively charged nitrogen in a tetraalkylammonium group (e.g., tetramethylammonium, N-methylpyridinium), the positively charged nitrogen in protonated ammonium species (e.g., trimethyl-hydroammonium, N-hydropyridinium), the positively charged nitrogen in amine N-oxides (e.g., N-methylmorpholine-N-oxide, pyridine-N-oxide), and the positively charged nitrogen in an N-amino-ammonium group (e.g., N-aminopyridinium).

The term "heteroaryl" refers to five and six membered monocyclic aromatic heterocyclo groups, as well as bicyclic and tricyclic heterocyclic ring systems in which the point of attachment of the ring system to another group is via a five or six membered aromatic ring of the ring system. Thus, for example, the term heteroaryl includes groups such as five or six membered heteroaryl groups, such as thienyl, pyrrolyl, oxazolyl, pyridyl, pyrazinyl, and the like, wherein fused rings completing bicyclic and tricyclic groups may contain only carbon atoms and may be saturated, partially saturated, or unsaturated. Heteroaryl groups which are bicyclic or tricyclic must include at least one fully aromatic ring but the other fused ring or rings may be aromatic or non-aromatic. The term "substituted heteroaryl" refers to five and six membered monocyclic aromatic heterocyclo groups substituted with one or more substituents, preferably 1 to 4 substituents, at any available point of attachment, wherein the substituents are selected from those recited above for substituted cycloalkyl groups.

Exemplary monocyclic heteroaryl groups include pyrrolyl, pyrazolyl, imidazolyl, oxazolyl, isoxazolyl, thiazolyl, thiadiazolyl, isothiazolyl, furanyl, thienyl, oxadiazolyl, pyridyl, pyrazinyl, pyrimidinyl, and the like.

Exemplary bicyclic heteroaryl groups include indolyl, benzothiazolyl, benzodioxolyl, benzoxaxolyl, benzothienyl, quinolinyl, isoquinolinyl, benzimidazolyl, benzopyranyl, indolizinyl, benzofuranyl, chromonyl, coumarinyl, benzopyranyl, cinnolinyl, quinoxalinyl, indazolyl, pyrrolopyridyl, furopyridinyl, and the like.

Exemplary tricyclic heteroaryl groups include carbazolyl, benzidolyl, phenanthrollinyl, acridinyl, phenanthridinyl, xanthenyl and the like.

The terms "halogen" or "halo" refer to chlorine, bromine, fluorine or iodine.

The terms "hydroxylamine" and "hydroxylamide" refer to the groups —NH—OH and —C(=O)—NH—OH, respectively.

Unless otherwise indicated, the term "substituted amino" as employed herein alone or as part of another group refers to amino substituted with one or two substituents, which may be the same or different, such as alkyl, aryl, arylalkyl, heterocyclo, heteroaryl, heteroarylalkyl, cycloheteroalkyl, cycloheteroalkylalkyl, cycloalkyl, cycloalkylalkyl, haloalkyl, hydroxyalkyl, alkoxyalkyl, thioalkyl, —C(O)R$^f$, —C(=O)OR$^f$, —C(=O)NR$^f$R$^g$, —S(O)$_2$R$^f$, —S(O)$_2$OR$^f$, or —S(O)$_2$NR$^f$R$^g$, wherein R$^f$ and R$^g$ can be hydrogen, alkyl, substituted alkyl, aryl, substituted aryl or heterocyclo. These substituents may be further substituted with a carboxylic acid and/or any of the substituents for alkyl as set out above. In addition, the amino substituents may be taken together with the nitrogen atom to which they are attached to form 1-pyrrolidinyl, 1-piperidinyl, 1-azepinyl, 4-morpholinyl, 4-thiamorpholinyl, 1-piperazinyl, 4-alkyl-1-piperazinyl, 4-arylalkyl-1-piperazinyl, 4-diarylalkyl-1-piperazinyl, 1-pyrrolidinyl, 1-piperidinyl, or 1-azepinyl, optionally substituted with alkyl, aryl, heterocyclo, alkoxy, alkylthio, halo, trifluoromethyl, hydroxy, amino, —C(O)R$^f$, —C(=O)OR$^f$, —C(=O)NR$^f$R$^g$, —S(O)$_2$R$^f$, —S(O)$_2$OR$^f$, or —S(O)$_2$NR$^f$R$^g$, wherein R$^f$ and R$^g$ can be hydrogen, alkyl, substituted alkyl, aryl, substituted aryl or heterocyclo.

The term "heteroatoms" shall include oxygen, sulfur and nitrogen.

The term "haloalkyl" means an alkyl having one or more halo substituents.

The term "haloalkoxy" means an alkoxy group having one or more halo substituents. For example, "haloalkoxy" includes —OCF$_3$.

The term "carbocyclic" means a saturated or unsaturated monocyclic or bicyclic ring in which all atoms of all rings are carbon. Thus, the term includes cycloalkyl and aryl rings. The carbocyclic ring may be substituted, in which case the substituents are selected from those recited above for cycloalkyl and aryl groups.

When the term "unsaturated" is used herein to refer to a ring or group, the ring or group may be fully unsaturated or partially unsaturated.

When it is stated that a group may be "optionally substituted," this is intended to include unsubstituted groups and substituted groups wherein the substituents are selected from those recited above for the particularly named group. Thus, when reference is made to an optionally substituted aryl, it is intended to refer to unsubstituted aryl groups, such as phenyl or naphthyl, and such groups having one or more (preferably 1 to 4, and more preferably 1 or 2) substituents selected from alkyl, substituted alkyl, and those substituents recited for substituted alkyl groups. When the term "optionally substituted" precedes a Markush group, the term "optionally substituted" is intended to modify each one of the species recited in the Markush group. Thus, for example, the phrase "optionally substituted aryl, cycloalkyl, or heterocycle" includes aryl, substituted aryl, cycloalkyl, substituted cycloalkyl, heterocycle, and substituted heterocycle.

Among the compounds of the invention, in the case of a compound which has a sulfide, the sulfur atom may be converted into oxido at an appropriate oxidation state, and all of these oxido derivatives are included herein.

"N-oxide" refers to compounds wherein the basic nitrogen atom of either a heteroaromatic ring or tertiary amine is oxidized to give a quaternary nitrogen bearing a positive formal charge and an attached oxygen atom bearing a negative formal charge.

When a functional group is termed "protected", this means that the group is in modified form to mitigate, especially preclude, undesired side reactions at the protected site. Suitable protecting groups for the methods and compounds described herein include, without limitation, those described in standard textbooks, such as Greene, T. W. et al., *Protective Groups in Organic Synthesis*, Wiley, N.Y. (1991).

Unless otherwise indicated, any heteroatom with unsatisfied valences is assumed to have hydrogen atoms sufficient to satisfy the valences.

Carboxylate anion refers to a negatively charged group —COO⁻.

The compounds of the present invention may form salts which are also within the scope of this invention. Pharmaceutically acceptable (i.e., non-toxic, physiologically acceptable) salts are preferred, although other salts are also useful, e.g., in isolating or purifying the compounds of this invention.

The compounds of the present invention may form salts with alkali metals such as sodium, potassium, and lithium; with alkaline earth metals such as calcium and magnesium; and with organic bases such as dicyclohexylamine, tributylamine, pyridine, and amino acids such as arginine, lysine, and the like. Such salts can be formed as known to those skilled in the art.

The compounds of the present invention may form salts with a variety of organic and inorganic acids. Such salts include those formed with hydrogen chloride, hydrogen bromide, methanesulfonic acid, sulfuric acid, acetic acid, trifluoroacetic acid, oxalic acid, maleic acid, benzenesulfonic acid, toluenesulfonic acid, and various others (e.g., nitrates, phosphates, borates, tartrates, citrates, succinates, benzoates, ascorbates, salicylates, and the like). Such salts can be formed as known to those skilled in the art. Salt forms of the compounds may be advantageous for improving the compound dissolution rate and oral bioavailability.

In addition, zwitterions ("inner salts") may be formed.

All stereoisomers of the compounds of the instant invention are contemplated, either in admixture or in pure or substantially pure form. The definition of compounds according to the invention embraces all the possible stereoisomers and their mixtures; it also embraces the racemic forms and the isolated optical isomers having the specified activity. The racemic forms can be resolved by physical methods, such as, for example, fractional crystallization, separation, or crystallization of diastereomeric derivatives or separation by chiral column chromatography. The individual optical isomers can be obtained from the racemates from the conventional methods, such as, for example, salt formation with an optically active acid followed by crystallization.

Preferred Compounds

One embodiment of the present invention relates to a compound of Formula (I)

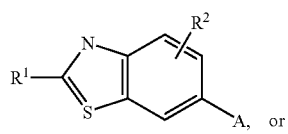

(I)

an enantiomer, diastereomer or a pharmaceutically-acceptable salt thereof, wherein substituent A is independently selected from:

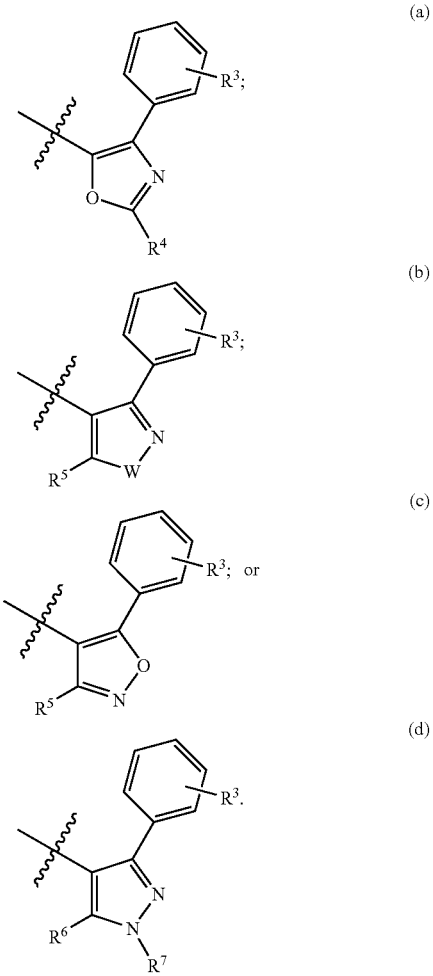

In this embodiment, $R^1$ is hydrogen, hydroxyl, halo, amino, substituted amino, alkyl, substituted alkyl, cycloalkyl, aryl or heterocyclo; $R^2$ is hydrogen, halo, cyano, $C_1$-$C_4$ alkyl or $C_3$-$C_6$ cycloalkyl; $R^3$ is hydrogen, halo, cyano, optionally substituted $C_1$-$C_4$ alkyl, optionally substituted $C_3$-$C_6$ cycloalkyl, amino or substituted amino; $R^4$ is hydrogen, amino, substituted amino, alkyl, substituted alkyl, cycloalkyl, cyano, aryl or heterocyclo; $R^5$ is hydrogen, amino, substituted amino, alkyl, substituted alkyl, cycloalkyl, cyano or heterocyclo; $R^6$ is amino, substituted amino, hydroxy or alkoxy; $R^7$ is hydrogen, alkyl, substituted alkyl, cycloalkyl, aryl or heterocyclo; and W is O or S.

Preferably, $R^1$ is —NHCH₃, —NHCH₂CH₃, —NHCH(CH₃)₂, —NH(CH₂)₂CH₃, —NH(CH)₂OCH₃, —NH(CH₂)₂N(CH₃)₂, (R)—NHCH(CH₃)CH₂CH₃, (S)—NHCH(CH₃)CH₂CH₃, (R)—NHCH(CH₃)CH₂CH₂OCH₃, (S)—NHCH(CH₃)CH₂CH₂OCH₃, (R)-tetrahydrofuran-3-ylamino, (S)-tetrahydrofuran-3-ylamino, 4-morpholinoethylamino, 4-morpholinopropylamino, 1-piperidinoethylamino, 1-piperidinopropylamino or cyclopropylamino.

In one preferred embodiment of Formula (I), substituent A is (a); $R^3$ and $R^4$ are each hydrogen; and $R^1$ and $R^2$ are as defined hereinabove. It is more preferred that $R^2$ is hydrogen.

In another preferred embodiment of Formula (I), A is (a); $R^3$ is fluoro at the para-position; $R^4$ is hydrogen; and $R^1$ and $R^2$ are as defined hereinabove.

In a further preferred embodiment of Formula (I), A is (a); $R^3$ is fluoro at the meta-position; $R^2$ and $R^4$ are each hydrogen; and $R^1$ is as defined hereinabove.

In still another preferred embodiment of Formula (I), A is (a); $R^3$ is fluoro at the ortho-position; $R^2$ and $R^4$ are each hydrogen; and $R^1$ is as defined hereinabove.

In another preferred embodiment of Formula (I), A is (a); $R^2$ is hydrogen; $R^3$ is fluoro at the ortho-position; $R^4$ is —NH$_2$; and $R^1$ is as defined hereinabove.

In another preferred embodiment of Formula (I), A is (a); $R^2$ is fluoro; $R^3$ is fluoro at the ortho-position; $R^4$ is hydrogen; and $R^1$ is as defined hereinabove.

In yet another preferred embodiment of Formula (I), A is (b); W is O; $R^2$ is hydrogen; $R^3$ is fluoro at the ortho-position; and $R^5$ is —NH$_2$; and $R^1$ is as defined hereinabove.

In still another preferred embodiment of Formula (I), A is (d); $R^2$ is hydrogen; $R^3$ is fluoro at the ortho-position; and $R^1$, $R^6$ and $R^7$ are as defined hereinabove. More preferably, $R^6$ is —NH$_2$, —N(CH$_2$CH$_3$)$_2$, —NHCH$_2$CH$_3$, —NH(CH$_2$)$_2$CH$_3$ or —OH; and $R^7$ is hydrogen, —CH$_3$, hydroxylethyl or —CH$_2$CH$_3$.

Another embodiment of the instant invention relates to a compound of Formula (II)

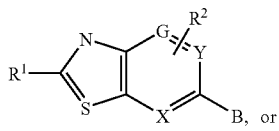

an enantiomer, diastereomer, or a pharmaceutically-acceptable salt thereof, wherein B is independently selected from:

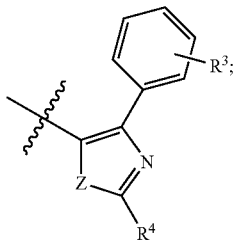

(a)

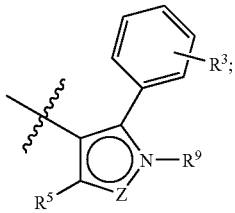

(b)

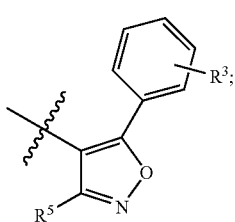

(c)

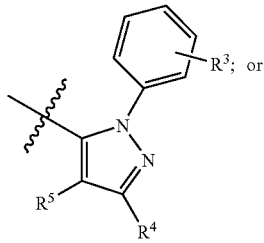

(d)

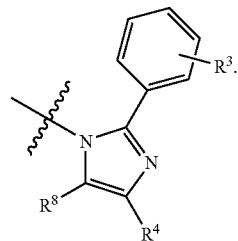

(e)

In this embodiment, G, X and Y are independently CH or N, wherein at each occurrence at least one of G, X or Y is N and the other two of G, X or Y are CH; $R^1$ is hydrogen, halo, amino, substituted amino, alkyl, substituted alkyl, cycloalkyl, aryl or heterocyclo; $R^2$ is hydrogen, halo, cyano, $C_1$-$C_4$ alkyl or $C_3$-$C_6$ cycloalkyl; $R^3$ is hydrogen, halo, cyano, optionally substituted $C_1$-$C_4$ alkyl, optionally substituted $C_3$-$C_6$ cycloalkyl, amino or substituted amino; $R^4$ is hydrogen, amino, substituted amino, alkyl, substituted alkyl, cycloalkyl, cyano, aryl or heterocyclo; $R^5$ is hydrogen, amino, substituted amino, alkyl, substituted alkyl, cycloalkyl, cyano, or heterocyclo; $R^8$ is hydrogen, cyano, alkyl, substituted alkyl, cycloalkyl or heterocyclo; $R^9$ is hydrogen, alkyl or substituted alkyl; and Z is O, S or NR$^{10}$, wherein R$^{10}$ is hydrogen, alkyl, substituted alkyl, cycloalkyl, aryl, substituted aryl or heterocyclo.

Preferably, $R^1$ is —NHCH$_3$, —NHCH$_2$CH$_3$, —NHCH(CH$_3$)$_2$, —NH(CH$_2$)$_2$CH$_3$, —NH(CH)$_2$OCH$_3$, —NH(CH$_2$)$_2$N(CH$_3$)$_2$, (R)—NHCH(CH$_3$)CH$_2$CH$_3$, (S)—NHCH(CH$_3$)CH$_2$CH$_3$, (R)—NHCH(CH$_3$)CH$_2$CH$_2$OCH$_3$, (S)—NHCH(CH$_3$)CH$_2$CH$_2$OCH$_3$, (R)-tetrahydrofuran-3-ylamino, (S)-tetrahydrofuran-3-ylamino, 4-morpholinoethylamino, 4-morpholinopropylamino, 1-piperidinoethylamino, 1-piperidinopropylamino or cyclopropylamino.

In a preferred embodiment of Formula (II), B is (a); Z is O; $R^2$ is hydrogen; $R^3$ is fluoro at the ortho-position; $R^4$ is hydrogen; and $R^1$, X, Y and G are as defined hereinabove. It is more preferred that Y is N; and X and G are each CH. It is furthermore preferred that G is N; and X and Y are each CH. It is also preferred that X is N; and Y and G are each CH.

In another preferred embodiment of Formula (II), B is (c); X is N; Y and G are each CH; $R^2$ is hydrogen; $R^3$ is fluoro at the ortho-position; and $R^5$ is hydrogen.

In another preferred embodiment of Formula (II), B is (a); Z is NR$^{10}$; $R^2$, $R^4$, $R^8$ and R$^{10}$ are each hydrogen; $R^3$ is fluoro at the ortho-position; and $R^1$, X, Y and G are as defined hereinabove. It is more preferred that Y is N; and X and G are each CH. It is also preferred that X is N; and Y and G are each CH.

In a further preferred embodiment of Formula (II), B is (b); X is N; G and Y are each CH; $R^2$ is hydrogen; $R^3$ is fluoro at the ortho-position; Z is NR$^{10}$, wherein R$^{10}$ is hydrogen or —CH₃; and R¹, R⁵ and R⁹ are as defined hereinabove. Most preferably, R⁵ is hydrogen or —NH₂; and R⁹ is hydrogen or —CH₃.

Another embodiment of the instant invention is for a process for making a compound of Formula (III):

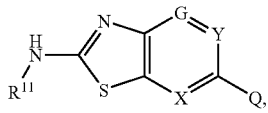

III comprising the step of reacting a compound of Formula (IV):

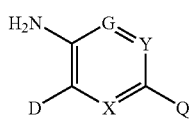

IV with R¹¹NCS and a base.

In this embodiment, each of G, X and Y is independently CH or N, wherein at each occurrence at least one of G, X or Y is N and the other two of G, X or Y are CH.

Preferably, the base is NaH, sodium tert-butoxide, potassium tert-butoxide, LDA or LHMDS.

It is preferred that R¹¹ is alkyl, substituted alkyl, cycloalkyl, aryl, heterocyclo or trimethylsylyl. It is more preferred that R¹¹ is ethyl, (R)-sec-butylamine, (S)-sec-butylamine or isopropyl.

Substituent D is a leaving group that preferably comprises halo, optionally substituted thionyl or optionally substituted sulfonyl. More preferably, D is chloro, bromo, iodo, thionyl or sulfonyl.

Preferably, Q is hydrogen, halo, cyano, nitro, RS—, substituted amino, alkyl, substituted alkyl, cycloalkyl, heterocyclic, aryl, heteroaryl, —CO₂R, —COR or —CONR₂, wherein each R is independently alkyl, aryl, arylalkyl, heterocyclo, heteroaryl, heteroarylalkyl, cycloheteroalkyl, cycloheteroalkylalkyl, cycloalkyl, cycloalkylalkyl, halo alkyl, hydroxyalkyl, alkoxyalkyl or thioalkyl, further wherein each R in —CONR₂ may be taken together with N to form 1-pyrrolidinyl, 1-piperidinyl, 1-azepinyl, 4-morpholinyl, 4-thiamorpholinyl, 1-piperazinyl, 4-alkyl-1-piperazinyl, 4-arylalkyl-1-piperazinyl, 4-diarylalkyl-1-piperazinyl, 1-pyrrolidinyl, 1-piperidinyl or 1-azepinyl, optionally substituted with alkyl, aryl, heterocyclo, alkoxy, alkylthio, halo, trifluoromethyl, hydroxy, amino, —C(O)Rᶠ, —C(═O)ORᶠ, —C(═O)NRᶠRᵍ, —S(O)₂Rᶠ, —S(O)₂ORᶠ, or —S(O)₂NRᶠRᵍ, wherein Rᶠ and Rᵍ are independently hydrogen, alkyl, substituted alkyl, aryl, substituted aryl or heterocyclo.

It is more preferred that Q is chloro or

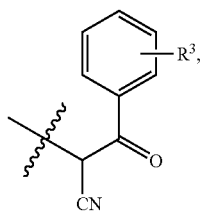

wherein R³ is hydrogen, halo, cyano, C₁-C₄ alkyl, C₃-C₆ cycloalkyl, amino or substituted amino.

Utility

The compounds of the invention are selective inhibitors of p38 kinase, and in particular, isoforms p38α and p38β. Accordingly, compounds of Formula (I) and Formula (II) have utility in treating conditions associated with p38 kinase activity. Such conditions include diseases or disorders in which cytokine levels are modulated as a consequence of intracellular signaling via p38, and in particular, diseases that are associated with an overproduction of cytokines IL-1, IL-4, IL-8, and TNF-α. As used herein, the terms "treating" or "treatment" encompass responsive and/or prophylaxis measures addressed to the disease state and/or its symptoms, e.g., measures designed to inhibit or delay the onset of the disease or disorder, achieve a full or partial reduction of the symptoms or disease state, and/or alleviate, lessen, or cure the disease and/or its symptoms. When reference is made herein to inhibition of "p-38α/β kinase," this means that either or both p38α and p38β kinase are inhibited.

In view of their activity as inhibitors of p-38α/β kinase, compounds of Formula (I) and Formula (II) are useful in treating inflammatory diseases, autoimmune diseases, destructive bone disorders, proliferative disorders, angiogenic disorders, infectious diseases, neurodegenerative diseases, viral diseases, and ischemia reperfusion conditions.

More particularly, the inventive compounds may be used to treat inflammatory diseases including, but not limited to, arthritis (e.g., rheumatoid arthritis, lyme disease arthritis, osteoarthritis, traumatic arthritis, rubella arthritis, psoriatic arthritis, gouty arthritis, and other arthritic conditions), glomerulonephritis, pancreatitis (acute or chronic), diabetes, diabetic retinopathy, macular degeneration, conjunctivitis, aplastic anemia, thrombocytopenia, gastritis, chronic thyroiditis, chronic active hepatitis, multiple sclerosis, inflammatory bowel disease, ulcerative colitis, Crohn's disease, cachexia (including cachexia secondary to infection, cancer, or heart disease), periodontal disease, Alzheimer's disease, Parkinson's disease, keloid formation, pulmonary sarcoidosis, myasthenia gravis, inflammatory reaction induced by endotoxin, Reiter's syndrome, gout, acute synovitis, diseases characterized by massive neutrophil infiltration, ankylosing spondylitis, influenze, cerebral malaria, silicosis, bone resorption disease, fever, myalgias due to infection, osteoporosis, multiple myeloma-related bone disorder, neurodegenerative disease caused by traumatic injury, and traumatic brain injury.

The inventive compounds may also be used to treat acute or chronic graft vs. host reactions (e.g., pancreatic islet allograft), acute or chronic transplant rejection (e.g., kidney, liver, heart, lung, pancreas, bone marrow, cornea, small bowel, skin allografts, skin homografts, heterografts, and/or cells derived from such organs), and skin conditions including, but not limited to scar tissue formation, eczema, atopic dermatitis, contact dermatitis, urticaria, schleroderma, scleraclerma, and psoriasis. The inventive compounds also may be used to treat allergies and respiratory conditions, including asthma, acute respiratory distress syndrome, hayfever, allergic rhinitis, and any chronic pulmonary inflammatory disease such as chronic obstructive pulmonary disease. The compounds further may be used to treat steroid resistance in asthma and allergies.

Additionally, the inventive compounds may be used to treat inflammation associated with autoimmune diseases including, but not limited to, systemic lupus erythematosis, Addison's disease, autoimmune polyglandular disease (also known as autoimmune polyglandular syndrome), and Graves' disease. The inventive compounds may be used to infectious diseases such as sepsis, septic shock, Shigellosis, and Heliobacter Pylori.

The compounds may be used to treat viral diseases including herpes simplex type 1 (HSV-1), herpes simplex type 2 (HSV-2), cytomegalovirus, Epstein-Barr, human immunodeficiency virus (HIV), acute hepatitis infection (including hepatitis A, hepatitis B, and hepatitis C), HIV infection and CMV retinitis, AIDS<ARC or malignancy, and herpes.

The inventive compounds also may be used to treat angiogenic disorders including solid tumors, ocular neovascularization, and infantile haemangiomas.

In addition, p38 inhibitors of this invention inhibit the expression of inducible pro-inflammatory proteins such as prostaglandin endoperoxide synthase-2 (PGHS-2), also referred to as cyclooxygenase-2 (COX-2). Accordingly, additional conditions that may be treated with the inventive compounds include edema, analgesia and pain, such as neuromuscular pain, headache, pain caused by cancer or surgery, dental pain and arthritis pain. In view of their COX-2 inhibitory activity, the inventive compounds also may be used to treat cancer, including, without limitation, epithelial cancer and adenocarcinoma.

Additionally, the compounds of this invention are useful to treat ischemia, including ischemia resulting from vascular occlusion, cerebral infarction, stroke, and related cerebral vascular diseases (including cerebrovascular accident and transient ischemic attack). Accordingly, the compounds may be used to treat myocardial infarction, coronary artery disease, non-Q wave MI, congestive heart failure, ventricular hypertrophy, cardiac arrhythmias, unstable angina, chronic stable angina, Prinzmetal's angina, high blood pressure, intermittent claudication, silent ischemia, cardiac hypertrophy, and peripheral occlusive arterial disease (e.g., peripheral arterial disease, critical leg ischemia, prevention of amputation, and prevention of cardiovascular morbidity such as MI, stroke or death).

Additionally, in view of their activity in treating ischemia, the compounds of the invention may be useful to treat symptoms or consequences occurring from thrombosis, atherosclerosis, peripheral arterial disease, and thrombotic or thromboembolic symptoms or consequences associated with and/or caused by one or more of the following: thromboembolic stroke (including that resulting from atrial fibrillation or from ventricular or aortic mural thrombus), venous thrombosis (including deep vein thrombosis), arterial thrombosis, cerebral thrombosis, pulmonary embolism, cerebral embolism, thrombophilia (e.g., Factor V Leiden, and homocystinenimia), coagulation syndromes and coagulopathies (e.g., disseminated intravascular coagulation), restenosis (e.g., following arterial injury induced endogenously or exogenously), atrial fibrillation, and ventricular enlargement (including dilated cardiac myopathy and heart failure). The compounds of the invention also may be used to treat symptoms or consequences of atherosclerotic diseases and disorders, such as atherosclerotic vascular disease, atherosclerotic plaque rupture, atherosclerotic plaque formation, transplant atherosclerosis, and vascular remodeling atherosclerosis. The compounds of the invention further may be used to treat symptoms or consequences of thrombotic or thromboembolic conditions associated with cancer, surgery, inflammation, systematic infection, artificial surfaces (such as stents, blood oxygenators, shunts, vascular access ports, vascular grafts, artificial valves, etc.), interventional cardiology such as percutaneous transluminal coronary angioplasty (PTCA), immobility, medication (such as oral contraceptives, hormone replacement therapy, and heparin), pregnancy and fetal loss, and diabetic complications including retinopathy, nephropathy, and neuropathy.

The compounds of the present invention may be used for the preservation of tissue, for example, the preservation of tissue as relates to organ transplantation and surgical manipulation. The compounds may be used to treat diseases or disorders in other tissues or muscles that are associated with ischemic conditions and/or to enhance the strength or stability of tissue and muscles. For example, the compounds may be used to treat muscle cell damage and necrosis and/or to enhance athletes' performance.

Additional diseases and disorders that may be treated with the inventive compounds include irritable bowel syndrome, leukemia, CNS disorders associated with cerebral ischemia, such as cerebral infarction, cerebral edema and the like, and diseases associated with proliferation of smooth muscle cells, mesangial cells, and fibroblasts. Such diseases include renal fibrosis, hepatic fibrosis, prostate hypertrophy, and pulmonary fibrosis.

The inventive compounds also may be used to treat veterinary viral infections, such as lentivirus infections, including, but not limited to, equine infectious anemia virus; or retro virus infections, including feline immunodeficiency virus, bovine immunodeficiency virus, and canine immunodeficiency virus.

When the terms "p38 associated condition" or "p38 associated disease or disorder" are used herein, each is intended to encompass all of the conditions identified above as if repeated at length, as well as any other condition that is modulated by p38 kinase activity.

The present invention thus provides methods for treating such conditions, comprising administering to a subject in need thereof an effective amount of at least one compound of Formula (I) or Formula (II), or a pharmaceutically-acceptable salt, hydrate, or prodrug thereof. The methods of treating p38 kinase-associated conditions may comprise administering compounds of Formula (I) or Formula (II) alone or in combination with each other and/or other suitable therapeutic agents such as anti-inflammatory drugs, antibiotics, anti-viral agents, anti-oxidants, cholesterol/lipid lowering agents, anti-tumor agents including antiproliferative agents, and agents used to treat ischemia.

Examples of suitable other anti-inflammatory agents with which the inventive compounds may be used include aspirin, cromolyn, nedocromil, theophylline, zileuton, zafirlukast, monteleukast, pranleukast, indomethacin, and lipoxygenase inhibitors; non-steroidal antiinflammatory drugs (NSAIDs) (such as ibuprofen and naproxin); TNF-α inhibitors (such as tenidap and rapamycin or derivatives thereof), or TNF-α antagonists (e.g., infliximab, enbrel, D2E7, OR1384), cytokine modulators (e.g. TNF-alpha converting enzyme [TACE] inhibitors, Interleukin-1 converting enzyme (ICE) inhibitors, Interleukin-1 receptor antagonists), prednisone, dexamethasone, Enbrel®, cyclooxygenase inhibitors (i.e., COX-1 and/or COX-2 inhibitors such as Naproxen®, Celebrex®, or Vioxx®), CTLA4-Ig agonists/antagonists (LEA29Y), CD40 ligand antagonists, IMPDH inhibitors (such as mycophenolate [CellCept®] and VX-497), integrin antagonists, alpha-4 beta-7 integrin antagonists, cell adhesion inhibitors, interferon gamma antagonists, ICAM-1, prostaglandin synthesis inhibitors, budesonide, clofazimine, CNI-1493, CD4 antagonists (e.g., priliximab), other p38 mitogen-activated protein kinase inhibitors, protein tyrosine kinase (PTK) inhibitors, IKK inhibitors, therapies for the treatment of irritable bowel syndrome (e.g., Zelmac®, Zelnorm®, and Maxi-K® openers such as those disclosed in U.S. Pat. No. 6,184,231 B1), or other NF-κB inhibitors (such calphostin, CSAIDs, and quinoxalines as disclosed in U.S. Pat. No. 4,200,750); corticosteroids (such as beclomethasone, triamcinolone, budesonide, fluticasone, flunisolide, dexamethasone, prednisone, and dexamethasone); disassociated steroids; chemokine receptor modulators (including CCR1, CCR2, CCR3, CCR4, and CXCR2 receptor antagonists); secretory and cytosolic phospholipase A2 inhibitors, VLA4 antagonists, glucocorticoids, salicylates, nitric oxide, and other immunosuppressants; and nuclear translocation inhibitors, such as deoxyspergualin (DSG).

To treat pain, the inventive compounds may be used in combination with aspirin, NSAIDs, or with 5-HT 1 receptor agonists such as buspirone, sumitriptan, eletriptan or rizatriptan.

Examples of suitable antibiotics with which the inventive compounds may be used include β-lactams (e.g., penicillins, cephalosporins and carbopenams); β-lactam and lactamase inhibitors (e.g., augamentin); aminoglycosides (e.g., tobramycin and streptomycin); macrolides (e.g., erythromycin and azithromycin); quinolones (e.g., cipro and tequin); peptides and deptopeptides (e.g. vancomycin, synercid and daptomycin); metabolite-based anti-biotics (e.g., sulfonamides and trimethoprim); polyring systems (e.g., tetracyclins and rifampins); protein synthesis inhibitors (e.g., zyvox, chlorophenicol, clindamycin, etc.); and nitro-class antibiotics (e.g., nitrofurans and nitroimidazoles).

Examples of suitable antiviral agents for use with the inventive compounds include nucleoside-based inhibitors, protease-based inhibitors, and viral-assembly inhibitors.

Examples of suitable anti-osteoporosis agents for use in combination with the compounds of the present invention include alendronate, risedronate, PTH, PTH fragment, raloxifene, calcitonin, RANK ligand antagonists, calcium sensing receptor antagonists, TRAP inhibitors, selective estrogen receptor modulators (SERM) and AP-1 inhibitors.

Examples of suitable anti-oxidants for use in combination with the compounds of the present invention include lipid peroxidation inhibitors such as probucol, BO-653, Vitamin A, Vitamin E, AGI-1067, and α-lipoic acid.

A further use of the compounds of this invention is in combination with steriodal or non-steroidal progesterone receptor agonists ("PRA"), such as levonorgestrel, medroxyprogesterone acetate (MPA).

The inventive compounds also may be used in combination with anti-diabetic agents, such as biguanides (e.g. metformin), glucosidase inhibitors (e.g. acarbose), insulins (including insulin secretagogues or insulin sensitizers), meglitinides (e.g. repaglinide), sulfonylureas (e.g., glimepiride, glyburide and glipizide), biguanide/glyburide combinations (e.g., glucovance), thiazolidinediones (e.g. troglitazone, rosiglitazone and pioglitazone), PPAR-alpha agonists, PPAR-gamma agonists, PPAR alpha/gamma dual agonists, SGLT2 inhibitors, inhibitors of fatty acid binding protein (aP2) such as those disclosed in U.S. Pat. No. 6,548,529 and assigned to the present assignee, glucagon-like peptide-1 (GLP-1), glucagon phosphorylase, and dipeptidyl peptidase IV (DP4) inhibitors.

In addition, the compounds may be used with agents that increase the levels of cAMP or cGMP in cells for a therapeutic benefit. For example, the compounds of the invention may have advantageous effects when used in combination with phosphodiesterase inhibitors, including PDE1 inhibitors (such as those described in Journal of Medicinal Chemistry, Vol. 40, pp. 2196-2210 [1997]), PDE2 inhibitors, PDE3 inhibitors (such as revizinone, pimobendan, or olprinone), PDE4 inhibitors (such as rolipram, cilomilast, or piclamilast), PDE7 inhibitors, or other PDE inhibitors such as dipyridamole, cilostazol, sildenafil, denbutyline, theophylline (1,2-dimethylxanthine), ARIFLO™ (i.e., cis-4-cyano-4-[3-(cyclopentyloxy)-4-methoxyphenyl]cyclohexane-1-carboxylic acid), arofyline, roflumilast, C-11294A, CDC-801, BAY-19-8004, cipamfylline, SCH351591, YM-976, PD-189659, mesiopram, pumafentrine, CDC-998, IC-485, and KW-4490.

The inventive compounds may also be useful in combination with anticancer strategies and chemotherapies such as taxol and/or cisplatin. The compounds may be used in conjunction with antitumor agents such as paclitaxel, adriamycin, epithilones, cisplatin, and carboplatin.

In view of their usefulness in treating ischemia, the inventive compounds may be used in combination with agents for inhibiting FIFO-ATPase, including efrapeptin, oligomycin, autovertin B, azide, and compounds described in U.S. Publication No. 2004-0039033A1, published Feb. 26, 2004, and assigned to the present assignee; alpha- or beta-adrenergic blockers (such as propranolol, nadolol, carvedilol, and prazosin), or -β-adrenergic agonists (such as albuterol, terbutaline, formoterol, salmeterol, bitolterol, pilbuterol, and fenoterol); antianginal agents such as nitrates, for example, sodium nitrates, nitroglycerin, isosorbide mononitrate, isosorbide dinitrate, and nitrovasodilators; antiarrhythmic agents including Class I agents (such as propafenone); Class II agents (propranolol); Class III agents (such as sotalol, dofetilide, amiodarone, azimilide and ibutilide); Class IV agents (such as ditiazem and verapamil); $K^+$ channel modulators such as IAch inhibitors and inhibitors of the Kv 1 subfamily of $K^+$ channel openers such as IKur inhibitors (e.g., compounds disclosed in U.S. Pat. No. 6,706,720, assigned to the present assignee); and gap-junction modulators such as connexions; anticoagulant or antithrombotic agents including aspirin, warfarin, ximelagtran, low molecular weight heparins (such as lovenox, enoxaparain, and dalteparin), anti-platelet agents such as GPIIb/GPIIIa blockers (e.g., abciximab, eptifibatide and tirofiban), thromboxane receptor antagonists (e.g., ifetroban), P2Y1 and P2Y12 antagonists (e.g., clopidogrel, ticlopidine, CS-747, and aspirin/clopidogrel combinations), and Factor Xa inhibitors (e.g., fondaprinux); and diuretics such as sodium-hydrogen exchange inhibitors, chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetanide, triamtrenene and amiloride.

Additionally, the inventive compounds may be used in combination with lipid profile modulators and antiatherosclerotic agents including HMG-CoA reductase inhibitors (e.g., pravastatin, simvastatin, atorvastatin, fluvastatin, cerivastatin, AZ4522, itavastatin [Nissan/Kowa]), ZD-4522 (a.k.a. rosuvastatin, atavastatin or visastatin), pravachol, squalene synthetase inhibitors, fibrates, bile acid sequestrants (such as questran), niacin and niacin/statin combinations, lipooxygenase inhibitors, ileal Na+/bile acid cotransporter inhibitors, ACAT1 inhibitors, ACAT2 inhibitors, dual ACAT1/2 inhibitors, microsomal triglyceride transport protein inhibitors (such as disclosed in U.S. Pat. Nos. 5,739,135, 5,712,279 and 5,760,246), cholesterol absorption inhibitors (such as Zetia®), cholesterol ester transfer protein inhibitors (e.g., CP-529414), PPAR-delta agonists, PPAR-alpha agonists, dual PPAR-alpha/delta agonists, LXR-alpha agonists, LXR-beta agonists, LXR dual alpha/beta agonists, and SCAP modulators.

The combination of the inventive compounds with other therapeutic agents may prove to have additive and synergistic effects. The combination may be advantageous to increase the efficacy of the administration or decrease the dosage to reduce possible side-effects.

The above other therapeutic agents, when employed in combination with the compounds of the present invention, may be used, for example, in those amounts indicated in the Physicians' Desk Reference (PDR) or as otherwise determined by one of ordinary skill in the art. In the methods of the present invention, such other therapeutic agent(s) may be administered prior to, simultaneously with, or following the administration of the inventive compounds.

The present invention also provides pharmaceutical compositions capable of treating p38-kinase associated conditions, including TNF-α, IL-1, and/or IL-8 mediated conditions, as described above. The inventive compositions may contain other therapeutic agents as described above. Pharmaceutical compositions may be formulated by employing conventional solid or liquid vehicles or diluents, as well as pharmaceutical additives of a type appropriate to the mode of desired administration (e.g., excipients, binders, preservatives, stabilizers, flavors, etc.) according to techniques such as those well known in the art of pharmaceutical formulations.

The compounds of Formula (I) and Formula (II) may be administered by any means suitable for the condition to be treated, which may depend on the need for site-specific treatment or quantity of drug to be delivered. Topical administration is generally preferred for skin-related diseases, and systematic treatment preferred for cancerous or pre-cancerous conditions, although other modes of delivery are contemplated. For example, the compounds may be delivered orally, such as in the form of tablets, capsules, granules, powders, or liquid formulations including syrups; topically, such as in the form of solutions, suspensions, gels or ointments; sublingually; buccally; parenterally, such as by subcutaneous, intravenous, intramuscular or intrasternal injection or infusion techniques (e.g., as sterile injectable aq. or non-aq. solutions or suspensions); nasally such as by inhalation spray; topically, such as in the form of a cream or ointment; rectally such as in the form of suppositories; or liposomally. Dosage unit formulations containing non-toxic, pharmaceutically acceptable vehicles or diluents may be administered. The compounds may be administered in a form suitable for immediate release or extended release. Immediate release or extended release may be achieved with suitable pharmaceutical compositions or, particularly in the case of extended release, with devices such as subcutaneous implants or osmotic pumps.

Exemplary compositions for topical administration include a topical carrier such as PLASTIBASE®(mineral oil gelled with polyethylene).

Exemplary compositions for oral administration include suspensions which may contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which may contain, for example, microcrystalline cellulose, dicalcium phosphate, starch, magnesium stearate and/or lactose and/or other excipients, binders, extenders, disintegrants, diluents and lubricants such as those known in the art. The inventive compounds may also be orally delivered by sublingual and/or buccal administration, e.g., with molded, compressed, or freeze-dried tablets. Exemplary compositions may include fast-dissolving diluents such as mannitol, lactose, sucrose, and/or cyclodextrins. Also included in such formulations may be high molecular weight excipients such as celluloses (AVICEL®) or polyethylene glycols (PEG); an excipient to aid mucosal adhesion such as hydroxypropyl cellulose (HPC), hydroxypropyl methyl cellulose (HPMC), sodium carboxymethyl cellulose (SCMC), and/or maleic anhydride copolymer (e.g., GANTREZ®); and agents to control release such as polyacrylic copolymer (e.g., CARBOPOL 934®). Lubricants, glidants, flavors, coloring agents and stabilizers may also be added for ease of fabrication and use.

Exemplary compositions for nasal aerosol or inhalation administration include solutions which may contain, for example, benzyl alcohol or other suitable preservatives, absorption promoters to enhance absorption and/or bioavailability, and/or other solubilizing or dispersing agents such as those known in the art.

Exemplary compositions for parenteral administration include injectable solutions or suspensions which may contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid.

Exemplary compositions for rectal administration include suppositories which may contain, for example, suitable non-irritating excipients, such as cocoa butter, synthetic glyceride esters or polyethylene glycols, which are solid at ordinary temperatures but liquefy and/or dissolve in the rectal cavity to release the drug.

The effective amount of a compound of the present invention may be determined by one of ordinary skill in the art, and includes exemplary dosage amounts for a mammal of from about 0.05 to 100 mg/kg of body weight of active compound per day, which may be administered in a single dose or in the form of individual divided doses, such as from 1 to 4 times per day. It will be understood that the specific dose level and frequency of dosage for any particular subject may be varied and will depend upon a variety of factors, including the activity of the specific compound employed, the metabolic stability and length of action of that compound, the species, age, body weight, general health, sex and diet of the subject, the mode and time of administration, rate of excretion, drug combination, and severity of the particular condition. Preferred subjects for treatment include animals, most preferably mammalian species such as humans, and domestic animals such as dogs, cats, horses, and the like. Thus, when the term "patient" is used herein, this term is intended to include all subjects, most preferably mammalian species, that are affected by mediation of p38 enzyme levels.

Compounds of Formula (I) and Formula (II), including the compounds described in the examples hereof, have been tested in one or more of the assays described below and have shown activity as inhibitors of p38α/β enzymes and TNF-α.

Biological Assays

Generation of p38 Kinases cDNAs of human p38α, β, and γ isozymes were cloned by PCR. These cDNAs were subcloned in the pGEX expression vector (Pharmacia). GST-p38 fusion protein was expressed in *E. Coli* and purified from bacterial pellets by affinity chromatography using glutathione agarose. p38 fusion protein was activated by incubating with constitutively active MKK6. Active p38 was separated from MKK6 by affinity chromatography. Constitutively active MKK6 was generated according to Raingeaud et al. [Mol. Cell. Biol., 1247-1255 (1996)].

TNF-α Production by LPS-Stimulated PBMCs

Heparinized human whole blood was obtained from healthy volunteers. Peripheral blood mononuclear cells (PBMCs) were purified from human whole blood by Ficoll-Hypaque density gradient centrifugation and resuspended at a concentration of $5 \times 10^6$/ml in assay medium (RPMI medium containing 10% fetal bovine serum). 50 µl of cell suspension was incubated with 50 µl of test compound (4× concentration in assay medium containing 0.2% DMSO) in 96-well tissue culture plates for 5 minutes at RT. 100 µl of LPS (200 ng/ml stock) was then added to the cell suspension and the plate was incubated for 6 hours at 37° C. Following incubation, the culture medium was collected and stored at −20° C. TNF-α concentration in the medium was quantified using a standard ELISA kit (Pharmingen-San Diego, Calif.). Concentrations of TNF-α and $IC_{50}$ values for test compounds (concentration of compound that inhibited LPS-stimulated TNF-α production by 50%) were calculated by linear regression analysis.

p38 Assay

The assays were performed in V-bottomed 96-well plates. The final assay volume was 60 µl prepared from three 20 µl additions of enzyme, substrates (MBP and ATP) and test compounds in assay buffer (50 mM Tris pH 7.5, 10 mM $MgCl_2$, 50 mM NaCl and 1 mM DTT). Bacterially expressed, activated p38 was pre-incubated with test compounds for 10 min. prior to initiation of reaction with substrates. The reaction was incubated at 25° C. for 45 min. and terminated by adding 5 µl of 0.5 M EDTA to each sample. The reaction mixture was aspirated onto a pre-wet filtermat using a Skatron Micro96 Cell Harvester (Skatron, Inc.), then washed with PBS. The filtermat was then dried in a microwave oven for 1 min., treated with MeltilLex A scintillation wax (Wallac), and counted on a Microbeta scintillation counter Model 1450 (Wallac). Inhibition data were analyzed by nonlinear least-squares regression using Prizm (GraphPadSoftware). The final concentration of reagents in the assays are ATP, 1 µM; [γ-$^{33}$P]ATP, 3 nM; MBP (Sigma, #M1891), 2 µg/well; p38, 10 nM; and DMSO, 0.3%.

TNF-α Production by LPS-Stimulated Mice

Mice (Balb/c female, 6-8 weeks of age, Harlan Labs; n=8/treatment group) were injected intraperitoneally with 50 µg/kg lipopolysaccharide (LPS; *E coli* strain 0111:B4, Sigma) suspended in sterile saline. Ninety minutes later, mice were sedated by $CO_2$:$O_2$ inhalation and a blood sample was obtained. Serum was separated and analyzed for TNF-alpha concentrations by commercial ELISA assay per the manufacturer's instructions (R&D Systems, Minneapolis, Minn.).

Test compounds were administered orally at various times before LPS injection. The compounds were dosed either as suspensions or as solutions in various vehicles or solubilizing agents.

ABBREVIATIONS

For ease of reference, the following abbreviations are employed herein, including the methods of preparation and Examples that follow:
° C.=degrees Celsius
µL=microliter
anhyd.=anhydrous
aq.=aqueous
Bn=Benzyl
Boc=tert-butyloxycarbonyl
CBZ=carbobenzyloxy or carbobenzoxy or benzyloxycarbonyl
$CO_2$=carbon dioxide
d=doublet
DCE=1,2-dichloroethane
DCM=dichloromethane
dd=doublet of doublet
DEAD=diethyl azodicarboxylate
DIPEA=diisopropylethylamine
DMF=dimethyl formamide
DMSO=dimethyl sulfoxide
EDC or EDCI=1-(3-Dimethylaminopropyl)-3-ethylcarbodiimide hydrochloride
EtOAc=ethyl acetate
EtOH=ethanol
g=gram(s)
h=hour(s)
HATU=O-(7-Azabenzotriazol-1-yl-N,N,N',N'-tetramethyluronim hexafluorophosphate
HCl=hydrogen chloride
HOBt=1-hydroxybenzotriazole hydrate
HPLC=high performance liquid chromatography
$K_2CO_3$=potassium carbonate
KOH=potassium hydroxide
KOtBu=potassium t-butoxide
L=liter
LCMS=high performance liquid chromatography/mass spectrometry
LDA=lithium diisopropylamide
LHMDS=lithium hexamethyldisilazide.
M=Molar
m=multipet
m-CPBA=m-chloroperbenzoic acid
MeOH=methanol
mg=milligram(s)
MHz=megahertz
min=minute(s)
mL=milliliter
mmol=millimole(s)
mol=moles
MS=mass spectrometry
N=Normal
$Na_2S_2O_3$=sodium thiosulfate
NaH=sodium hydride
NaOEt=sodium ethoxide
NaOH=sodium hydroxide
NMP=N-methylpyrrolidinone
NMR=nuclear magnetic resonance
Pd=palladium
Pd/C=palladium on carbon
PMB=p-methoxybenzyl
$POCl_3$=phosphorous oxychloride
Ret. time or tR=retention time (minutes)
rt=room temperature
s=singlet
sat or sat'd=saturated
sec=second (s)
TEA=triethylamine
TFA=trifluoroacetic acid
THF=tetrahydrofuran
TMS=trimethylsilyl
X=Br, I Methods of Preparation The compounds of Formula (I) and Formula (II) may generally be prepared according to the following schemes and the knowledge of one skilled in the art.

Scheme 1

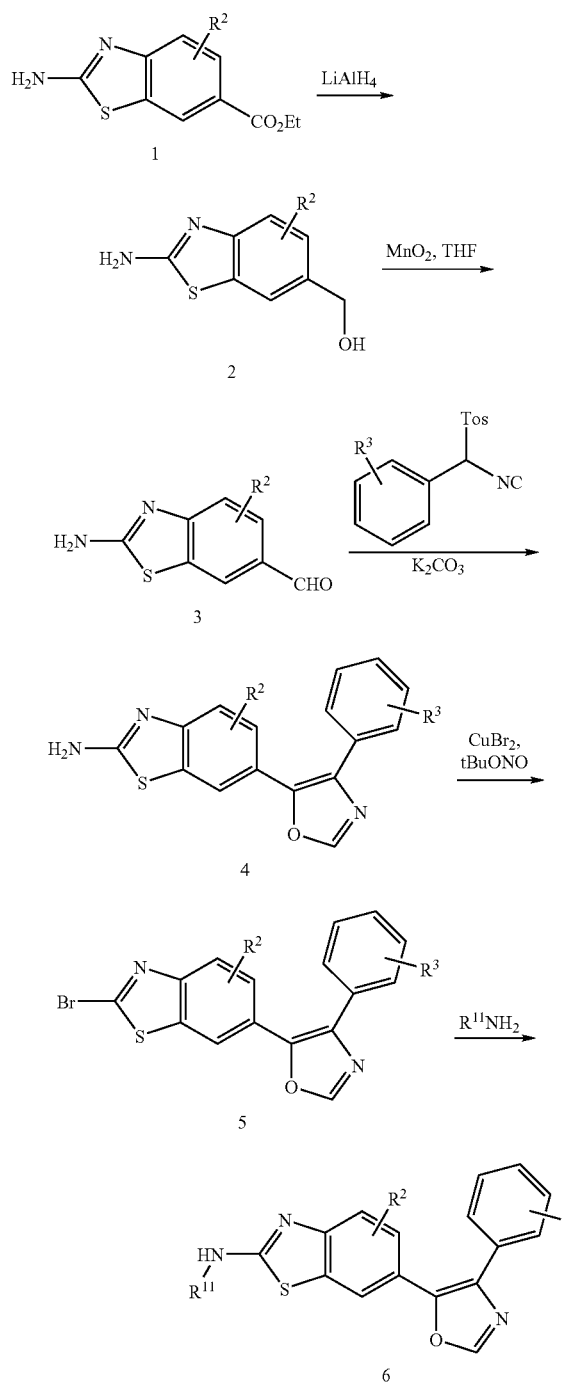

Scheme 2

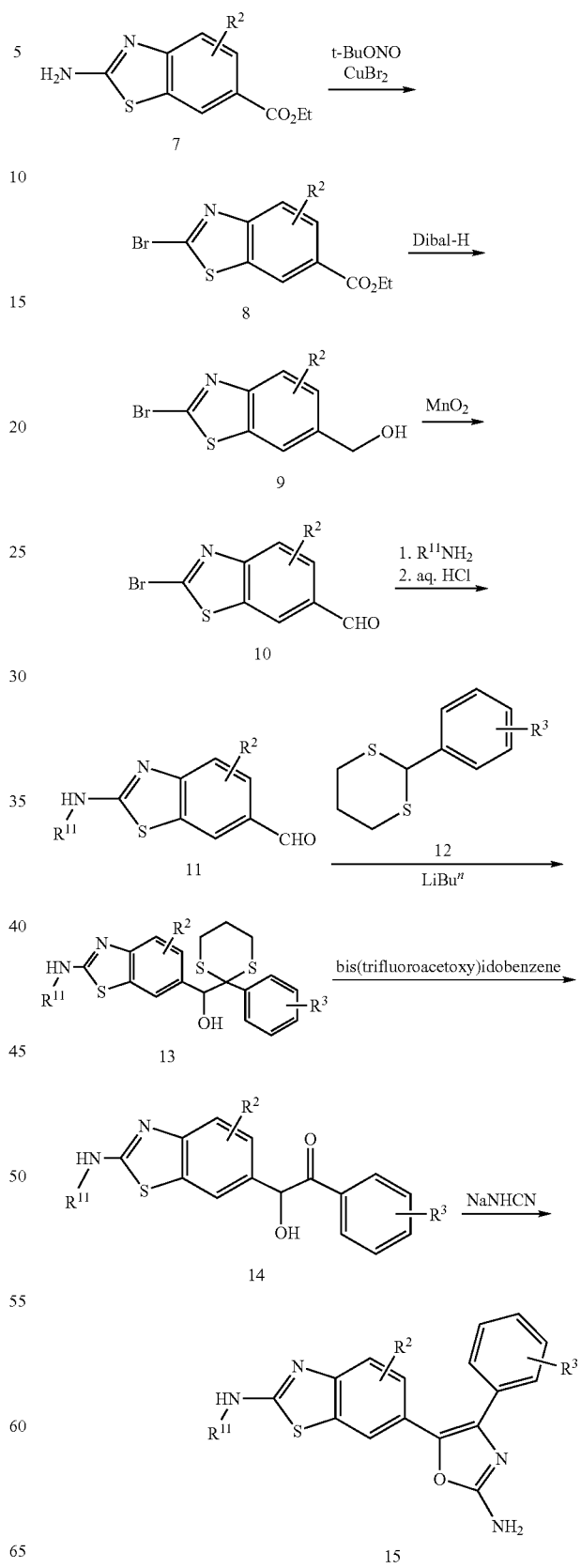

The preparation of the compound of formula 6 is shown in Scheme 1. Reduction of the ester of formula 1 with a reducing agent, such as lithium aluminum hydride, affords the alcohol of formula 2. Oxidation of 2 with an oxidizing agent, such as manganese (IV) oxide, provides an aldehyde of formula 3. Treatment of 3 with a TOSMIC reagent, such as [1-phenyl-1-tosyl]methyl isocyanide, gives rise to the compound of formula 4. Reaction of 4 with tert-butyl nitrite in the presence of copper (II) bromide and a subsequent substitution reaction with an amine supplies the compound of formula 6.

The compound of formula 15 can be prepared according to Scheme 2. The 2-aminobenzothiazole of formula 7 is converted to the 2-bromobenzothiazole of formula 8. The latter compound was transformed to the compound of formula 11 by reduction of the ester functionality of 8, oxidation of the resulting alcohol of formula 9, and replacement of the bromide 10 with an amine. Treatment of dithiane 12, made by methods known in the art, with a strong base, such as n-butyllithium, followed by 13 gives the compound of formula 14. Deprotection of the carbonyl functionality of 13 and reaction of the resulting product of formula 14 with sodium hydrogencyanamide provide compounds of formula 15.

The preparation of the compound of formula 23 is outlined in Scheme 3. The 2-aminobenzothiazole of formula 17 is made from the 4-aminophenylacetonitrile of formula 16 with potassium thiocyanate and bromine in acetic acid. Conversion of 17 into the compound of formula 19 is performed in a manner known in the art, and shown previously in Scheme 1 for converting the compound of formula 4 to 6. Treatment of 19 with a strong base, such as LHMDS, followed by a benzoate, affords the compound of formula 20. Cyclozation of 20 with hydrazine or hydroxylamine provides the compound of formula 21. Reductive amination at different conditions give the compounds of formulae 22 and 23.

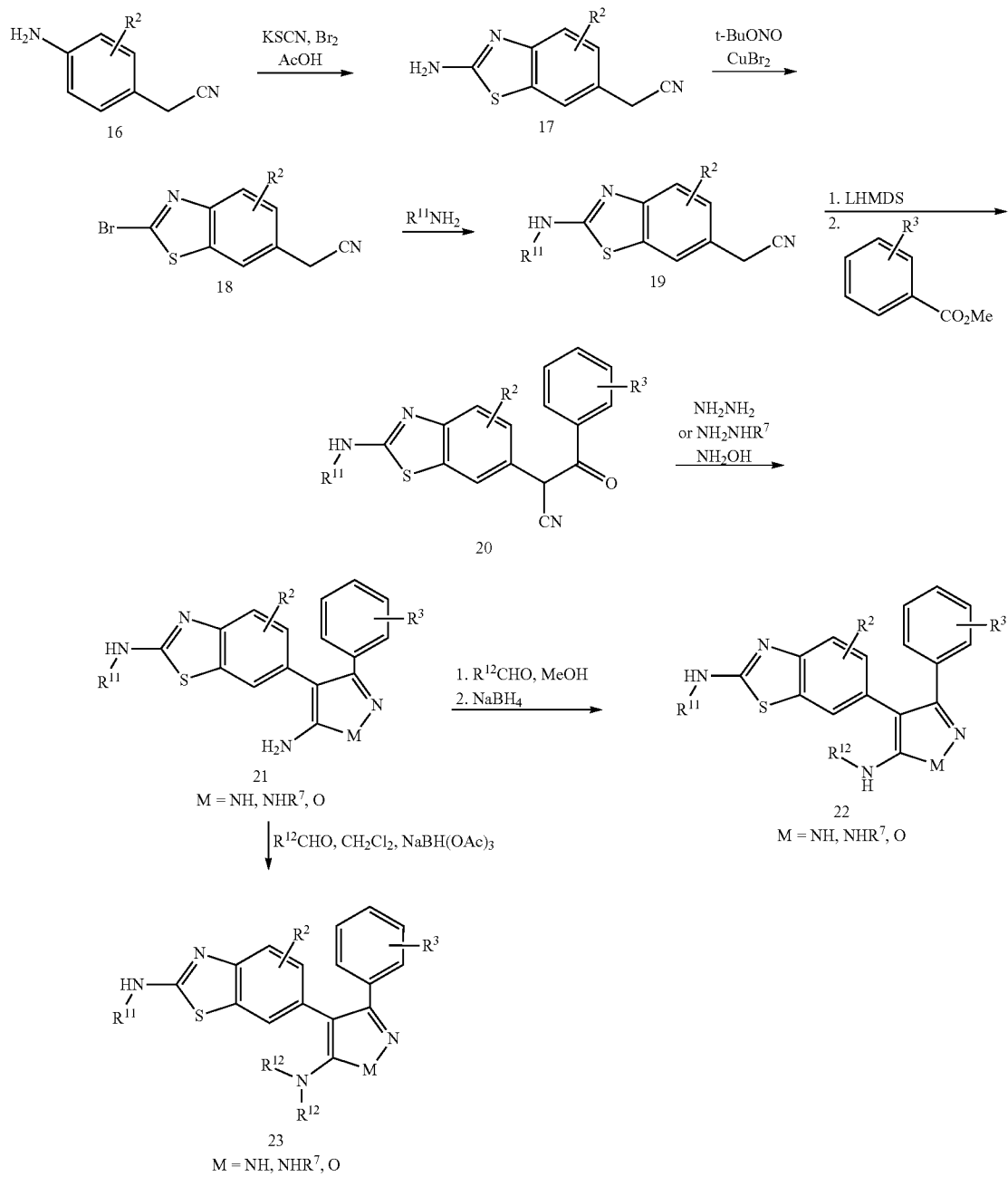

Scheme 3

Scheme 4
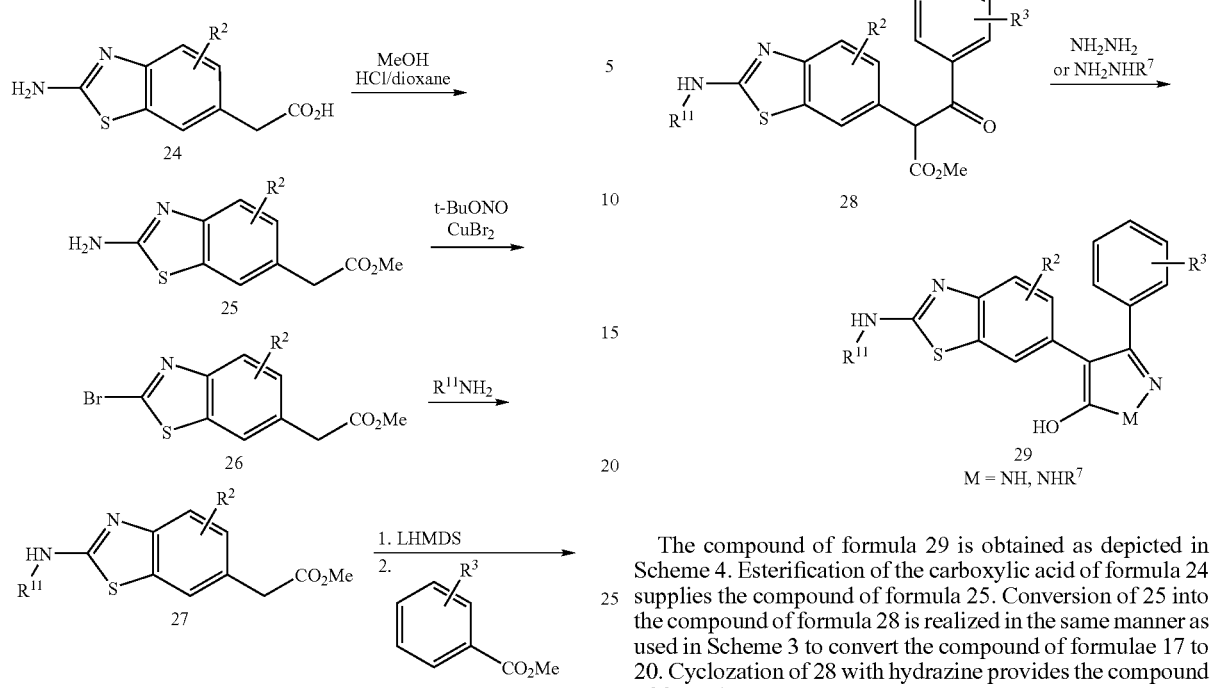
The compound of formula 29 is obtained as depicted in Scheme 4. Esterification of the carboxylic acid of formula 24 supplies the compound of formula 25. Conversion of 25 into the compound of formula 28 is realized in the same manner as used in Scheme 3 to convert the compound of formulae 17 to 20. Cyclization of 28 with hydrazine provides the compound of formula 29.
Scheme 5
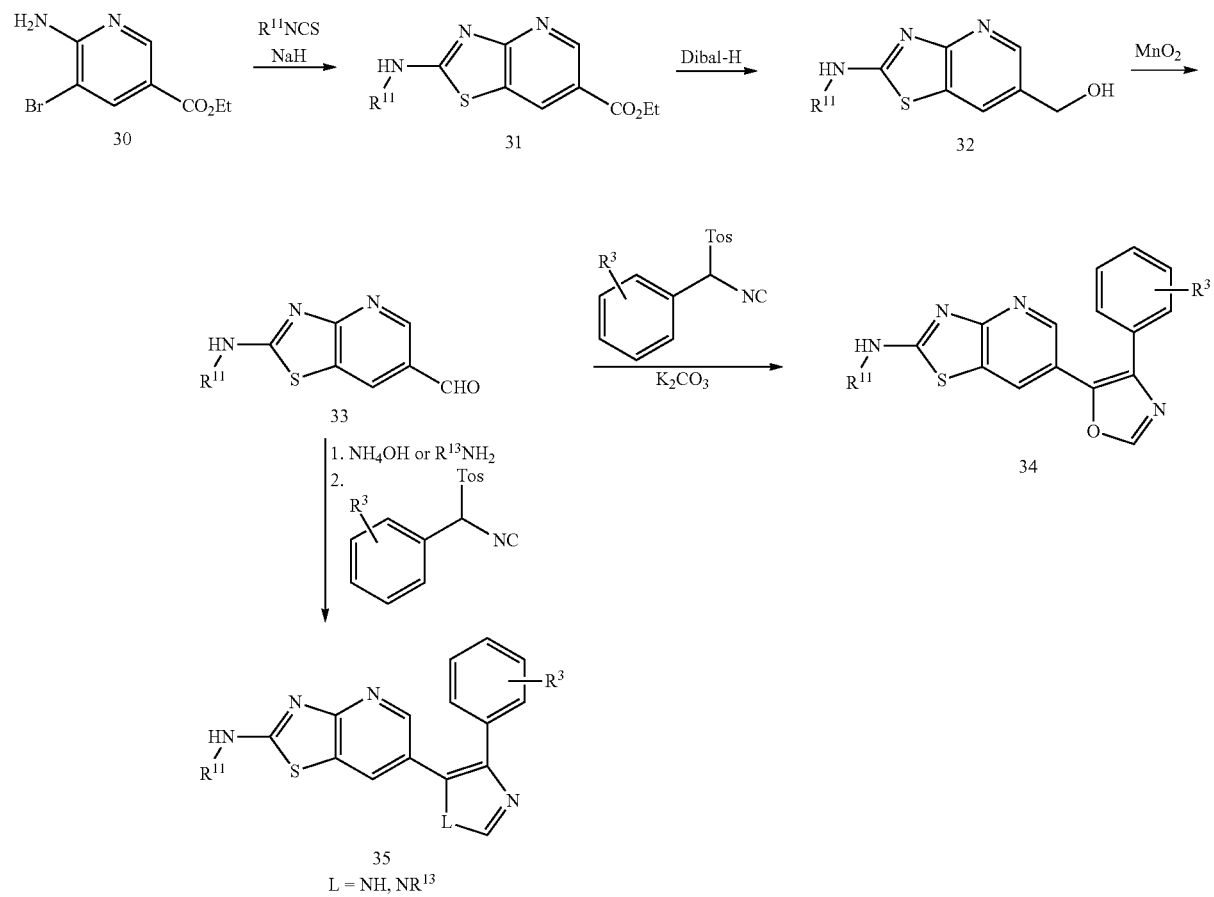

The preparation of compounds of formulae 34 and 35 are illustrated in Scheme 5. Reacting ethyl 6-amino-5-bromonicotinate 30 with isothiocyanate in the presence of a base, such as sodium hydride, provides the compound of formula 31. Conversion of 31 into the compound of formula 34 follows the same chemistry as used in Scheme 1 to convert compounds of formula 1 to 4. Treatment of the aldehyde of formula 33 with ammonia or amines followed by treatment with TOSMIC reagents gives the compound of formula 35.

Scheme 6

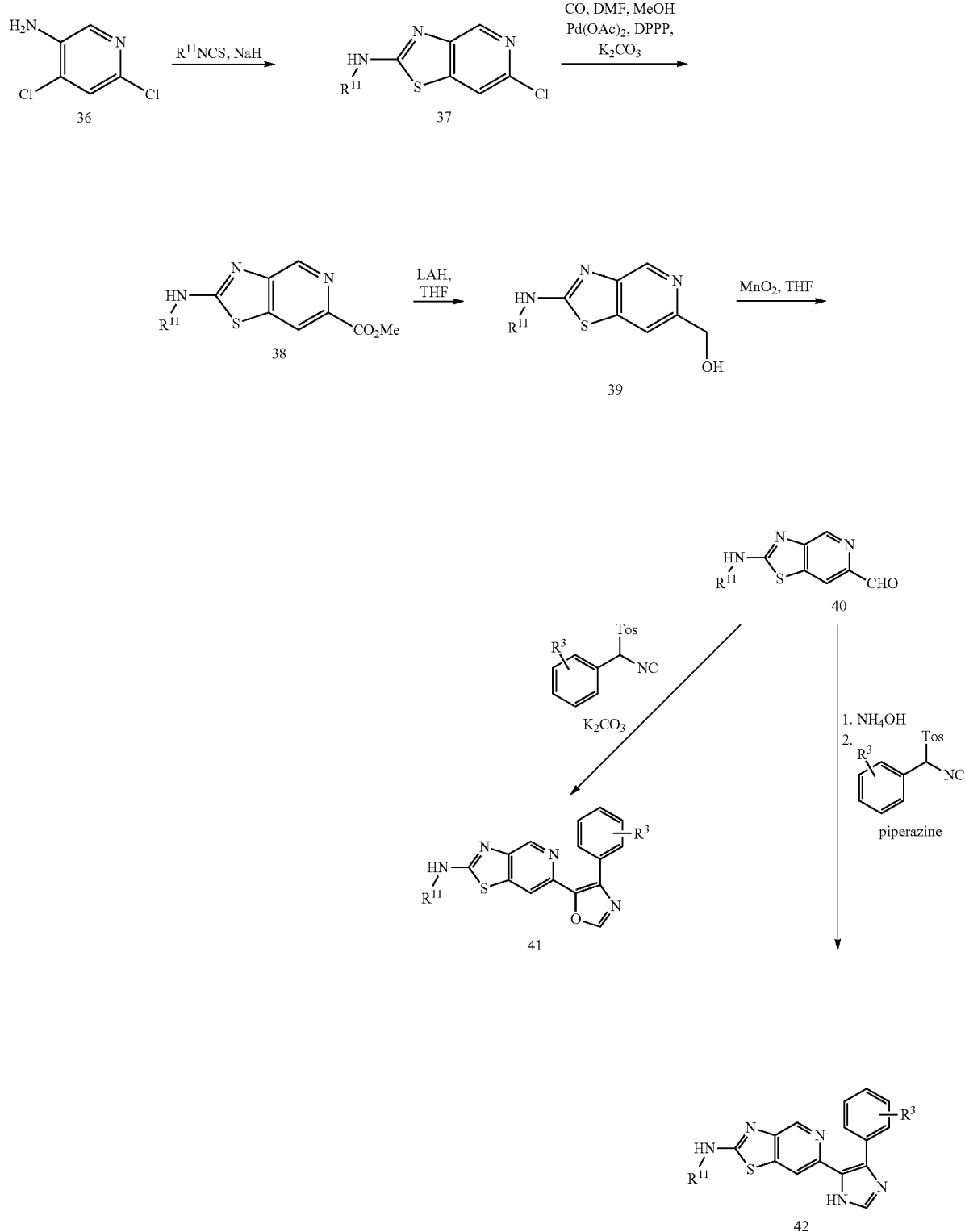

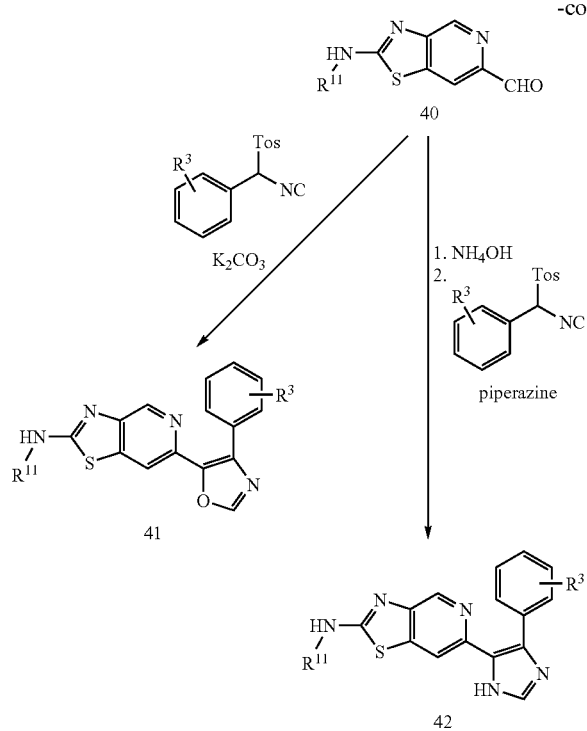
Scheme 6 shows that the compounds of formulae 41 and 42 are synthesized in the same manner as the compounds of formulae 34 and 35 (Scheme 5).
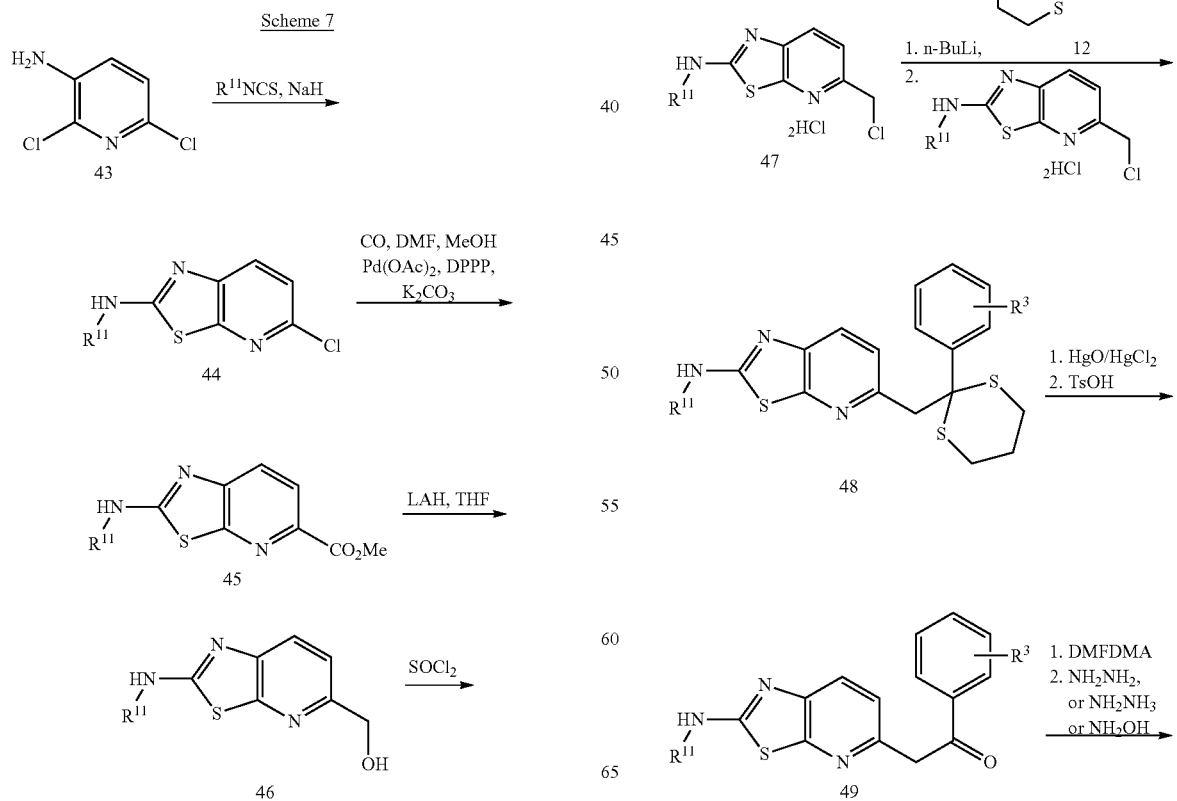

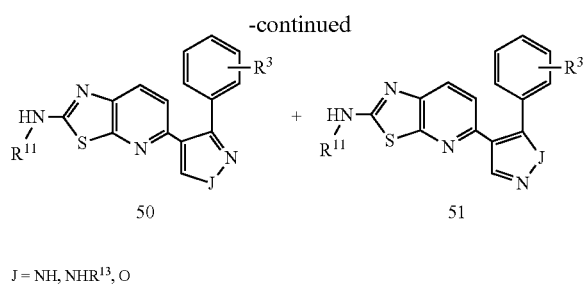

J = NH, NHR¹³, O

The compounds of formulae 50 and 51 are synthesized as showed in Scheme 7. Treatment of 2,6-dichloropyridin-3-amine 43 with isothiocyanate in the presence of a base, such as sodium hydride, provides the compound of formula 44. Carbonation of 44 affords the compound of formula 45. Reduction of 45 and subsequent reaction of the resulting alcohol of formula 46 with thionyl chloride gives the compound of formula 47. Treating dithiane 12 with a strong base, such as n-butyllithium, followed by treatment with 47 results in the formation of the compound of formula 48. Deprotection of the carbonyl functionality of 48 supplies the ketone of formula 49. The compounds of formula 50 and 51 are obtained by reacting 49 with DMFDMA and subsequent treatment with hydrazine and hydroxylamine.

As shown in Scheme 8, the alcohol of formula 46 can also be oxidized into the aldehyde of formula 52, which is further converted into the compounds of formulae 53 and 54, as previously described.

Scheme 9

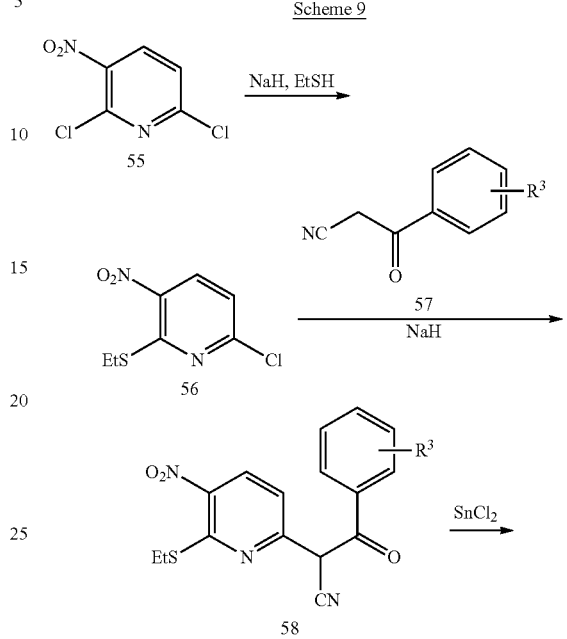

Scheme 8

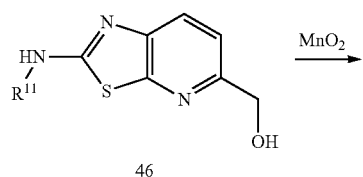

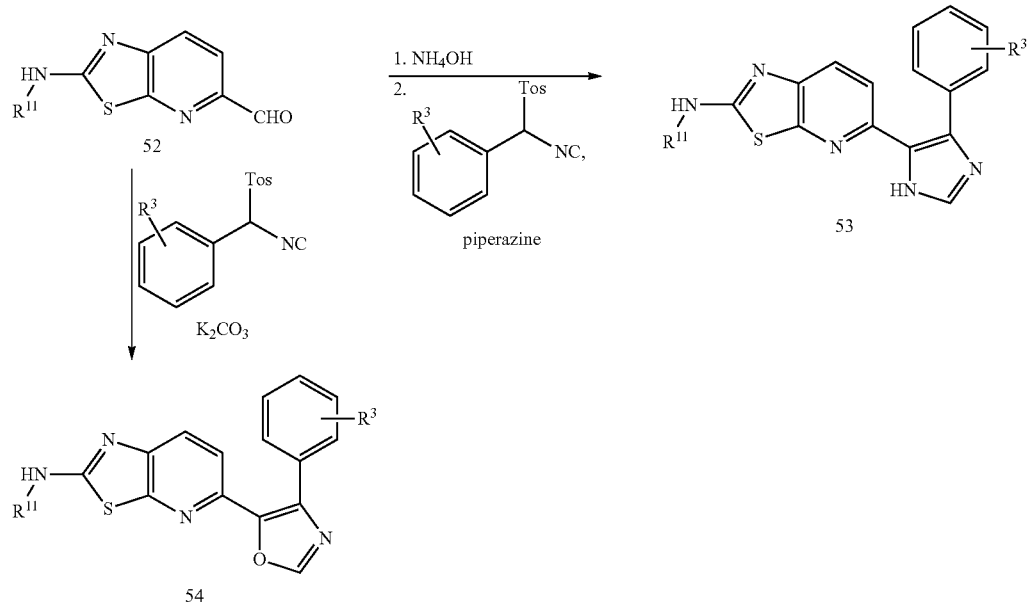

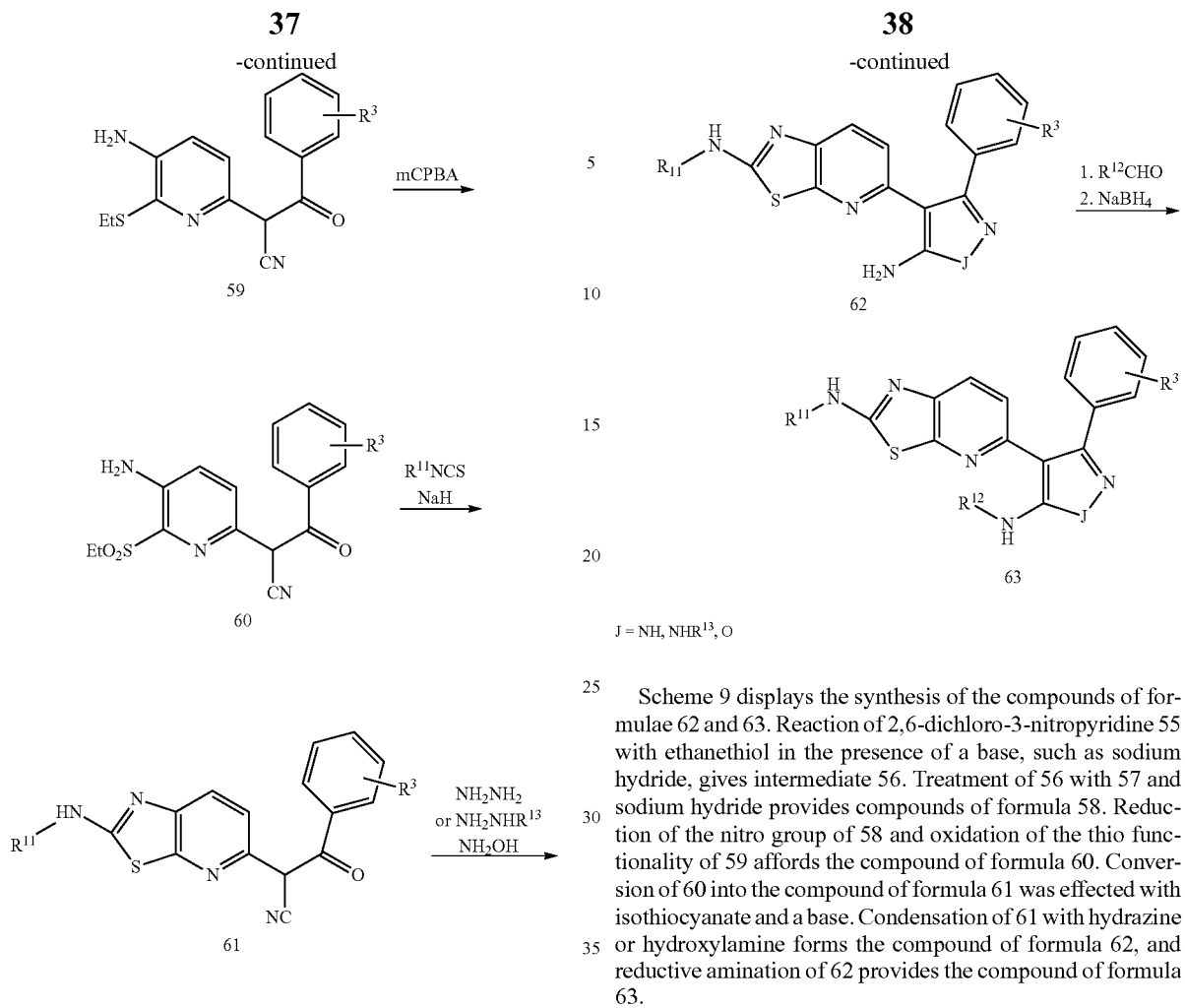

Scheme 9 displays the synthesis of the compounds of formulae 62 and 63. Reaction of 2,6-dichloro-3-nitropyridine 55 with ethanethiol in the presence of a base, such as sodium hydride, gives intermediate 56. Treatment of 56 with 57 and sodium hydride provides compounds of formula 58. Reduction of the nitro group of 58 and oxidation of the thio functionality of 59 affords the compound of formula 60. Conversion of 60 into the compound of formula 61 was effected with isothiocyanate and a base. Condensation of 61 with hydrazine or hydroxylamine forms the compound of formula 62, and reductive amination of 62 provides the compound of formula 63.

Scheme 10

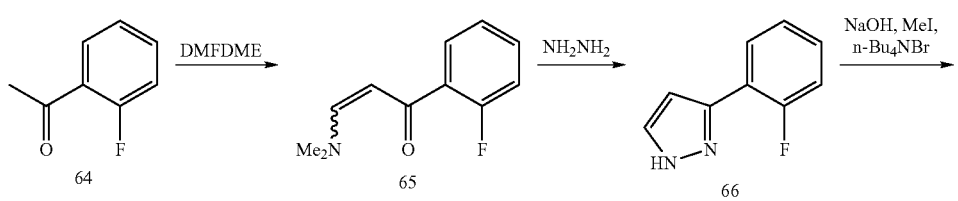

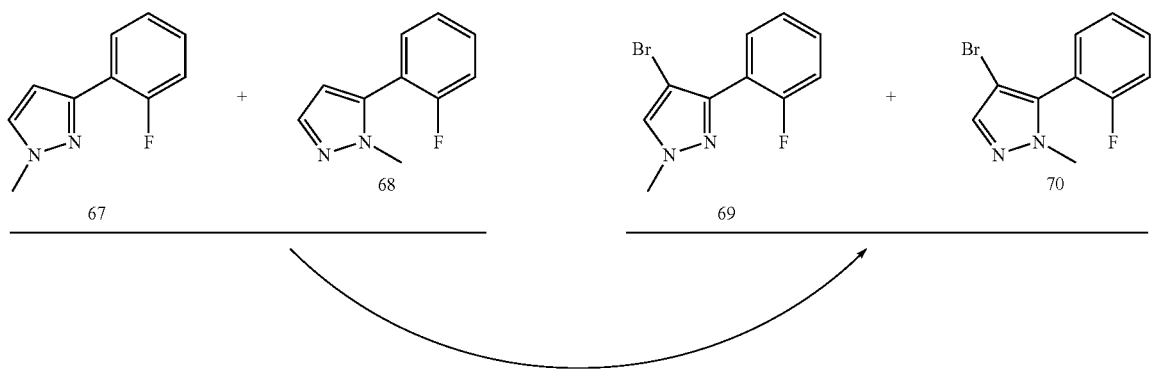

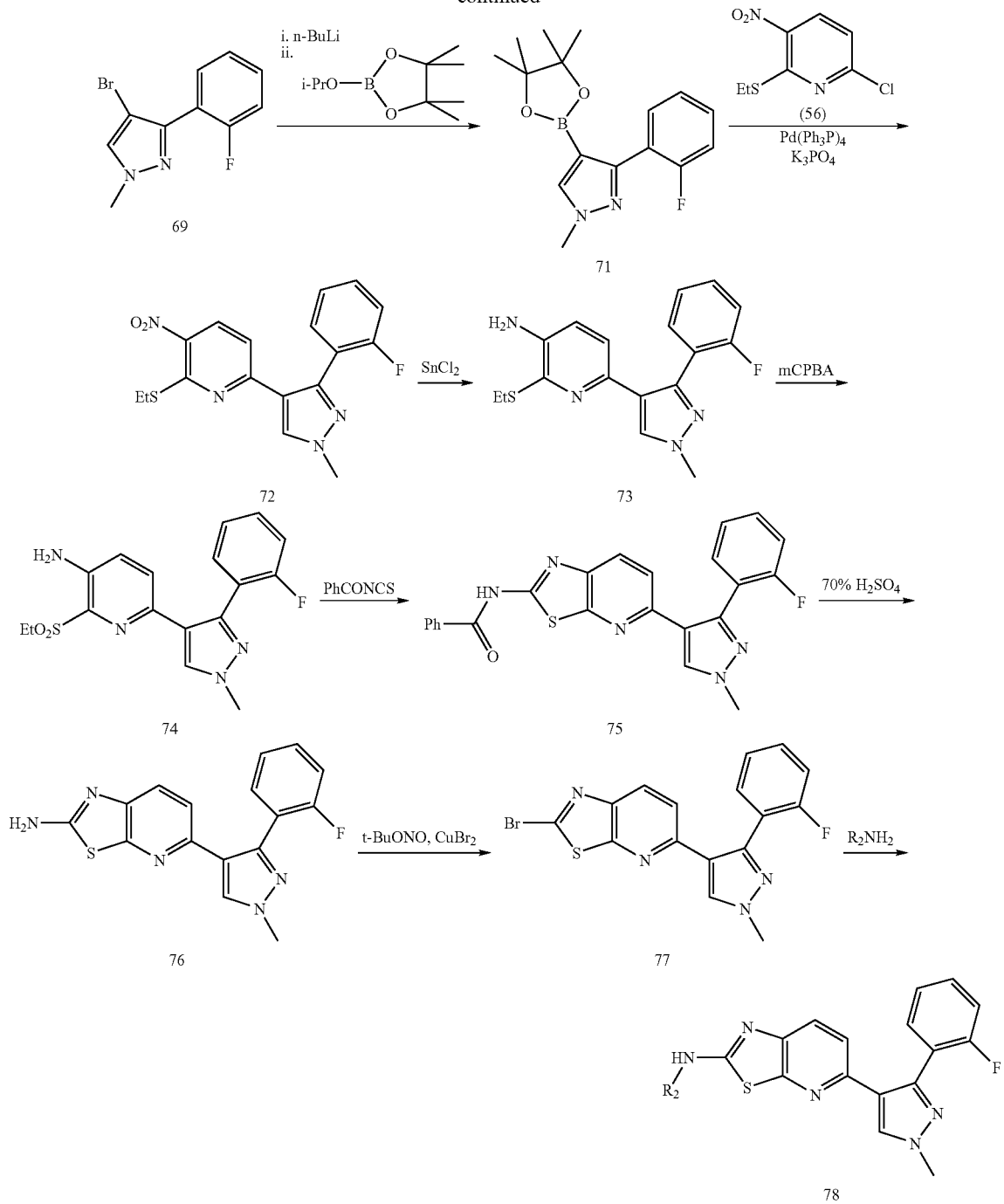

Scheme 10 displays the synthetic route to 78. The commercially available 2'-fluoroacetophenone (64) was treated with DMFDMA to provide 65, which was reacted with hydrazine to form 66. N-Methylation of 66 was effected with NaOH and MeI in the presence of n-Bu$_4$NBr to give a mixture of two isomers 67 and 68. Without separation, the mixture was reacted with bromine to afford a mixture of 69 and 70. The isomer 69 was then separated from the mixture by flush chromatography. Treatment of 69 with n-BuLi, followed by 2-isopropoxy-4,4,5,5-tetramethyl-1,3,2-dioxaborolane, supplied 71. Reaction of 71 with 56 in the presence of Pd(Ph$_3$P)$_4$ and K$_3$PO$_4$ gave rise to 72. Nitro reduction of 72 with SnCl$_2$ yielded 73, which was oxidized to sulfone 74 with mCPBA. Reaction of 74 with benzyol isothiocyanate and a subsequent acid hydrolysis of amide 75 led to the formation of 76. The aminoazabenzothizole 76 was converted to bromoazabenzothizole 77 with t-butyl nitrite and CuBr$_2$. Analogues 78 were obtained by treating 77 with amines.

EXAMPLES

In the following examples, HPLC retention times were determined using the following conditions: Ballistic YMC S5 ODS 4.6×50 mm column with a binary solvent system where solvent A=10% methanol, 90% water, 0.2% phosphoric acid and solvent B=90% methanol, 10% water, and 0.2% phosphoric acid, flow rate=4 mL/min, linear gradient time=4 min, start % B=0, final % B=100.

LCMS analyses were performed using the following conditions: Waters Xterra 5 μM 4.6×30 mm column with a binary solvent system where solvent A=10% methanol, 90% water, 0.1% trifluoroacetic acid and solvent B=90% methanol, 10% water, and 0.1% trifluoroacetic acid, flow rate=4 mL/min, linear gradient time=2 min, start % B=0, final % B=100.

Preparative reverse-phase HPLC purifications were performed using the following conditions: Ballistic YMC S5 ODS 20×100 mm column with a binary solvent system where solvent A=10% methanol, 90% water, 0.1% trifluoroacetic acid and solvent B=90% methanol, 10% water, and 0.1% trifluoroacetic acid, flow rate=20 mL/min, linear gradient time=10 min, start % B=20, final % B=100.

Solvent quantities for the above HPLC retention times, HPLC purifications, and LCMS analyses are reported on volume basis.

All reagents were purchased from commercial sources, unless otherwise noted. All reactions were performed under an argon atmosphere. Reactions run in aqueous media were run under an ambient atmosphere unless otherwise noted. Yields are reported as mole %.

EXPERIMENTAL

Example 1

6-(4-(4-fluorophenyl)oxazol-5-yl)-N-(2-morpholinoethyl)benzo[d]thiazol-2-amine

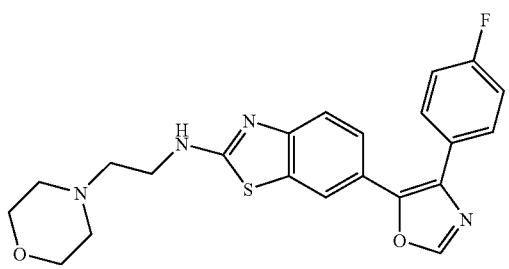

1. (2-aminobenzo[d]thiazol-6-yl)methanol

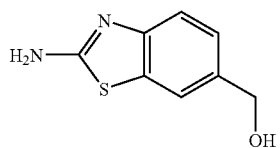

To a solution of ethyl 2-aminobenzo[d]thiazole-6-carboxylate (5.05 g, 22.7 mmol, 1.0 eq.) in THF (60 mL) under nitrogen at 0° C. was added LAH (1M, THF; 100 mL, 100 mmol, 4.4 eq.) over 20 min. After 6.5 h, ice was added, and the solution was stirred overnight. The precipitate was filtered and rinsed with EtOAc. The filtrate was concentrated in vacuo to give a solid which was triturated with Et$_2$O to give (2-aminobenzo[d]thiazol-6-yl)methanol as a yellow solid (1.90 g, 46% yield).

2. 2-aminobenzo[d]thiazole-6-carbaldehyde

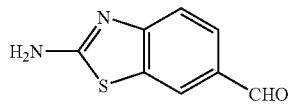

To a solution of (2-aminobenzo[d]thiazol-6-yl)methanol (1.90 g, 10.5 mmol, 1.0 eq.) in THF (75 mL) under nitrogen was added MnO$_2$ (14 g, 161 mmol, 15.3 eq.). After stirring overnight, the reaction solution was filtered through Celite and rinsed with THF. The filtrate was concentrated in vacuo to give 2-aminobenzo[d]thiazole-6-carbaldehyde as a yellow solid (1.64 g, 87% yield).

3. 6-(4-(4-fluorophenyl)oxazol-5-yl)benzo[d]thiazol-2-amine

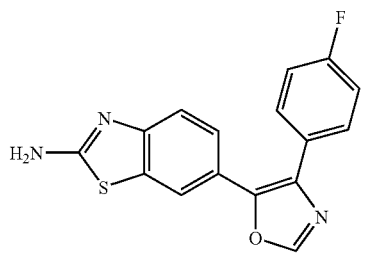

A solution of 2-aminobenzo[d]thiazole-6-carbaldehyde (0.91 g, 5.11 mmol, 1.0 eq.), 1-((4-fluorophenyl)(isocyano)methylsulfonyl)-4-methylbenzene (2.20 g, 7.60 mmol, 1.5 eq.), and K$_2$CO$_3$ (1.34 g, 9.70 mmol, 1.9 eq.) in EtOH (51 mL) was refluxed for 4 h. After cooling to room temperature, the reaction mixture was concentrated in vacuo, and the residue was taken up in CH$_2$Cl$_2$ and saturated aqueous NaHCO$_3$. After separation of the layers, the aqueous layer was extracted with CH$_2$Cl$_2$ (2×). The organic layers were combined, dried over Na$_2$SO$_4$, filtered, and concentrated in vacuo. Silica gel chromatography using CH$_2$Cl$_2$:MeOH (40:1) as eluent afforded 6-(4-(4-fluorophenyl)oxazol-5-yl)benzo[d]thiazol-2-amine as a tan solid (1.37 g, 86% yield).

4. 2-bromo-6-(4-(4-fluorophenyl)oxazol-5-yl)benzo[d]thiazole

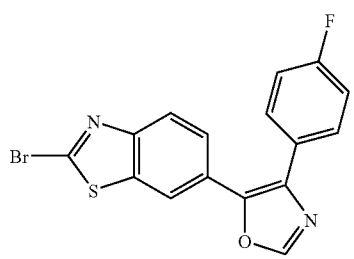

To a solution of CuBr₂ (1.16 g, 5.19 mmol, 1.3 eq.) in CH₃CN (26 mL), previously purged with nitrogen for 20 min., were added 6-(4-(4-fluorophenyl)oxazol-5-yl)benzo[d]thiazol-2-amine (1.23 g, 3.95 mmol, 1.0 eq.) and t-butyl nitrite (0.70 mL, 5.89 mmol, 1.5 eq.) at 0° C. After 3 h, the ice-water bath was removed, and the reaction was stirred to room temperature overnight. Et₂O and water were added, and the layers were separated. The aqueous layer was extracted with Et₂O (2×), and the combined organic layers were washed with saturated aqueous NaHCO₃ and brine, dried over Na₂SO₄, filtered, and concentrated in vacuo. Silica gel chromatography using CH₂Cl₂ as eluent afforded 2-bromo-6-(4-(4-fluorophenyl)oxazol-5-yl)benzo[d]thiazole as an orange solid (0.57 g, 39% yield).

5. 6-(4-(4-fluorophenyl)oxazol-5-yl)-N-(2-morpholinoethyl)benzo[d]thiazol-2-amine A solution of 2-bromo-6-(4-(4-fluorophenyl)oxazol-5-yl)benzo[d]thiazole (0.030 g, 0.080 mmol, 1.0 eq.) and 4-(2-aminoethyl)morpholine (0.073 mL, 0.556 mmol, 7.0 eq.) in THF (1.5 mL) was mechanically shaken at 54° C. overnight. After cooling to room temperature, the solution was concentrated in vacuo. MeOH was added to the residue, and the mixture was subjected to autoprep. The appropriate fractions were collected, and NaHCO₃ (s) was added. The solution was then concentrated in vacuo not to dryness and extracted with CH₂Cl₂ (3×). The organic layers were combined, dried over Na₂SO₄, filtered, and concentrated in vacuo to give 6-(4-(4-fluorophenyl)oxazol-5-yl)-N-(2-morpholinoethyl)benzo[d]thiazol-2-amine as a light yellow solid (0.0182 g, 54% yield). LC/MS (MH)=425.17.

Example 2

4-Fluoro-N-isopropyl-6-(4-phenyloxazol-5-yl)benzo[d]thiazol-2-amine

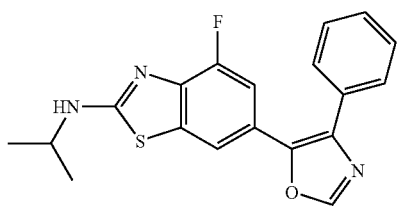

1. Methyl 3-fluoro-4-nitrobenzoate

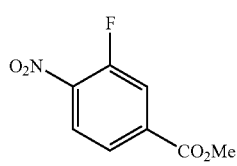

A mixture of 3-fluoro-4-nitrobenzoic acid (5.00 g, 27.0 mmol), Methanol (40 mL), and 2 N HCl in Et₂O was heated at reflux for 16 hr. Volatile material was removed under vacuum. The residue was diluted with AcOEt (150 mL), washed successively with saturated NaHCO₃ solution and brine, and dried over anhydrous MgSO₄. Evaporation of solvent under vacuum gave the title compound (5.18 g, 96% yield) as a pale yellow solid.

2. Methyl 4-amino-3-fluorobenzoate

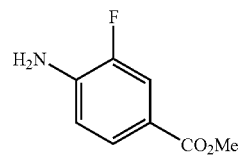

Methyl 3-fluoro-4-nitrobenzoate (5.18 g, 26.0 mmol) in a 1:1 mixture (50 mL) of EtOH and AcOEt with 10% Pd/C (0.52 g) was hydrogenated on a Parr hydrogenation apparatus at 40 psi. Pd/C was removed by filtration through a pad of Celite® 545. The filtrate was concentrated under vacuum. The residue was diluted with AcOEt, washed with brine, and dried over anhydrous MgSO₄. Evaporation of solvent under vacuum gave the title compound (4.17 g, 95% yield) as a pale solid.

3. Methyl 2-amino-4-fluorobenzo[d]thiazole-6-carboxylate

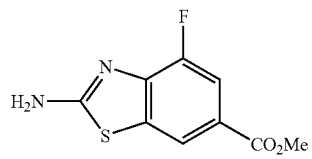

To a solution of methyl 4-amino-3-fluorobenzoate (2.00 g, 11.8 mmol) in AcOH (25 mL) was added KSCN at rt in one portion, and the resulting mixture was stirred at rt until it became a clear solution. Then, bromine (1.89 g, 11.8 mmol) in AcOH (10 mL) was added at rt over 45 min, and the whole reaction mixture was stirred at rt for 20 hr. The precipitate that formed during the reaction was removed by filtration. The filtrate was poured into water (100 mL) and basified with cons. NH₃H₂O to pH 8-9. The resulting precipitate was collected by suction filtration and dried at 60° C. under vacuum to give a crude product (1.17 g). This crude was a mixture of the title product and the starting material (methyl 4-amino-3-fluorobenzoate) in a ratio of 1.3 to 1. However, this crude product was directly used in the next step without further purification.

4. Methyl 2-bromo-4-fluorobenzo[d]thiazole-6-carboxylate

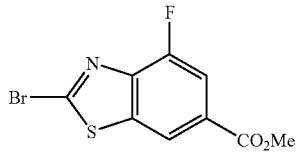

To a mixture of copper (II) bromide (1.79 g, 7.91 mmol) in acetonitrile (30 mL) was added tert-butyl nitrite (1.35 mL, 90%, 10.2 mmol) at 0° C., followed by the addition of the above prepared crude methyl 2-amino-4-fluorobenzo[d]thiazole-6-carboxylate (1.17 g) in one portion. The resulting mixture was stirred at rt for 20 hr before it was diluted with AcOEt (150 mL), washed successively with water and brine, and dried over anhydrous MgSO$_4$. After the solvent was removed under vacuum, the residue was subjected to silca gel chromatography (7% AcOEt/hexane) to afford the title compound (0.335 g, 10% yield over two steps) as a pale solid.

5. (2-Bromo-4-fluorobenzo[d]thiazol-6-yl)methanol

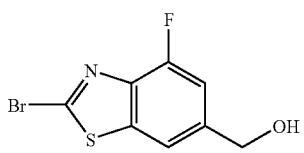

To a solution of methyl 2-bromo-4-fluorobenzo[d]thiazole-6-carboxylate (0.335 g, 1.15 mmol) in toluene (10 mL) and THF (5 mL) was added Dibal-H (4.8 mL, 4.8 mmol) at −78° C. over 10 min. The resulting mixture was allowed to warm to rt and stirred at rt for 3 hr before it was poured into ice cold water (100 mL). The mixture was stirred at rt for 30 min and then filtered through Celite® 545. The organic layer was separated and the aqueous layer was extracted twice with AcOEt. The combined organic phase was dried over anhydrous MgSO$_4$ and concentrated under vacuum. Evaporation of solvent under vacuum gave the title compound (0.269 g, 89% yield) as a white solid.

6. 2-Bromo-4-fluorobenzo[d]thiazole-6-carbaldehyde

A mixture of (2-bromo-4-fluorobenzo[d]thiazol-6-yl) methanol (0.269 g, 1.03 mmol) and manganese (IV) oxide (activated, 85%, 1.47 g, 14.4 mmol) in THF (15 mL) was stirred at rt for 16 hr. Solid material was removed by filtration through Celite® 545, and the filtrate was concentrated under vacuum. The residue was diluted with AcOEt, washed with brine, and dried over anhydrous MgSO$_4$. Evaporation of solvent under vacuum gave the title compound (0.136 g, 61% yield) as a white solid.

7. 4-Fluoro-2-(isopropylamino)benzo[d]thiazole-6-carbaldehyde

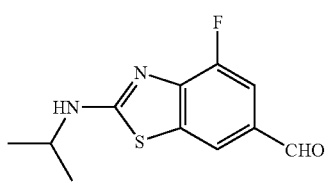

A mixture of 2-bromo-4-fluorobenzo[d]thiazole-6-carbaldehyde (0.110 g, 0.423 mmol) and isopropylamine (0.15 ml, 1.76 mmol) in 1,4-dioxane (5 mL) was heated at reflux for 36 hr. The solution was allowed to cool to rt and 1N HCl (1 mL) was added. The mixture was heated at 60° C. for 1 hr. After it cooled to rt, the mixture was poured into saturated NaHCO$_3$ solution (20 mL) and extracted with AcOEt (3×25 mL). The combined extract was dried over anhydrous MgSO$_4$ and concentrated to dryness under vacuum to provide the title crude compound, which was used in the next step without further purification.

8. 4-Fluoro-N-isopropyl-6-(4-phenyloxazol-5-yl)benzo[d]thiazol-2-amine

A mixture of 4-fluoro-2-(isopropylamino)benzo[d]thiazole-6-carbaldehyde (a half amount of material obtained from step 7, ≦0.211 mmol), tosylmethyl isocyanide (60.1 mg, 0.221 mmol), and K$_2$CO$_3$ (35.1 mg, 0.254 mmol) in EtOH (6 mL) was heated at reflux for 16 hr. After it cooled to rt, the mixture was diluted with AcOEt (70 mL), washed successively with water and brine, and dried over anhydrous MgSO$_4$. The title compound (32.4 mg, 43% over two steps) was isolated as a white solid by preparative HPLC. 100% purity by LCMS; (M+H)$^+$=354.40.

Example 3

6-(2-Amino-4-(2-fluorophenyl)thiazol-5-yl)-N-isopropylbenzo[d]thiazol-2-amine

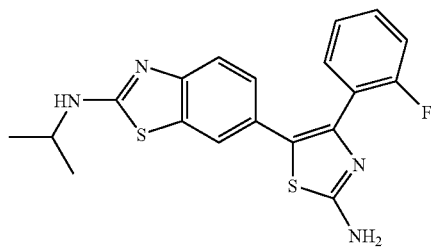

1. 2-(Isopropylamino)benzo[d]thiazole-6-carbaldehyde

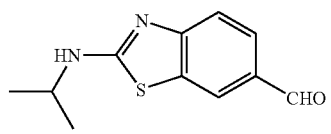

The title compound was prepared in a similar manner as 4-fluoro-2-(isopropylamino)benzo[d]thiazole-6-carbaldehyde (Example 2).

2. 2-(2-fluorophenyl)-1,3-dithiane

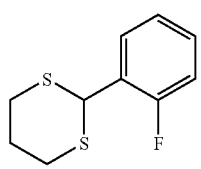

To a solution of 2-fluorobenzaldehyde (10.03 g, 80.8 mmol, 1.0 eq.) and NBS (2.16 g, 12.1 mmol, 0.2 eq.) in CH$_2$Cl$_2$ (400 mL) was added 1,3-propanedithiol (9.8 mL, 97.6 mmol, 1.2 eq.). After 0.75 h, the reaction mixture was concentrated in vacuo. The residue was diluted with CH$_2$Cl$_2$ and water, and the layers were separated. The organic layer was dried over Na$_2$SO$_4$, filtered, concentrated in vacuo, and triturated with hexanes to give 2-(2-fluorophenyl)-1,3-dithiane as a white solid (13.55 g, 78% yield).

3. (2-(2-Fluorophenyl)-1,3-dithian-2-yl)(2-(isopropylamino)benzo[d]thiazol-6-yl)methanol

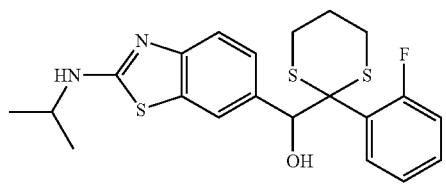

To a solution of 2-(2-fluorophenyl)-1,3-dithiane (0.820 g, 3.83 mmol) in THF (25 mL) was added n-BuLi (1.6 M in hexane, 2.3 mL, 3.68 mmol) at −10° C. over 10 min. The resulting solution was stirred at −10° C. for 30 min before a solution of 2-(isopropylamino)benzo[d]thiazole-6-carbaldehyde (0.385 g, 1.75 mmol) in THF (5 mL) was added. The mixture was stirred at between −10° C. and 5° C. for 2.5 hr, and then quenched with saturated NH$_4$Cl solution (25 mL). This was extracted with AcOEt (3×20 mL). The combined extract was washed with brine and dried over anhydrous MgSO$_4$. The title compound (0.563 g, 74% yield) was isolated as a pale yellow solid by silica gel chromatography (35% AcOEt/hexane).

4. 1-(2-Fluorophenyl)-2-hydroxy-2-(2-(isopropylamino)benzo[d]thiazol-6-yl)ethanone

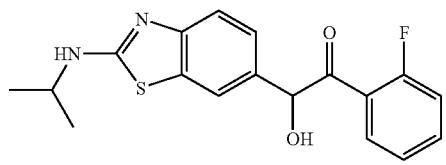

To a solution of (2-(2-fluorophenyl)-1,3-dithian-2-yl)(2-(isopropylamino)benzo[d]thiazol-6-yl)methanol (0.540 g, 1.24 mmol) in acetonitrile (8 mL) and water (1.3 mL) was added a solution bis(trifluoroacetoxy)idobenzene (0.800 g, 1.86 mmol) in acetonitrile (4 mL) at rt over 5 min. The mixture was stirred at rt for 1 hr before it was diluted with AcOEt (100 mL), washed successively with saturated NaHCO$_3$ solution and brine, and dried over anhydrous MgSO$_4$. The title compound (87.0 mg, 20% yield) was isolated as a light yellow waxy material by silica gel chromatography (3% MeOH/CH$_2$Cl$_2$).

5. 6-(2-Amino-4-(2-fluorophenyl)thiazol-5-yl)-N-isopropylbenzo[d]thiazol-2-amine A mixture of 1-(2-fluorophenyl)-2-hydroxy-2-(2-(isopropylamino)benzo[d]thiazol-6-yl)ethanone (87.0 mg, 0.253 mmol) and sodium hydrogencyanamide (32.4 mg, 0.506 mmol) in EtOH (2 mL) was heated at 90° C. in a sealed tube for 90 min. After it cooled to rt, the mixture was diluted with AcOEt, washed successively with water and brine, and dried over anhydrous MgSO$_4$. The title compound (3.72 mg) was isolated as a pale solid by prep. HPLC. 100% pure by LCMS; (M+H)$^+$=369.37.

Example 4

6-(5-Amino-3-(2-fluorophenyl)-1H-pyrazol-4-yl)-N—(R)-sec-butylbenzo[d]thiazol-2-amine

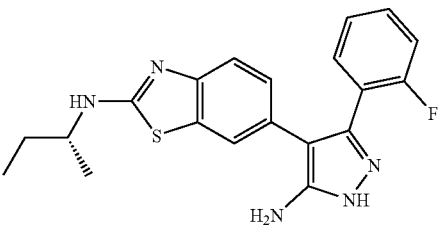

1. 2-(2-Aminobenzo[d]thiazol-6-yl)acetonitrile

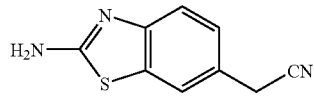

To a solution of 2-(4-aminophenyl)acetonitrile (6.00 g, 45.4 mmol) in AcOH (70 mL) was added potassium thiocyanate (17.6 g, 181 mmol) at rt in one portion. The mixture was stirred at rt until it became a clear solution. To this solution was then added a solution of bromine (2.3 mL, 44.9 mmol) in AcOH (30 mL) at rt over 1 hr. The resulting mixture was stirred at rt for 4 hr. The precipitate that formed during the reaction was collected by suction filtration, and then suspended into water (100 mL). The pH value of the aqueous suspension was adjusted to 8 with concentrated ammonium hydroxide. The insoluble product (7.39 g, 86% yield) was collected as a pale yellow solid by suction filtration and dried over Drierite® under vacuum at 65° C.

2. 2-(2-Bromobenzo[d]thiazol-6-yl)acetonitrile

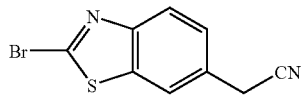

To a mixture of copper (II) bromide (7.63 g, 34.3 mmol) and t-butyl nitrite (5.3 mL, 44.6 mmol) in acetonitrile (120 mL) was added 2-(2-aminobenzo[d]thiazol-6-yl)acetonitrile (5.00 g, 26.4 mmol) at 0° C. in one portion. The resulting mixture was stirred at rt for 6 hr before it was poured into a mixture of water (120 mL) and ethyl acetate (300 mL). The whole reaction mixture was stirred at rt for 15 min. The insoluble material was removed by suction filtration through Celite® 545. The organic layer of filtrate was washed successively with water and brine. The combined aqueous layer was extracted with AcOEt. The combined organic phase was dried over anhydrous MgSO$_4$. Evaporation of solvent under vacuum provided the title compound (5.53 g, 83% yield) as a tan solid.

3. (R)-2-(2-(sec-Butylamino)benzo[d]thiazol-6-yl) acetonitrile

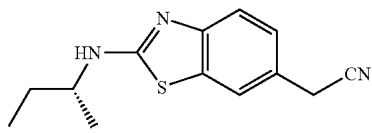

A mixture of 2-(2-bromobenzo[d]thiazol-6-yl)acetonitrile (2.00 g, 7.90 mmol) and (R)-sec-butylamine (4.0 mL, 39.4 mmol) in 1,4-dioxane (30 mL) was heated at 135° C. in a sealed bottle for 3.5 hr. The excess (R)-sec-butylamine and 1,4-Dioxane were removed under vacuum. The residue was diluted with AcOEt (150 mL), washed successively with saturated NaHCO$_3$ solution (twice) and brine, and dried over anhydrous MgSO$_4$. The title compound (1.35 g, 70% yield) was isolated as a light orange oil by ISCO (40% AcOEt/hexane).

3. 2-(2-((R)-sec-Butylamino)benzo[d]thiazol-6-yl)-3-(2-fluorophenyl)-3-oxopropanenitrile

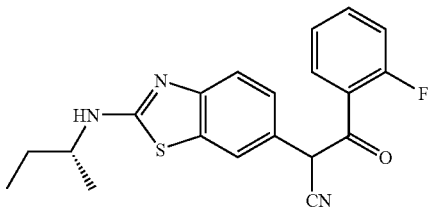

To a solution of lithium bis(trimethylsilyl)amide (1.0 M in THF, 35.3 mL) in THF (60 mL) was added a solution of (R)-2-(2-(sec-butylamino)benzo[d]thiazol-6-yl)acetonitrile (3.74 g, 15.2 mmol) in THF (60 mL) at −78° C. over 40 min. The resulting solution was stirred at −78° C. for 10 min before a solution of methyl 2-fluorobenzoate (2.5 mL, 19.6 mmol) in THF (15 mL) was added over 5 min. The mixture was stirred at −78° C. for 1 hr and then at rt for 3 hr before it was poured into ice-cold water (100 mL). After its pH value was adjusted to 9 with 6 N HCl, the mixture was extracted with AcOEt (3×60 mL). The combined extract was washed with brine and dried over anhydrous MgSO$_4$. The solution was concentrated under vacuum, and the residue was subjected to ISCO (2% MeOH/CH$_2$Cl$_2$) to give a mixture (4.09 g) of the title compound and the starting material in a ratio of 1:1.

4. 6-(5-Amino-3-(2-fluorophenyl)-1H-pyrazol-4-yl)-N—(R)-sec-butylbenzo[d]thiazol-2-amine To a solution of 2-(2-((R)-sec-butylamino)benzo[d]thiazol-6-yl)-3-(2-fluorophenyl)-3-oxopropanenitrile (approximately 50% purity, 2.00 g) in glacial AcOH (30 mL) and EtOH (15 mL) was added anhydrous hydrazine (1.7 mL, 54 mmol) at 0° C. The resulting mixture was heated at 85° C. for 16 hr. After it cooled to rt, the mixture was diluted with water (50 mL), basified with concentrated ammonium hydroxide to pH 8, and extracted with AcOEt (3×40 mL). The combined extract was washed with brine and dried over anhydrous MgSO$_4$. The title compound (0.518 g, 18% yield over two steps) was isolated by flash chromatography (5% MeOH/CH$_2$Cl$_2$). (M+H)$^+$=369.37.

Example 5

6-(5-Amino-1-ethyl-3-(2-fluorophenyl)-1H-pyrazol-4-yl)-N—(R)-sec-butylbenzo[d]thiazol-2-amine

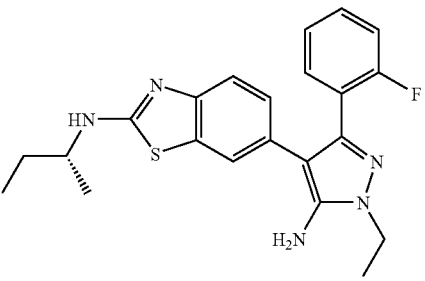

A mixture of ethyl hydrazine oxalate (0.306 g, 2.04 mmol) and triethylamine (0.34 mL, 2.44 mmol) in EtOH (2 mL) was stirred at rt for 30 min before 2-(2-((R)-sec-butylamino) benzo[d]thiazol-6-yl)-3-(2-fluorophenyl)-3-oxopropanenitrile (example 4) (approximately 50% purity, 0.150 g) and glacial AcOH (4 mL) were successively added. The whole reaction mixture was heated at 80° C. for 16 hr. After it cooled to rt, the mixture was diluted with water, basified with concentrated ammonium hydroxide to pH 8, and extracted with AcOEt (3 times). The combined extract was washed with brine and concentrated under vacuum. The title compound (7.5 mg, 3.3% yield over two steps) was isolated as a white solid by preparative HPLC and subsequent flash chromatography (45% AcOEt/CH$_2$Cl$_2$); 98% purity by LCMS, (M+H)$^+$=409.52.

Example 6

6-(5-Amino-3-(2-fluorophenyl)isoxazol-4-yl)-N—(R)-sec-butylbenzo[d]thiazol-2-amine

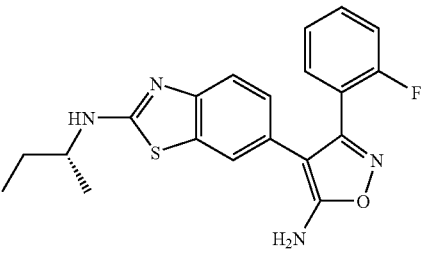

A mixture of hydroxylamine hydrochloride (0.322 g, 4.63 mmol) and triethylamine (0.65 mL, 4.66 mmol) in EtOH (7 mL) was stirred at rt for 30 min before 2-(2-((R)-sec-butylamino)benzo[d]thiazol-6-yl)-3-(2-fluorophenyl)-3-oxopropanenitrile (example 4) (approximately 50% purity, 0.170 g) and glacial AcOH (14 mL) were successively added. The whole was heated at 85° C. for 3 days. After it cooled to rt, the mixture was diluted with water (30 mL), basified with concentrated ammonium hydroxide to pH 9, and extracted with AcOEt (3×30 mL). The combined extract was washed with brine and dried over anhydrous MgSO₄. The title compound (9.7 mg, 4% yield over two steps) was isolated as a pale yellow solid by preparative HPLC and subsequent flash chromatography (20% AcOEt/CH₂Cl₂); 95% purity by LCMS, (M+H)⁺=383.23.

Example 7

N—(R)-sec-Butyl-6-(3-(2-fluorophenyl)-5-(propylamino)-1H-pyrazol-4-yl)benzo[d]thiazol-2-amine

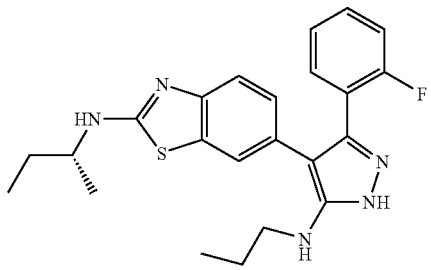

A mixture of 6-(5-amino-3-(2-fluorophenyl)-1H-pyrazol-4-yl)-N—(R)-sec-butylbenzo[d]thiazol-2-amine (example 4) (0.100 g, 0.262 mmol) and propionaldehyde (34 µL, 0.47 mmol) in methanol (2 mL) was stirred at rt for 4.5 hr before NaBH₄ (54 mg, 1.43 mmol) was added. The whole was stirred at rt for 1 hr before it was quenched with water (2 mL). The mixture was diluted with AcOEt (50 mL), washed successively with water and brine, and concentrated under vacuum. The title compound (12.5 mg, 11% yield) was isolated as a white solid by preparative HPLC and subsequent flash chromatography (65% AcOEt/CH₂Cl₂); 98% purity by LCMS, (M+H)⁺=424.20.

Example 8

3-(2-Fluorophenyl)-4-(2-(isopropylamino)benzo[D]thiazol-6-yl)-1H-pyrazol-5-ol

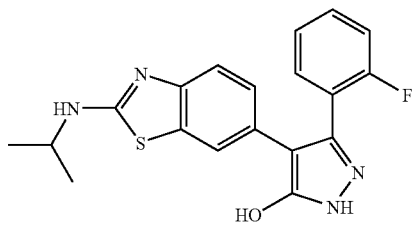

1. Methyl 2-(2-aminobenzo[d]thiazol-6-yl)acetate

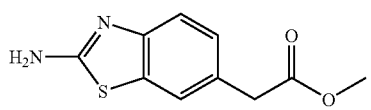

A mixture of 2-(2-aminobenzo[d]thiazol-6-yl)acetic acid (95%, 10.0 g, 45.6 mmol), methanol (50 mL), 4 N HCl/1,4-dioxane (12.0 mL, 48.0 mmol) in 1,4-dioxane (30 mL) was heated at 75° C. for 9 hr and then concentrated under vacuum. The residue was suspended into water (50 mL) and basified to pH 9 with 1N NaOH solution. The title compound (8.19 g, 81% yield) was collected as a pale solid by suction filtration and dried under vacuum at 50° C.

2. Methyl 2-(2-bromobenzo[d]thiazol-6-yl)acetate

The title compound was prepared in the same manner as 2-(2-bromobenzo[d]thiazol-6-yl)acetonitrile (Example 4, step 2).

3. Methyl 2-(2-(isopropylamino)benzo[d]thiazol-6-yl)acetate

The title compound was prepared in the same manner as (R)-2-(2-(sec-butylamino)benzo[d]thiazol-6-yl)acetonitrile (example 4, step 3).

4. Methyl 3-(2-fluorophenyl)-2-(2-(isopropylamino)benzo[d]thiazol-6-yl)-3-oxopropanoate To a solution of lithium bis(trimethylsilyl)amide (1.0 M in THF, 15.1 mL) in THF (30 mL) was added a solution of methyl 2-(2-(isopropylamino)benzo[d]thiazol-6-yl)acetate (1.60 g, 6.05 mmol) in THF (20 mL) at −78° C. over 40 min. The resulting solution was stirred at −78° C. for 15 min before a solution of methyl 2-fluorobenzoate (1.08 mL, 8.48 mmol) in THF (10 mL) was added over 5 min. The mixture was stirred at −78° C. for 1 hr and then at rt for 3 hr before it was poured into ice-cold water (100 mL). After its pH value was adjusted to 9 with 6 N HCl, the mixture was extracted with AcOEt (3×40 mL). The combined extract was washed with brine and dried over anhydrous MgSO₄. Evaporation of solvent under vacuum give the title compound (2.81 g) as an orange yellowish oil. This product was 63% pure by LCMS, but it was used in the next step without further purification.

5. 3-(2-Fluorophenyl)-4-(2-(isopropylamino)benzo[d]thiazol-6-yl)-1H-pyrazol-5-ol To a solution of methyl 3-(2-fluorophenyl)-2-(2-(isopropylamino)benzo[d]thiazol-6-yl)-3-oxopropanoate(63% purity, 0.260 g) in glacial AcOH (4 mL) and EtOH (2 mL) was added anhydrous hydrazine (0.18 mL, 5.73 mmol) at 0° C. The resulting mixture was heated at 85° C. for 4 hr. After it cooled to rt, the mixture was diluted with water (40 mL), basified with concentrated ammonium hydroxide to pH 8, and extracted with AcOEt (3×30 mL). The combined extract was washed with brine and dried over anhydrous MgSO$_4$. The title compound (55.0 mg, 27% yield over two steps) was isolated by ISCO (8% MeOH/CH$_2$Cl$_2$). (M+H)$^+$=369.21.

Example 9

N-isopropyl-6-(4-phenyloxazol-5-yl)thiazolo[4,5-b]pyridin-2-amine

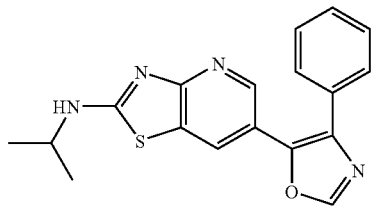

1. Ethyl 2-(isopropylamino)thiazolo[4,5-b]pyridine-6-carboxylate

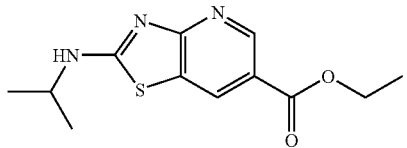

To a solution of ethyl 6-amino-5-bromonicotinate (0.780 g, 3.18 mmol) and isopropyl isothiocyanate (0.34 mL, 3.19 mmol) in DMF (8 mL) was added sodium hydride (60% oil dispersion) at 0° C. in one portion. The mixture was heated at 65° C. for 20 hr, and then at 75° C. for 40 hr. After it cooled to rt, the reaction was quenched with 1N HCl (5 mL). The mixture was poured into saturated NaHCO$_3$ solution and extracted with AcOEt (3×40 mL). The combined extract was washed with 10% lithium chloride solution (2×30 mL) and dried over anhydrous MgSO$_4$. The title compound (0.291 g, 34% yield) was isolated as a white solid by flash chromatography (60% AcOEt/hexane).

2. (2-(Isopropylamino)thiazolo[4,5-b]pyridin-6-yl)methanol

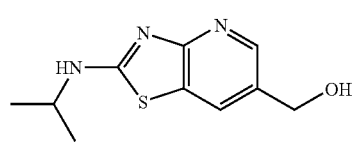

To a solution of ethyl 2-(isopropylamino)thiazolo[4,5-b]pyridine-6-carboxylate (0.278 g, 1.05 mmol) in toluene (10 mL) and THF (5 mL) was introduced Dibal-H (5.8 mL, 5.8 mmol) at −78° C. over 10 min. The resulting mixture was allowed to warm to rt and stirred for 4 hr. Additional Dibal-H (1.2 mL, 1.2 mmol) was added at rt, and the mixture was stirred for additional 1.5 hr before it was poured into ice-cold water (100 mL). The mixture was stirred at rt for 30 min, and then filtered through Celite® 545. The organic layer of filtrate was separated. The aqueous layer was basified with saturated NaHCO$_3$ solution and extracted with AcOEt. The combined organic phase was washed with brine and dried over anhydrous MgSO$_4$. Evaporation of solvent under vacuum gave the title compound as a viscous oil.

3. 2-(Isopropylamino)thiazolo[4,5-b]pyridine-6-carbaldehyde

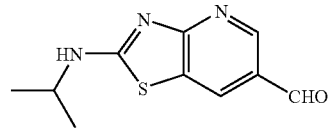

A mixture of the above-obtained (2-(isopropylamino)thiazolo[4,5-b]pyridin-6-yl)methanol (≦1.05 mmol) and manganese(IV) oxide (activated, 85%, 1.25 g, 12.2 mmol) in THF (12 mL) was stirred at rt for 3.5 hr. The insoluble material was removed by suction filtration through Celite® 545. The filtrate was concentrated under vacuum and dried over Drierite® under vacuum to give the title compound (0.115 g, 50% yield over two steps) as a pale solid.

4. 6-(4-(2-Fluorophenyl)oxazol-5-yl)-N-isopropylthiazolo[4,5-b]pyridin-2-amine A mixture of 2-(isopropylamino)thiazolo[4,5-b]pyridine-6-carbaldehyde (55.0 mg, 0.248 mmol), tosylmethyl isocyanide (70.6 mg, 0.260 mmol), and K$_2$CO$_3$ (41.3 mg, 0.299 mmol) in EtOH (6 mL) was heated at reflux for 16 hr. It was then concentrated under vacuum. The residue was diluted with AcOEt (70 mL), washed successively with water and brine, and dried over anhydrous MgSO$_4$. The title compound (54.2 mg, 65% yield) was isolated as a white solid by flash chromatography (60% AcOEt/hexane); 94% purity by LCMS, (M+H)$^+$=337.42.

Example 10

6-(4-(2-fluorophenyl)oxazol-5-yl)-N-isopropylthiazolo[4,5-c]pyridin-2-amine

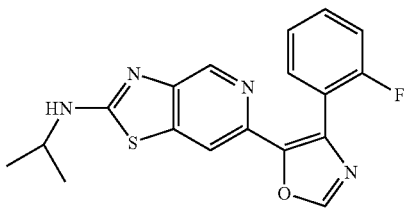

1. 6-chloro-N-isopropylthiazolo[4,5-c]pyridin-2-amine

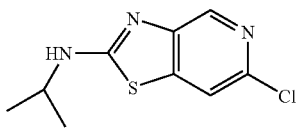

To a solution of 4,6-dichloropyridin-3-amine (0.50 g, 3.07 mmol, 1.0 eq.) and isopropyl isothiocyanate (0.33 mL, 3.10 mmol, 1.0 eq.) in DMF under nitrogen at 0° C. was added NaH (60% in mineral oil, 0.194 g, 4.85 mmol, 1.6 eq.). After 10 min., the cold bath was removed, and the reaction mixture was stirred to room temperature for 10 min. It was then heated at 65° C. for 1 hr and cooled to room temperature. At 0° C., aqueous HCl (1 N), water and EtOAc were added, and the reaction mixture was stirred. The layers were separated, and the organic layer was washed with saturated aqueous NaHCO$_3$ and brine, dried over Na$_2$SO$_4$, filtered and concentrated in vacuo. Silica gel chromatography using CH$_2$Cl$_2$:MeOH (100:1) as eluent afforded 6-chloro-N-isopropylthiazolo[4,5-c]pyridin-2-amine as a white solid (0.43 g, 61% yield).

2. Methyl 2-(isopropylamino)thiazolo[4,5-c]pyridine-6-carboxylate

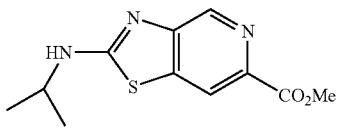

A solution of 6-chloro-N-isopropylthiazolo[4,5-c]pyridin-2-amine (0.24 g, 1.05 mmol, 1.0 eq.), Pd(OAc)$_2$ (0.0313 g, 0.139 mmol, 0.1 eq.), 1,3-bis(diphenylphosphino)propane (0.0443 g, 0.107 mmol, 0.1 eq.) and K$_2$CO$_3$ (0.2214 g, 1.60 mmol, 1.5 eq.) in MeOH (2.6 mL) and DMF (1.3 mL) was stirred under an atmosphere of CO inside a bomb (40 psi) at 91° C. overnight. After cooling to room temperature, the reaction mixture was filtered through Celite and rinsed with MeOH. The filtrate was concentrated in vacuo, diluted with EtOAc and water. The layers were separated, and the organic layer was washed with brine and 10% aqueous LiCl, dried over Na$_2$SO4, filtered and concentrated in vacuo. The residue was triturated with CH$_2$Cl$_2$:MeOH (10:0.3) to give methyl 2-(isopropylamino)thiazolo[4,5-c]pyridine-6-carboxylate as a white solid (0.081 g, 31% yield).

3. (2-(isopropylamino)thiazolo[4,5-c]pyridin-6-yl)methanol

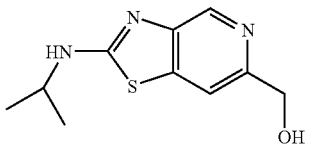

To a solution of methyl 2-(isopropylamino)thiazolo[4,5-c]pyridine-6-carboxylate (0.1286 g, 0.51 mmol, 1.0 eq.) in THF (1.3 mL) under nitrogen at 0° C. was added LAH (1M, THF; 0.8 mL, 0.8 mmol, 1.6 eq.). After 1.25 h, ice and EtOAc were added, the cold bath was removed, and the solution was stirred to room temperature. The layers were separated, and the organic layer was washed with brine, dried over Na$_2$SO$_4$, filtered, and concentrated in vacuo to give (2-(isopropylamino)thiazolo[4,5-c]pyridin-6-yl)methanol as a light yellow solid (0.1063 g, 93% yield).

4. 2-(isopropylamino)thiazolo[4,5-c]pyridine-6-carbaldehyde

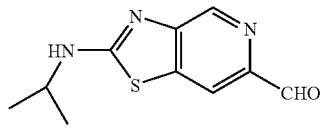

To a solution of (2-(isopropylamino)thiazolo[4,5-c]pyridin-6-yl)methanol (0.1063 g, 0.476 mmol, 1.0 eq.) in THF (5 mL) under nitrogen was added MnO$_2$ (0.6441 g, 7.4 mmol, 15.6 eq.). After 1.75 hr, the reaction solution was filtered through Celite and rinsed with THF. The filtrate was concentrated in vacuo to give crude 2-(isopropylamino)thiazolo[4,5-c]pyridine-6-carbaldehyde as a yellow solid (0.1711 g). This material was used without further purification.

5. 6-(4-(2-fluorophenyl)oxazol-5-yl)-N-isopropylthiazolo[4,5-c]pyridin-2-amine A solution of 2-(isopropylamino)thiazolo[4,5-c]pyridine-6-carbaldehyde (presumed 0.234 mmol, 1.0 eq.), 1-fluoro-2-(isocyano(tosyl)methyl)benzene (0.079 g, 0.273 mmol, 1.2 eq.), and K$_2$CO$_3$ (0.0654 g, 0.473 mmol, 2.0 eq.) in EtOH (2.4 mL) was refluxed for 4.75 hr. After cooling to room temperature, the reaction mixture was concentrated in vacuo, and the residue was taken up in EtOAc and water. After separation of the layers, the organic layer was washed with saturated aqueous NaHCO$_3$ and brine, dried over Na$_2$SO$_4$, filtered, and concentrated in vacuo. MeOH was added to the residue, and the mixture was subjected to autoprep. The appropriate fractions were collected, and NaHCO$_3$ (s) was added. The solution was then concentrated in vacuo not to dryness and extracted with EtOAc (3×). The organic layers were combined, dried over Na$_2$SO$_4$, filtered, and concentrated in vacuo to give 6-(4-(2-fluorophenyl)oxazol-5-yl)-N-isopropylthiazolo[4,5-c]pyridin-2-amine as a light yellow solid (0.0243 g, 29% yield). LC/MS (MH)=355.16.

Example 11

6-(4-(2-fluorophenyl)-1H-imidazol-5-yl)-N-isopropylthiazolo[4,5-c]pyridin-2-amine

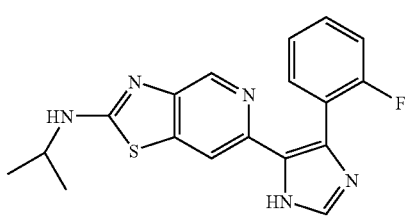

A solution of 2-(isopropylamino)thiazolo[4,5-c]pyridine-6-carbaldehyde (example 10, step 4) (presumed 0.244 mmol, 1.0 eq.) and concentrated aqueous NH$_4$OH (0.050 mL) in THF (1 mL) was stirred overnight. 1-Fluoro-2-(isocyano(tosyl)methyl)benzene (0.0880 g, 0.304 mmol, 1.2 eq.) and piperazine (0.0371 g, 0.431 mmol, 1.8 eq.) were added, and the reaction mixture was stirred overnight. It was then diluted with EtOAc and washed with water, saturated aqueous NaHCO₃, and brine, dried over Na₂SO₄, filtered, and concentrated in vacuo. MeOH was added to the residue, and the mixture was subjected to autoprep. The appropriate fractions were collected, and NaHCO₃ (s) was added. The solution was then concentrated in vacuo not to dryness and extracted with EtOAc (3×). The organic layers were combined, dried over Na₂SO₄, filtered, and concentrated in vacuo to give 6-(4-(2-fluorophenyl)-1H-imidazol-5-yl)-N-isopropylthiazolo[4,5-c]pyridin-2-amine as a light orange solid (0.0212 g, 25% yield). LC/MS (MH)=354.18.

Example 12

5-(3-(2-fluorophenyl)-1H-pyrazol-4-yl)-N-isopropylthiazolo[5,4-b]pyridin-2-amine

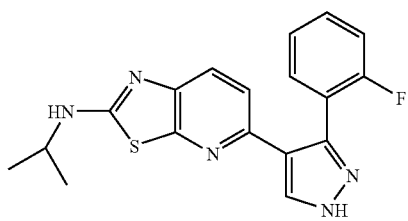

1. 5-chloro-N-isopropylthiazolo[5,4-b]pyridin-2-amine

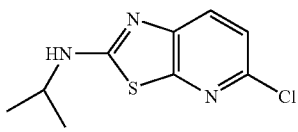

To a solution of 2,6-dichloropyridin-3-amine (3.71 g, 22.8 mmol, 1.0 eq.) and isopropyl isothiocyanate (2.5 mL, 23.5 mmol, 1.0 eq.) in DMF (57 mL) under nitrogen at 0° C. was added NaH (95% in mineral oil, 0.77 g, 30.5 mmol, 1.3 eq.). After 10 min., the cold bath was removed, and the reaction mixture was stirred to room temperature for 10 min. It was then heated at 68° C. overnight. After cooling to 0° C., isopropyl isothiocyanate (1.5 mL) and NaH (0.44 g) were added, and heating was resumed. After 7.25 h, the reaction was cooled to room temperature. At 0° C., aqueous HCl (1 N), water and EtOAc were added, and the reaction mixture was stirred. The layers were separated, and the organic layer was washed with saturated aqueous NaHCO₃ and brine, dried over Na₂SO₄, filtered and concentrated in vacuo. Trituration with Et₂O afforded 5-chloro-N-isopropylthiazolo[5,4-b]pyridin-2-amine as a white solid (3.43 g, 66% yield).

2. Methyl 2-(isopropylamino)thiazolo[5,4-b]pyridine-5-carboxylate

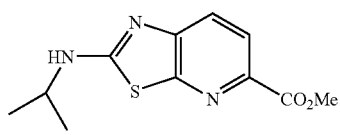

A solution of 5-chloro-N-isopropylthiazolo[5,4-b]pyridin-2-amine (2.06 g, 9.05 mmol, 1.0 eq.), Pd(OAc)₂ (0.2084 g, 0.928 mmol, 0.1 eq.), 1,3-bis(diphenylphosphino)propane (0.3775 g, 0.915 mmol, 0.1 eq.) and K₂CO₃ (1.90 g, 13.7 mmol, 1.5 eq.) in MeOH (24 mL) and DMF (12 mL) was stirred under an atmosphere of CO inside a bomb (42 psi) at 92° C. overnight. After cooling to room temperature, the reaction mixture was filtered through Celite and rinsed with MeOH. The filtrate was concentrated in vacuo, diluted with EtOAc and water. The layers were separated, and the organic layer was washed with brine and 10% aqueous LiCl, dried over Na₂SO₄, filtered and concentrated in vacuo. Silica gel chromatography using CH₂Cl₂:MeOH (10:0.1) as eluent afforded methyl 2-(isopropylamino)thiazolo[5,4-b]pyridine-5-carboxylate as a white solid (1.67 g, 74% yield).

3. (2-(isopropylamino)thiazolo[5,4-b]pyridin-5-yl)methanol

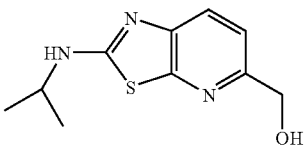

To a solution of methyl 2-(isopropylamino)thiazolo[5,4-b]pyridine-5-carboxylate (1.67 g, 6.64 mmol, 1.0 eq.) in THF (17 mL) under nitrogen at 0° C. was added LAH (1M, THF; 10 mL, 10 mmol, 1.5 eq.). After 2.25 hr, ice and EtOAc were added, the cold bath was removed, and the solution was stirred to room temperature. The layers were separated, and the organic layer was washed with brine, dried over Na₂SO₄, filtered, and concentrated in vacuo. Silica gel chromatography using CH₂Cl₂:MeOH (10:0.4) as eluent afforded (2-(isopropylamino)thiazolo[5,4-b]pyridin-5-yl)methanol as a white solid (1.25 g, 84% yield).

4. 5-(chloromethyl)-N-isopropylthiazolo[5,4-b]pyridin-2-amine dihydrochloride

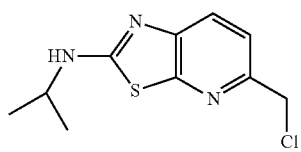

To a solution of (2-(isopropylamino)thiazolo[5,4-b]pyridin-5-yl)methanol (0.71 g, 3.18 mmol, 1.0 eq.) in CH₂Cl₂ (11 mL) under nitrogen at 0° C. was added SOCl₂ (1.0 mL, 13.7 mmol, 4.3 eq.). After 5 min., the cold bath was removed, and the reaction mixture was stirred to room temperature for 10 min. and then refluxed for 2.75 hr. After cooling to room temperature, the reaction mixture was concentrated in vacuo to give 5-(chloromethyl)-N-isopropylthiazolo[5,4-b]pyridin-2-amine dihydrochloride as a white solid (0.90 g, 90% yield).

5. 5-((2-(2-fluorophenyl)-1,3-dithian-2-yl)methyl)-N-isopropylthiazolo[5,4-b]pyridin-2-amine

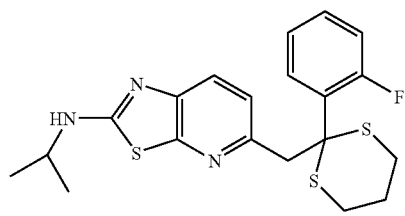

To a solution of 2-(2-fluorophenyl)-1,3-dithiane (2.72 g, 12.7 mmol, 4.4 eq.) in THF (65 mL) under nitrogen at 0° C. was added n-BuLi (1.6M/hexane; 7.4 mL, 11.8 mmol, 4.1 eq.) over 0.5 hr. After another 0.5 hr, the 0° C. bath was removed and replaced by a −78° C. bath. 5-(Chloromethyl)-N-isopropylthiazolo[5,4-b]pyridin-2-amine dihydrochloride (0.90 g, 2.86 mmol, 1.0 eq.) was added in portions after 15 min., and the reaction was stirred for 1.5 hr. Ice, EtOAc and saturated aqueous NaHCO$_3$ were added, and the −78° C. bath was removed. After stirring to room temperature, the layers were separated, and the organic layer was dried over Na$_2$SO$_4$, filtered, and concentrated in vacuo. Silica gel chromatography using CH$_2$Cl$_2$ followed by CH$_2$Cl$_2$:MeOH (40:1) as eluent afforded 5-((2-(2-fluorophenyl)-1,3-dithian-2-yl)methyl)-N-isopropylthiazolo[5,4-b]pyridin-2-amine as a yellow solid (0.95 g, 79% yield).

6. 1-(2-fluorophenyl)-2-(2-(isopropylamino)thiazolo[5,4-b]pyridin-5-yl)ethanone

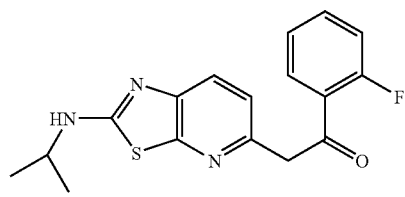

To a solution of 5-((2-(2-fluorophenyl)-1,3-dithian-2-yl)methyl)-N-isopropylthiazolo[5,4-b]pyridin-2-amine (0.61 g, 1.45 mmol, 1.0 eq.) in MeOH (73 mL) and water (6 mL) were added HgO (0.83 g, 3.83 mmol, 2.6 eq.) and HgCl$_2$ (1.83 g, 6.74 mmol, 4.6 eq.). After stirring for 15 min., the solution was refluxed for another 15 min. and cooled to room temperature. The precipitate was removed, and the filtrate was concentrated in vacuo. The residue was diluted with EtOAc and water, and the layers were separated. The organic layer was washed with saturated aqueous NaHCO$_3$ and brine, dried over Na$_2$SO$_4$, filtered and concentrated in vacuo. Acetone (7 mL), water (0.1 mL, 5.56 mmol, 3.8 eq.), and TsOH.H$_2$O (0.0342 g, 0.180 mmol, 0.1 eq.) were added, and the reaction was stirred overnight and concentrated in vacuo. The residue was diluted with CH$_2$Cl$_2$ and water, and the layers were separated. The organic layer was washed with saturated aqueous NaHCO$_3$ and brine, dried over Na$_2$SO$_4$, filtered and concentrated in vacuo. Silica gel chromatography using CH$_2$Cl$_2$:MeOH (15:0.1) as eluent afforded 1-(2-fluorophenyl)-2-(2-(isopropylamino)thiazolo[5,4-b]pyridin-5-yl)ethanone as a yellow solid (0.1994 g, 42% yield).

7. 5-(3-(2-fluorophenyl)-1H-pyrazol-4-yl)-N-isopropylthiazolo[5,4-b]pyridin-2-amine A solution of 1-(2-fluorophenyl)-2-(2-(isopropylamino)thiazolo[5,4-b]pyridin-5-yl)ethanone (0.0403 g, 0.122 mmol, 1.0 eq.) in DMF/DMA (1.0 mL) was heated under nitrogen at 80° C. for 2 hr. After cooling to room temperature, the reaction mixture was concentrated in vacuo and dissolved in EtOH (0.5 mL). Hydrazine (0.1 mL, 3.19 mmol, 26.1 eq.) was added, and the reaction was allowed to stand for 2.75 hr and then concentrated in vacuo. MeOH was added to the residue, and the mixture was subjected to autoprep. The appropriate fractions were collected, and NaHCO$_3$ (s) was added. The solution was then concentrated in vacuo not to dryness and extracted with CH$_2$Cl$_2$ (3×). The organic layers were combined, dried over Na$_2$SO$_4$, filtered, and concentrated in vacuo to give 5-(3-(2-fluorophenyl)-1H-pyrazol-4-yl)-N-isopropylthiazolo[5,4-b]pyridin-2-amine as a light yellow solid (0.0125 g, 29% yield). LC/MS (MH)=354.26.

Example 13

N-sec-butyl-5-(4-(2-fluorophenyl)oxazol-5-yl)thiazolo[5,4-b]pyridin-2-amine

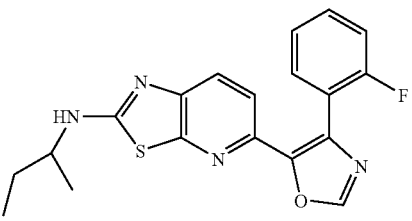

1. 2-(sec-butylamino)thiazolo[5,4-b]pyridine-5-carbaldehyde

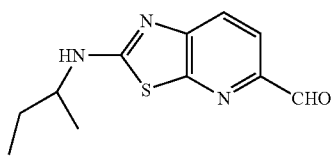

To a solution of (2-(sec-butylamino)thiazolo[5,4-b]pyridin-5-yl)methanol (0.1155 g, 0.487 mmol, 1.0 eq.) in THF (3.5 mL) under nitrogen was added MnO$_2$ (0.6357 g, 7.3 mmol, 15.0 eq.). After 1 hr, the reaction solution was filtered through Celite and rinsed with THF. The filtrate was concentrated in vacuo to give crude 2-(sec-butylamino)thiazolo[5,4-b]pyridine-5-carbaldehyde as a colorless oil which was carried to the next step without purification.

2. N-sec-butyl-5-(4-(2-fluorophenyl)oxazol-5-yl)thiazolo[5,4-b]pyridin-2-amine A solution of 2-(sec-butylamino)thiazolo[5,4-b]pyridine-5-carbaldehyde (presumed 0.24 mmol, 1.0 eq.), 1-fluoro-2-(isocyano(tosyl)methyl)benzene (0.0874 g, 0.302 mmol, 1.3 eq.), and K$_2$CO$_3$ (0.0654 g, 0.473 mmol, 2.0 eq.) in EtOH (2.4 mL) was refluxed overnight. After cooling to room temperature, the reaction mixture was concentrated in vacuo, and the residue was taken up in EtOAc and water. After separation of the layers, the organic layer was washed with saturated aqueous NaHCO$_3$ and brine, dried over Na$_2$SO$_4$, filtered, and concentrated in vacuo. MeOH was added to the residue, and the mixture was subjected to autoprep. The appropriate fractions were collected, and NaHCO$_3$ (s) was added. The solution was then concentrated in vacuo not to dryness and extracted with EtOAc (3×). The organic layers were combined, dried over Na₂SO₄, filtered, and concentrated in vacuo to give N-sec-butyl-5-(4-(2-fluorophenyl)oxazol-5-yl)thiazolo[5,4-b]pyridin-2-amine as a yellow solid (0.0264 g, 30% yield). LC/MS (MH)=369.20.

Example 14

N-sec-butyl-5-(4-(2-fluorophenyl)-1H-imidazol-5-yl)thiazolo[5,4-b]pyridin-2-amine

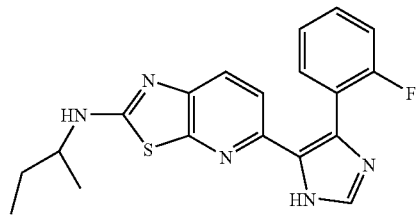

A solution of 2-(sec-butylamino)thiazolo[5,4-b]pyridine-5-carbaldehyde (presumed 0.24 mmol, 1.0 eq.) and concentrated aqueous NH₄OH (0.050 mL) in THF (0.8 mL) was stirred overnight. 1-Fluoro-2-(isocyano(tosyl)methyl)benzene (0.0841 g, 0.291 mmol, 1.2 eq.) and piperazine (0.0394 g, 0.457 mmol, 1.9 eq.) were added, and the reaction mixture was stirred overnight. It was then diluted with EtOAc and washed with water, saturated aqueous NaHCO₃, and brine, dried over Na₂SO4, filtered, and concentrated in vacuo. MeOH was added to the residue, and the mixture was subjected to autoprep. The appropriate fractions were collected, and NaHCO₃ (s) was added. The solution was then concentrated in vacuo not to dryness and extracted with CH₂Cl₂ (3×). The organic layers were combined, dried over Na₂SO₄, filtered, and concentrated in vacuo to give N-sec-butyl-5-(4-(2-fluorophenyl)-1H-imidazol-5-yl)thiazolo[5,4-b]pyridin-2-amine as a yellow solid (0.0228 g, 26% yield). LC/MS (MH)=368.23.

Example 15

5-(5-amino-3-phenyl-1H-pyrazol-4-yl)-N-isopropylthiazolo[5,4-b]pyridin-2-amine

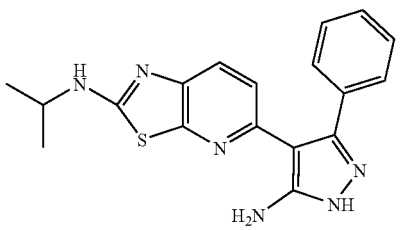

1. 6-chloro-2-(ethylthio)-3-nitropyridine

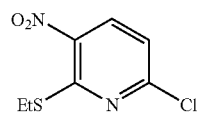

To a solution of 2,6-dichloro-3-nitropyridine (2.24 g, 11.6, 1.0 eq.) and EtSH (0.86 mL, 11.6 mmol, 1.0 eq.) in THF (60 mL) under nitrogen at 0° C. was added NaH (95%; 0.33 g, 13.1 mmol, 1.1 eq.). After 2.25 hr, the solution was concentrated in vacuo. The residue was dissolved in EtOAc and washed with water, saturated aqueous NaHCO₃, water, and brine, dried over Na₂SO₄, filtered and concentrated in vacuo. Silica gel chromatography using hexanes:EtOAc (10:0.05) as eluent afforded 6-chloro-2-(ethylthio)-3-nitropyridine as a yellow solid (1.34 g, 53%).

2. 2-(6-(ethylthio)-5-nitropyridin-2-yl)-3-(2-fluorophenyl)-3-oxopropanenitrile

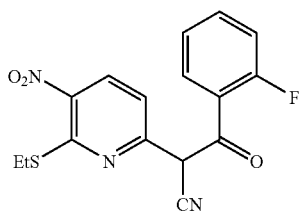

To a solution of 3-(3-fluorophenyl)-3-oxopropanenitrile (1.21 g, 7.42 mmol, 1.2 eq.) in DMF (10 mL) under nitrogen at 0° C. was added NaH (95%; 0.37 g, 14.6 mmol, 2.4 eq.). After 1.25 hr, a solution of 6-chloro-2-(ethylthio)-3-nitropyridine (1.34 g, 6.13 mmol, 1.0 eq.) in DMF (5 mL) was added over 10 min. After 0.5 h, the reaction was heated to 70° C. for 1.5 hr, cooled to room temperature, and concentrated in vacuo. It was diluted with EtOAc and water, and the layers were separated. The aqueous layer was extracted with EtOAc, and the combined organic layers were dried over Na₂SO₄, filtered and concentrated in vacuo. Silica gel chromatography using hexanes:EtOAc (2:1) as eluent afforded 2-(6-(ethylthio)-5-nitropyridin-2-yl)-3-(2-fluorophenyl)-3-oxopropanenitrile as a yellow solid (0.40 g, 19%).

3. 2-(5-amino-6-(ethylthio)pyridin-2-yl)-3-(2-fluorophenyl)-3-oxopropanenitrile

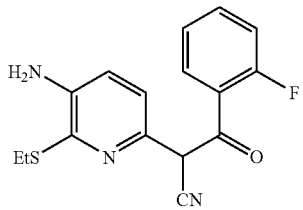

A solution of 2-(6-(ethylthio)-5-nitropyridin-2-yl)-3-(2-fluorophenyl)-3-oxopropanenitrile (0.40 g, 1.16 mmol, 1.0 eq.) and SnCl₂.2H₂O (1.35 g, 5.98 mmol, 5.2 eq.) in EtOAc (30 mL) was refluxed for 0.75 hr and cooled to room temperature. At 0° C., aqueous NaOH (1N, 15 mL) was added. The layers were separated, and the aqueous layer was extracted with EtOAc. The combined organic layers were dried over Na₂SO₄, filtered and concentrated in vacuo. Silica gel chromatography using CH₂Cl₂:MeOH (10:0.2) as eluent afforded 2-(5-amino-6-(ethylthio)pyridin-2-yl)-3-(2-fluorophenyl)-3-oxopropanenitrile as a light brown solid (0.1933 g, 53%).

4. 2-(5-amino-6-(ethylsulfonyl)pyridin-2-yl)-3-(2-fluorophenyl)-3-oxopropanenitrile

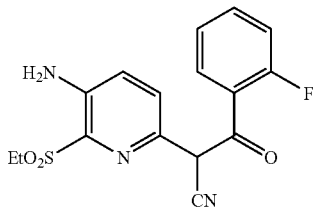

To a solution of 2-(5-amino-6-(ethylthio)pyridin-2-yl)-3-(2-fluorophenyl)-3-oxopropanenitrile (0.30 g, 0.951 mmol, 1.0 eq.) in THF (32 mL) at 0° C. was added MCPBA (0.49 g, 2.84 mmol, 3.0 eq.). After 20 min., the solution was concentrated in vacuo and dissolved in $CH_2Cl_2$. 5% aqueous sodium thiosulfate was added, and the solution was stirred for 5 min. Saturated aqueous $NaHCO_3$ was then added, and the solution was stirred for 5 min. After separation of the layers, the aqueous layer was extracted with $CH_2Cl_2$ (2×). The combined organic layers were dried over $Na_2SO_4$, filtered and concentrated in vacuo to give 2-(5-amino-6-(ethylsulfonyl)pyridin-2-yl)-3-(2-fluorophenyl)-3-oxopropanenitrile as a burgundy solid which was carried to the next step without purification.

5. 3-(2-fluorophenyl)-2-(2-(isopropylamino)thiazolo[5,4-b]pyridin-5-yl)-3-oxopropane-nitrile

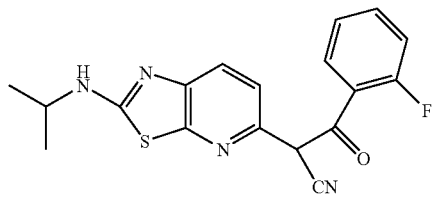

To a solution of 2-(5-amino-6-(ethylsulfonyl)pyridin-2-yl)-3-(2-fluorophenyl)-3-oxopropanenitrile (presumed 0.951 mmol, 1.0 eq.) and iPrNCS (0.15 mL, 1.43 mmol, 1.5 eq.) in DMF (4.8 mL) under nitrogen at 0° C. was added NaH (95%; 0.0982 g, 3.89 mmol, 4.1 eq.). After 0.75 hr, the cold bath was removed and the reaction was stirred to room temperature for 0.5 hr. At 0° C., iPrNCS (0.1 mL) and NaH (0.050 g) were added and stirred for 0.25 hr. The cold bath was removed, and the reaction was stirred to room temperature overnight. At 0° C., water and EtOAc were added, and separated. The aqueous layer was washed with EtOAc (2×). The aqueous layer was concentrated in vacuo. Silica gel chromatography using $CH_2Cl_2$:MeOH (100:1) as eluent afforded 3-(2-fluorophenyl)-2-(2-(isopropylamino)thiazolo[5,4-b]pyridin-5-yl)-3-oxopropanenitrile as a burgundy solid (0.10 g, 29%).

6. 5-(5-amino-3-phenyl-1H-pyrazol-4-yl)-N-isopropylthiazolo[5,4-b]pyridin-2-amine To a solution of 3-(2-fluorophenyl)-2-(2-(isopropylamino)thiazolo[5,4-b]pyridin-5-yl)-3-oxopropanenitrile (0.10 g, 0.282 mmol, 1.0 eq.) in EtOH (1 mL) and HOAc (2 mL) at 0° C. was added hydrazine (0.1 mL, 3.19 mmol, 11.3 eq.). After 10 min., the cold bath was removed, and the reaction mixture was stirred to room temperature for 10 min. It was then heated at 88° C. for 5 hr and at 100° C. overnight. After cooling to room temperature and then to 0° C., water was added followed by concentrated aqueous $NH_4OH$ until pH was 10 by litmus paper. The aqueous layer was extracted with EtOAc (3×). The organic layers were combined, dried over $Na_2SO_4$, filtered, and concentrated in vacuo. MeOH was added to the residue, and the mixture was subjected to autoprep. The appropriate fractions were collected, and $NaHCO_3$ (s) was added. The solution was then concentrated in vacuo not to dryness and extracted with $CH_2Cl_2$ (3×). The organic layers were combined, dried over $Na_2SO_4$, filtered, and concentrated in vacuo to give 5-(5-amino-3-phenyl-1H-pyrazol-4-yl)-N-isopropylthiazolo[5,4-b]pyridin-2-amine as a light yellow solid (0.0014 g, 1.3% yield). LC/MS (MH)=369.14.

Example 16

5-(3-(2-Fluorophenyl)-1-methyl-1H-pyrazol-4-yl)-N-propylthiazolo[5,4-b] pyridin-2-amine

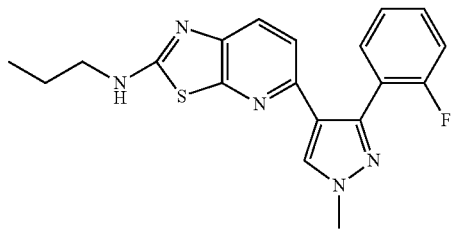

1. (Z)-3-(dimethylamino)-1-(3-fluorophenyl)prop-2-en-1-one

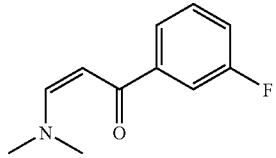

A solution of 1-(3-fluorophenyl)ethanone (21.38 g, 154.8 mmol, 1.0 eq.) in DMF/DMA (150 mL) was heated under nitrogen at 95° C. overnight. After cooling to room temperature, the reaction mixture was concentrated in vacuo to give (Z)-3-(dimethylamino)-1-(3-fluorophenyl)prop-2-en-1-one as a red oil (30.70 g, 100% yield).

2. 3-(2-fluorophenyl)-1H-pyrazole

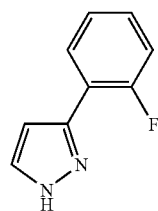

To a solution of (Z)-3-(dimethylamino)-1-(3-fluorophenyl)prop-2-en-1-one (10.30 g, 53.3 mmol, 1.0 eq.) in ethanol (180 mL) under nitrogen at 0 °C. was added hydrazine (10.0 mL, 318.6 mmol, 6.0 eq.). After 10 min, the cold bath was removed, and the reaction mixture was stirred to room temperature overnight. It was then concentrated in vacuo to give 3-(2-fluorophenyl)-1H-pyrazole as an oil (8.62 g, 100% yield).

3. 3-(2-fluorophenyl)-1-methyl-1H-pyrazole and 5-(2-fluorophenyl)-1-methyl-1H-pyrazole

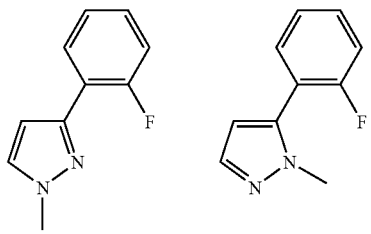

To a solution of 3-(2-fluorophenyl)-1H-pyrazole (8.62 g, 53.2 mmol, 1.0 eq.) in methanol (133 mL) under nitrogen at 0° C. were added iodomethane (4.3 mL, 68.9 mmol, 1.3 eq.), NaOH (aq., 6 N, 34 mL, 204.0 mmol, 3.8 eq.) and nBu$_4$NBr (0.68 g, 2.11 mmol, 0.04 eq.). The cold bath was then removed, and the reaction mixture was stirred to room temperature. After 6.5 h, iodomethane was added (4 mL), and the reaction mixture was stirred overnight. More iodomethane (4 mL) and NaOH (aq., 6 N, 20 mL) were added, and the reaction mixture was stirred overnight. It was then concentrated in vacuo not to dryness, diluted with EtOAc, and the two layers were separated. The aqueous layer was extracted with EtOAc, and the organic layers were combined, dried over Na$_2$SO$_4$, filtered, and concentrated in vacuo. Silica gel chromatography using hexanes:EtOAc (15:2) as eluent afforded a mixture of 3-(2-fluorophenyl)-1-methyl-1H-pyrazole and 5-(2-fluorophenyl)-1-methyl-1H-pyrazole (6.78 g, 72% yield).

4. 4-bromo-3-(2-fluorophenyl)-1-methyl-1H-pyrazole

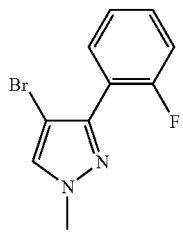

To a solution of a mixture of 3-(2-fluorophenyl)-1-methyl-1H-pyrazole and 5-(2-fluorophenyl)-1-methyl-1H-pyrazole (6.77 g, 38.4 mmol, 1.0 eq.) in chloroform (10 mL) under nitrogen at 0° C. was added a solution of bromine (2.0 mL, 39.0 mmol, 1.0 eq.) in chloroform (5 mL) over 10 min. After 50 min, the reaction mixture was diluted with chloroform and washed with saturated aqueous NaHCO$_3$ (3×), dried over Na$_2$SO$_4$, filtered, and concentrated in vacuo. Silica gel chromatography using hexanes:EtOAc (10:1) as eluent afforded 4-bromo-5-(2-fluorophenyl)-1-methyl-1H-pyrazole as a white solid (2.70 g, 28% yield), a mixture (0.65 g, 7% yield) and 4-bromo-3-(2-fluorophenyl)-1-methyl-1H-pyrazole as a white solid (5.94 g, 61% yield).

5. 3-(2-fluorophenyl)-1-methyl-4-(4,4,5,5-tetramethyl-1,3,2-dioxaborolan-2-yl)-1H-pyrazole

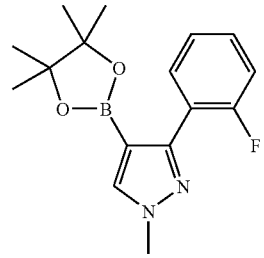

To a solution of 4-bromo-3-(2-fluorophenyl)-1-methyl-1H-pyrazole (3.03 g, 11.9 mmol, 1.0 eq.) in THF (40 mL) under nitrogen at −78° C. was added nBuLi (hexane, 2.5 M, 5.3 mL, 13.2 mmol, 1.1 eq.) over 10 min. After 45 min, 2-isopropoxy-4,4,5,5-tetramethyl-1,3,2-dioxaborolane (2.7 mL, 13.2 mmol, 1.1 eq.) was added. After 1 h 45 min, saturated aqueous NH$_4$Cl and EtOAc were added. The cold bath was removed, and the reaction mixture was stirred to room temperature. The layers were separated, and the organic layer was washed with brine, dried over Na$_2$SO$_4$, filtered, and concentrated in vacuo. Silica gel chromatography using hexanes:EtOAc (3:1) as eluent afforded 3-(2-fluorophenyl)-1-methyl-4-(4,4,5,5-tetramethyl-1,3,2-dioxaborolan-2-yl)-1H-pyrazole as a white solid (1.83 g, 51% yield).

6. 2-(Ethylthio)-6-(3-(2-fluorophenyl)-1-methyl-1H-pyrazol-4-yl)-3-nitropyridine

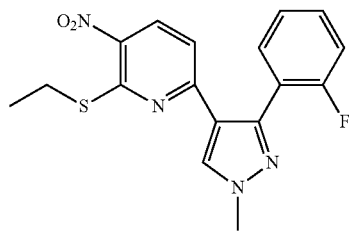

A solution of (5-chloro-2 nitropyridyl)(ethyl)sulfane (0.1267 g, 0.579 mmol, 1.00 eq.) and 3-(2-fluorophenyl)-1-methyl-4-(4,4,5,5-tetramethyl-1,3,2-dioxaborolan -2-yl)-1H-pyrazole (0.2148 g, 0.711 mmol, 1.2 eq.) in toluene (3.3 mL) was purged with nitrogen for 15 min. Pd(Ph$_3$P)$_4$ (0.0365 g, 0.0316 mmol, 0.05 eq.), K$_3$PO$_4$ (aqueous, 2 M, 0.58 mL, 1.16 mmol, 2.0 eq.) and EtOH (0.42 mL) were added, and the reaction mixture was refluxed overnight. After cooling to room temperature, it was diluted with EtOAc and water. The layers were separated, and the organic layer was washed with brine, dried over Na$_2$SO$_4$, filtered, and concentrated in vacuo. Silica gel chromatography using hexanes:EtOAc (2:1) as eluent afforded 2-(ethylthio)-6-(3-(2-fluorophenyl)-1-methyl-1H-pyrazol-4-yl)-3-nitropyridine as a yellow solid (0.1421 g, 68% yield).

7. 2-(Ethylthio)-6-(3-(2-fluorophenyl)-1-methyl-1H-pyrazol-4-yl)pyridine-3-amine

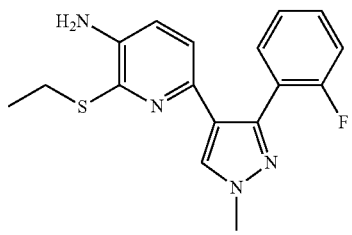

A solution of 2-(ethylthio)-6-(3-(2-fluorophenyl)-1-methyl-1H-pyrazol-4-yl)-3-nitropyridine (2.87 g, 8.01 mmol, 1.00 eq.) and $SnCl_2 \cdot 2H_2O$ (9.05 g, 40.1 mmol, 5.0 eq.) in EtOAc (200 mL) was refluxed for 2 h. After cooling to room temperature, the solution was washed with saturated aqueous $NaHCO_3$, dried over $Na_2SO_4$, filtered, and concentrated in vacuo to give 2-(ethylthio)-6-(3-(2-fluorophenyl)-1-methyl-1H-pyrazol-4-yl)pyridine-3-amine as a yellow solid (2.31 g, 88% yield).

8. 2-(Ethylsulfonyl)-6-(3-(2-fluorophenyl)-1-methyl-1H-pyrazol-4-yl)pyridine-3-amine

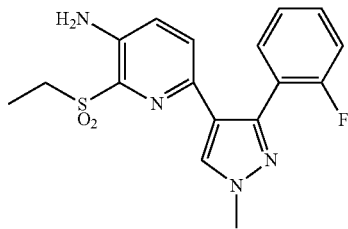

To a solution of 2-(ethylthio)-6-(3-(2-fluorophenyl)-1-methyl-1H-pyrazol-4-yl)pyridine-3-amine (1.00 g, 3.04 mmol, 1.0 eq.) in THF (100 mL) under nitrogen at 0° C. was added MCPBA (77%, 1.60 g, 9.27 mmol, 3.05 eq.). After 3 h 15 min, 5% aqueous sodium thiosulfate and saturated aqueous $NaHCO_3$ were added, and the solution was stirred for 10 min. $CH_2Cl_2$ was then added, and the layers were separated. The aqueous layer was extracted with $CH_2Cl_2$ (2×), and the organic layers were combined, dried over $Na_2SO_4$, filtered, and concentrated in vacuo. Trituration with EtOAc afforded 2-ethylsulfonyl)-6(3-(2-fluorophenyl)-1-methyl-1H-pyrazol-4-yl)pyridine-3-amine as a light tan solid (0.94 g, 85% yield).

9. N-(5-(3-(2-Fluorophenyl)-1-methyl-1H-pyrazol-4-yl)thiazolo[5,4-b]pyridine-2-yl)benzamide

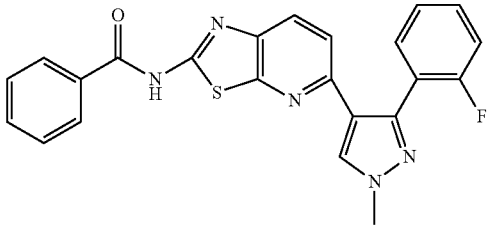

To a solution of 2-(ethylsulfonyl)-6(3-(2-fluorophenyl)-1-methyl-1H-pyrazol-4-yl) pyridine-3-amine (1.04 g, 2.89 mmol, 1.0 eq.) in THF under nitrogen at 0° C. was added benzoyl isothiocyanate (0.47 mL, 3.50 mmol, 1.2 eq.). The cold bath was removed, and the reaction mixture was stirred to room temperature for 20 min. It was then heated to 70° C. for 6 h. After cooling to room temperature, it was diluted with EtOAc and water. The layers were separated, and the organi layer was washed with brine, dried over $Na_2SO_4$, filtered, and concentrated in vacuo. Trituration with EtOAc afforded N-(5-(3-(2-fluorophenyl)-1-methyl-1H-pyrazol-4-yl)thiazolo[5,4-b]pyridine-2-yl)benzamide as a light tan solid (1.05 g, 85% yield).

10. 5-(3-(2-Fluorophenyl)-1-methyl-1H-pyrazol-4-yl)thiazolo[5,4-b]pyridine-2-amine

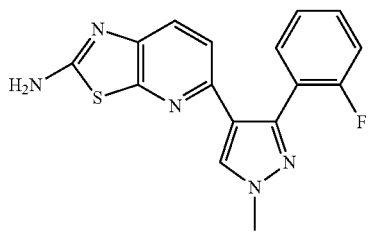

A solution of N-(5-(3-(2-fluorophenyl)-1-methyl-1H-pyrazol-4-yl)thiazolo[5,4-b]pyridine-2-yl)benzamide (0.36 g, 0.838 mmol, 1.0 eq.) in 70% aqueous $H_2SO_4$ (4.2 mL) was heated at 105° C. for 2 h. After cooling to room temperature, the reaction mixture was added to water. At 0° C., 30% aqueous NaOH followed by solid NaOH were added until pH ~13 by litmus paper. The precipitate was washed with water and dried to give 5-(3-(2-fluorophenyl)-1-methyl-1H-pyrazol-4-yl)thiazolo[5,4-b]pyridine-2-amine as a tan solid (0.1493 g, 55% yield).

11. 2-Bromo-5-(3-(2-fluorophenyl)-1-methyl-1H-pyrazol-4-yl)thiazolo[5,4-b]pyridine

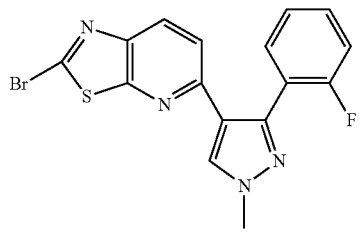

A solution of $CuBr_2$ (0.3251 g, 1.46 mmol, 1.3 eq.) in acetonitrile (8 mL) was purged with N2 for 20 min. At 0° C., t-butyl nitrite (0.21 mL, 1.77 mmol, 1.5 eq.) and 5-(3-(2-fluorophenyl)-1-methyl-1H-pyrazol-4-yl)thiazolo[5,4-b]pyridine-2-amine (0.2578 g, 1.15 mmol, 1.0 eq.) were added. After 15 min, the cold bath was removed, and the reaction mixture was stirred to room temperature overnight. It was then diluted with $Et_2O$ and water. The layers were separated, and the aqueous layer was extracted with $Et_2O$ (2×). The organic layers were combined, washed with saturated aqueous $NaHCO_3$ and brine, dried over $Na_2SO_4$, filtered, and concentrated in vacuo. Silica gel chromatography using $CH_2Cl_2$ as eluent afforded 2-bromo-5-(3-(2-fluorophenyl)-1-methyl-1H-pyrazol-4-yl)thiazolo[5,4-b]pyridine as a yellow foam (0.1584 g, 35% yield).

12. 5-(3-(2-Fluorophenyl)-1-methyl-1H-pyrazol-4-yl)-N-propylthiazolo[5,4-b]pyridine-2-amine

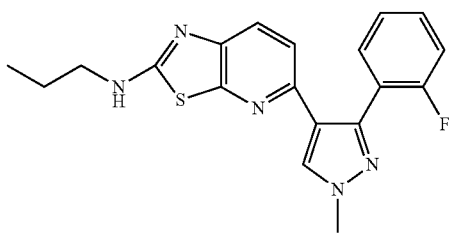

A solution of 2-bromo-5-(3-(2-fluorophenyl)-1-methyl-1H-pyrazol-4-yl)thiazolo[5,4-b]pyridine (0.0294 g, 0.0755 mmol, 1.0 eq.) and n-propylamine (0.1 mL, 1.22 mmol, 16.1 eq.) in 1,4-dioxane (1.5 mL) was heated at 75° C. for 3 h. After cooling to room temperature, the reaction mixture was diluted with $CH_2Cl_2$ and washed with saturated aqueous $NaHCO_3$ and brine, dried over $Na_2SO_4$, filtered, and concentrated in vacuo to afford 5-(3-(2-fluorophenyl)-1-methyl-1H-pyrazol-4-yl)-N-propylthiazolo[5,4-b]pyridine-2-amine as a light tan solid (0.0270 g, 97% yield). LC/MS (MH)= 368.16.

TABLE 1

| Compound | Structure | $(M + H)^+$ |
|---|---|---|
| 17 | 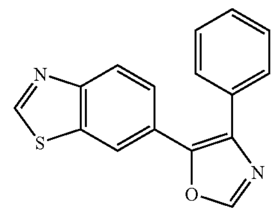 | 279.09 |
| 18 | 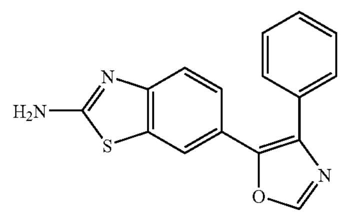 | 293.34 |
| 19 | 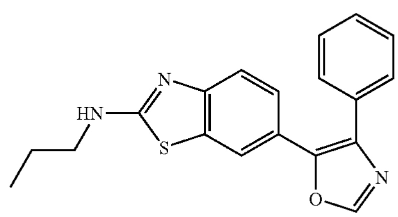 | 336.35 |
| 20 | 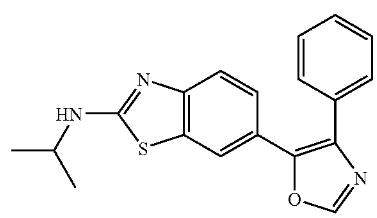 | 336.34 |
| 21 | 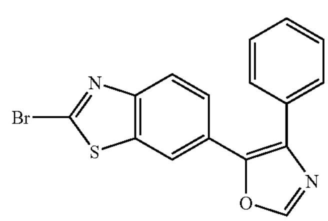 | 375.05 |

TABLE 1-continued
| Compound | Structure | (M + H)+ |
|---|---|---|
| 22 | 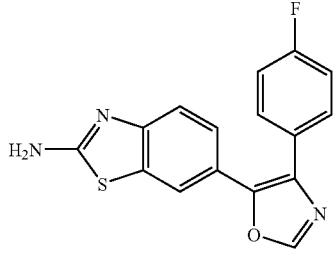 | 312.07 |
| 23 | 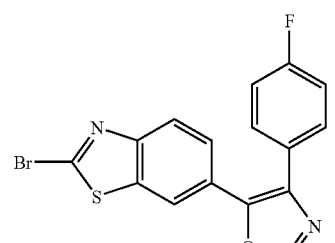 | 375.05 |
| 24 | 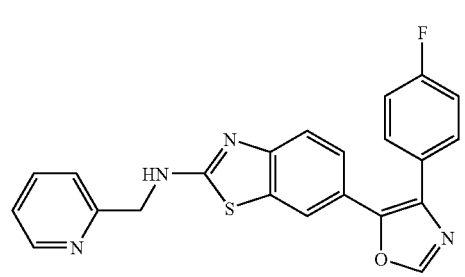 | 403.17 |
| 25 | 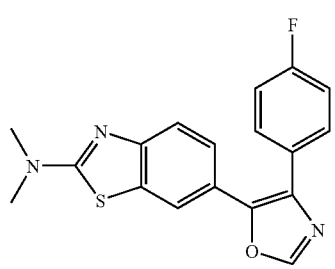 | 340.13 |
| 26 | 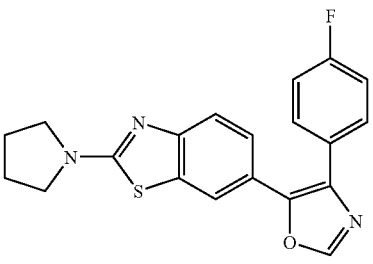 | 366.17 |
| 27 | 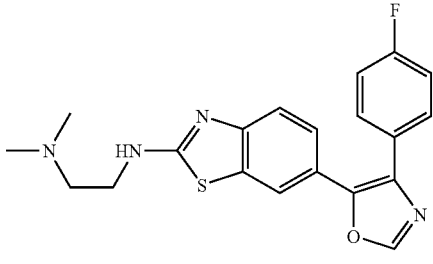 | 383.18 |

TABLE 1-continued
| Compound | Structure | (M + H)+ |
|---|---|---|
| 28 | 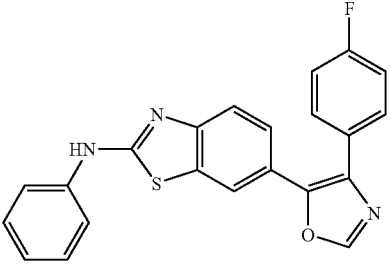 | 388.16 |
| 29 | 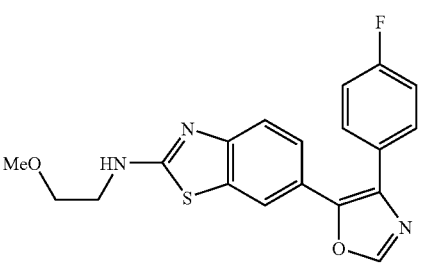 | 370.20 |
| 30 | 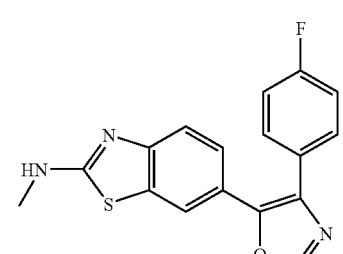 | 326.22 |
| 31 | 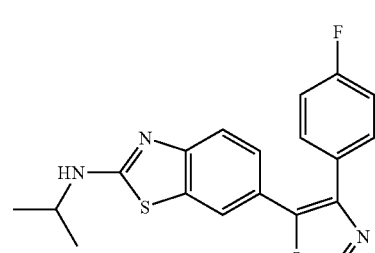 | 354.23 |
| 32 | 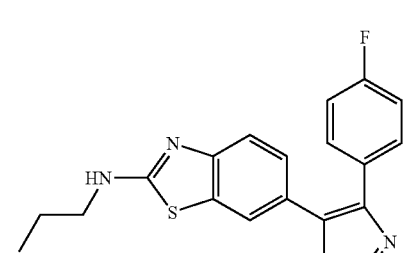 | 354.24 |
| 33 | 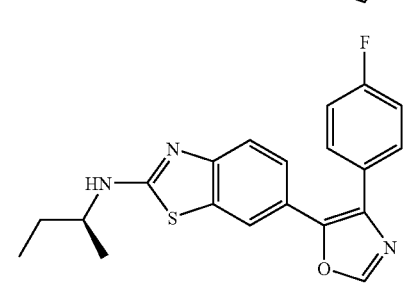 | 368.19 |

TABLE 1-continued

| Compound | Structure | (M + H)+ |
|---|---|---|
| 34 | 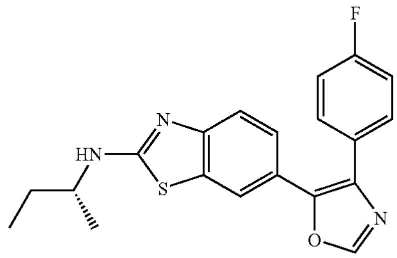 | 368.18 |
| 35 | 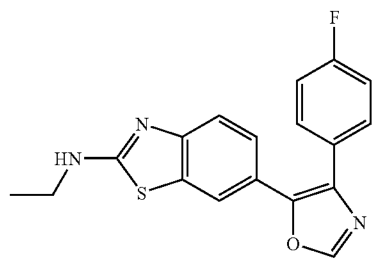 | 340.23 |
| 36 | 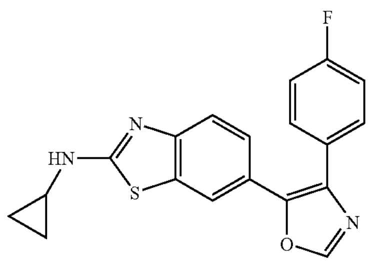 | 352.14 |
| 37 | 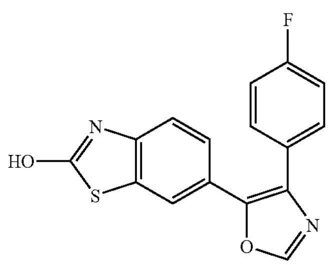 | 313.12 |
| 38 | 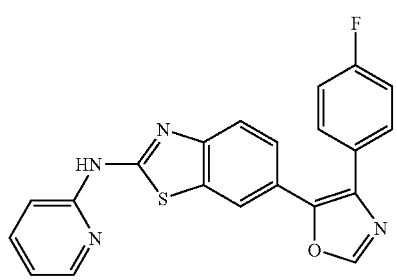 | 389.10 |
| 39 | 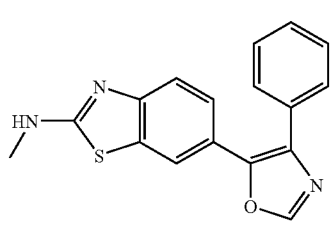 | 308.11 |

TABLE 1-continued

| Compound | Structure | (M + H)+ |
|---|---|---|
| 40 | 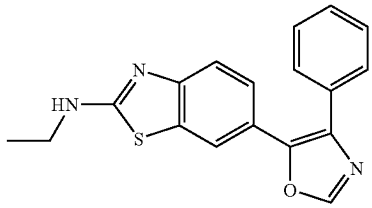 | 322.12 |
| 41 | 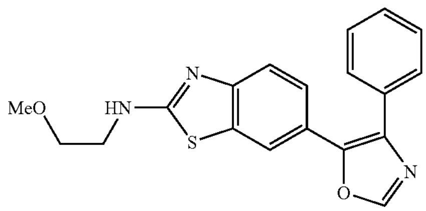 | 352.15 |
| 42 | 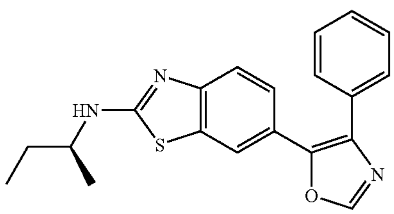 | 350.18 |
| 43 | 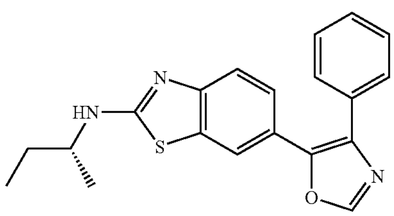 | 350.19 |
| 44 | 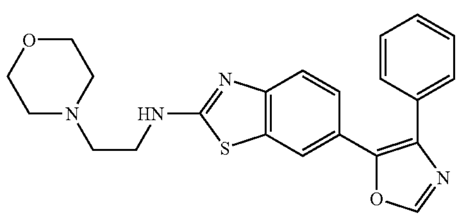 | 407.19 |
| 45 | 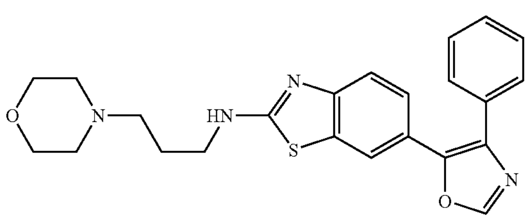 | 421.20 |
| 46 | 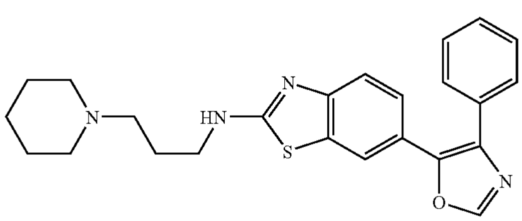 | 419.21 |

TABLE 1-continued

| Compound | Structure | (M + H)+ |
|---|---|---|
| 47 | 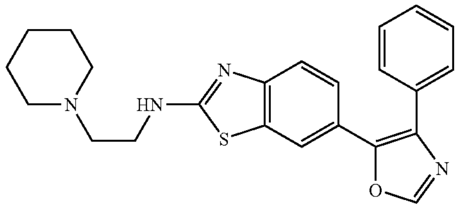 | 405.21 |
| 48 | 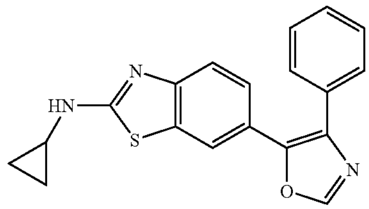 | 334.19 |
| 49 | 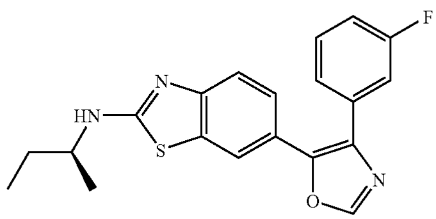 | 368.16 |
| 50 | 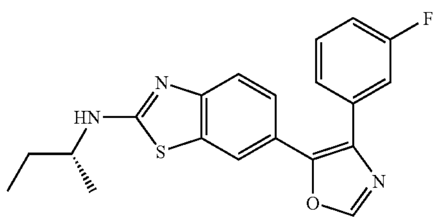 | 368.17 |
| 51 | 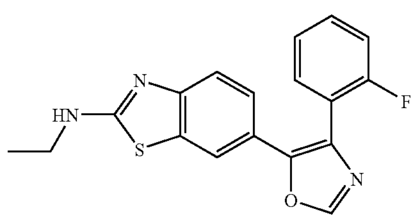 | 340.11 |
| 52 | 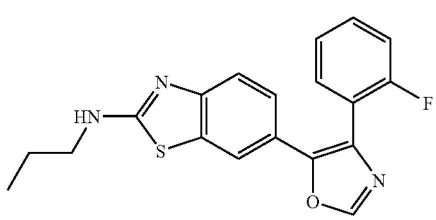 | 354.12 |
| 53 | 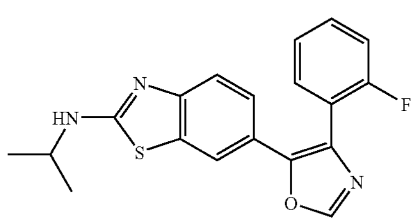 | 354.13 |

TABLE 1-continued
| Compound | Structure | (M + H)+ |
|---|---|---|
| 54 | 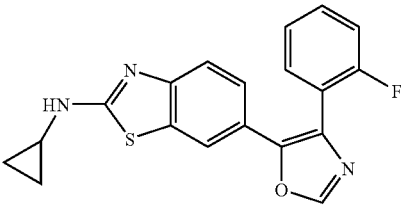 | 352.09 |
| 55 | 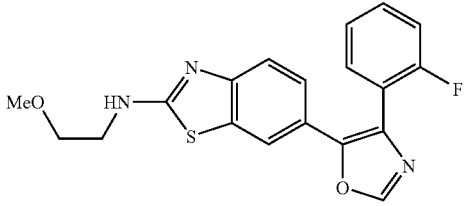 | 370.10 |
| 56 | 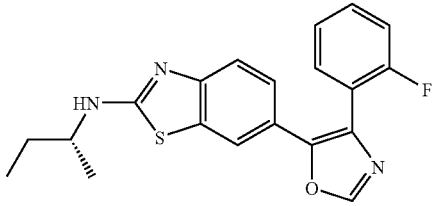 | 368.13 |
| 57 | 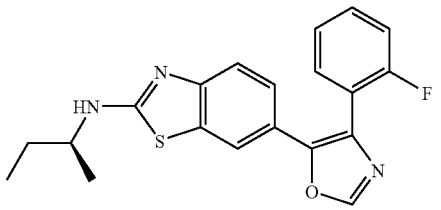 | 368.13 |
| 58 | 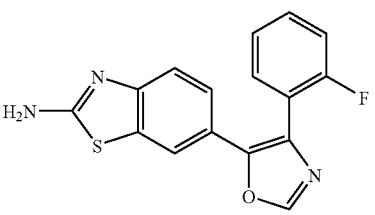 | 312.1 |
| 59 | 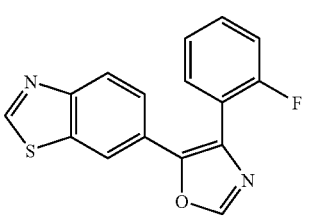 | 297.49 |
| 60 | 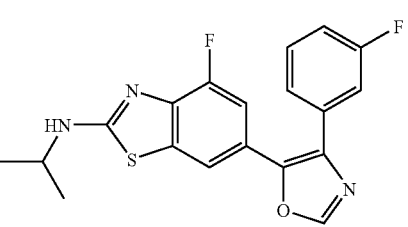 | 354.40 |

TABLE 1-continued

| Compound | Structure | (M + H)+ |
|---|---|---|
| 61 | 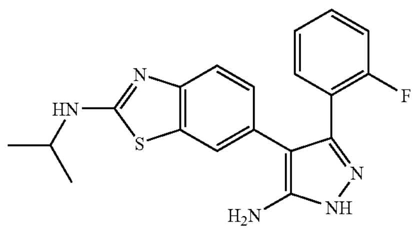 | 368.20 |
| 62 | 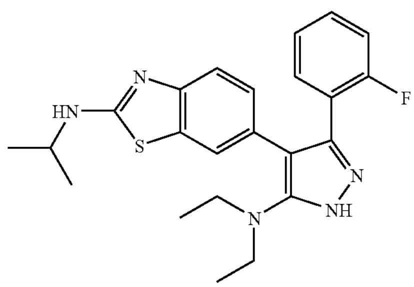 | 424.19 |
| 63 | 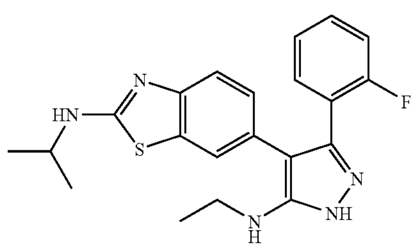 | 396.25 |
| 64 | 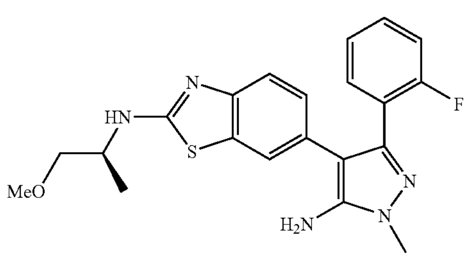 | 412.22 |
| 65 | 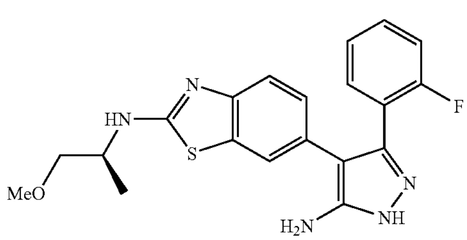 | 397.22 |
| 66 | 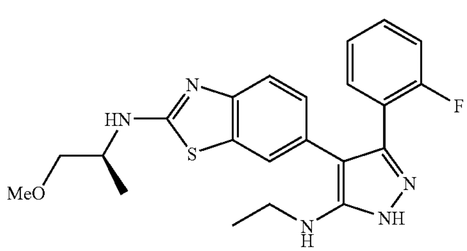 | 426.31 |

TABLE 1-continued

| Compound | Structure | (M + H)+ |
|---|---|---|
| 67 | 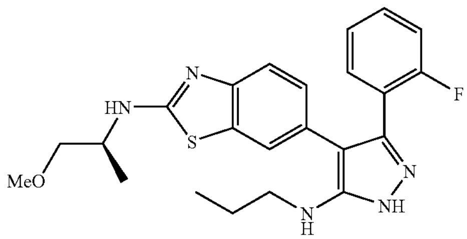 | 440.33 |
| 68 | 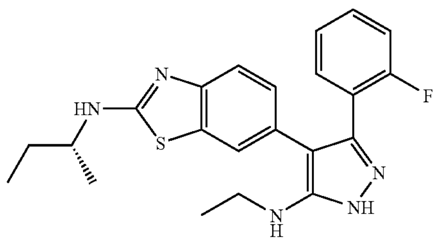 | 410.20 |
| 69 | 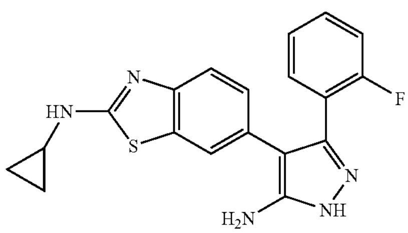 | 366.15 |
| 70 | 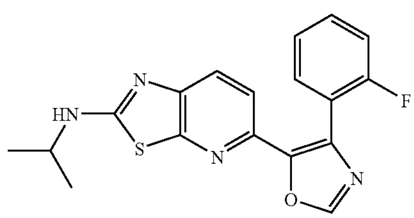 | 355.16 |
| 71 | 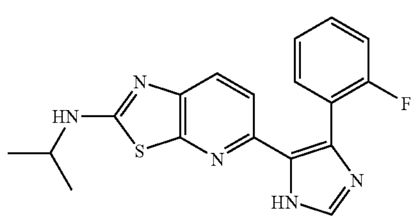 | 354.20 |
| 72 | 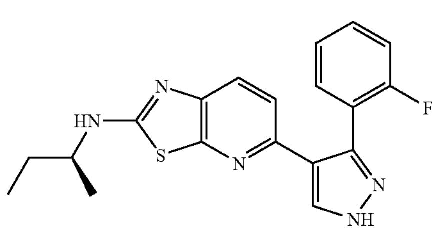 | 368.14 |
| 73 | 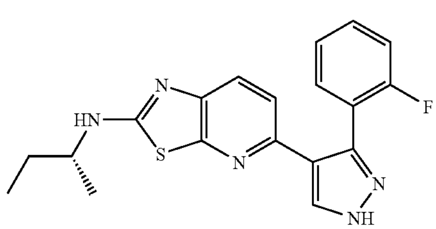 | 368.16 |

TABLE 1-continued

| Compound | Structure | (M + H)+ |
|---|---|---|
| 74 | 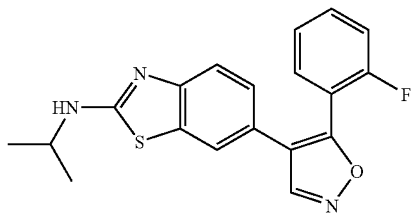 | 355.25 |
| 75 | 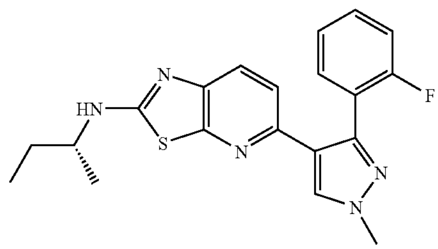 | 382.15 |
| 76 | 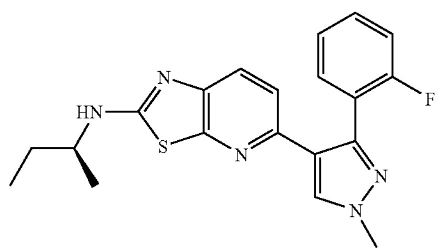 | 382.13 |
| 77 | 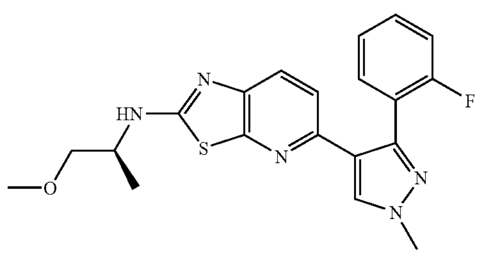 | 398.15 |

What is claimed is:

1. A compound of Formula (I)

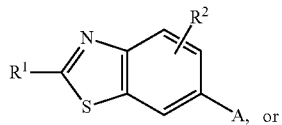

an enantiomer, diastereomer or a pharmaceutically-acceptable salt thereof, wherein:

$R^1$ is hydrogen, hydroxyl, halo, amino, substituted amino, alkyl, substituted alkyl, cycloalkyl, aryl or heterocyclo;

$R^2$ is hydrogen, halo, cyano, $C_1$-$C_4$ alkyl or $C_3$-$C_6$ cycloalkyl; and A is independently selected from:

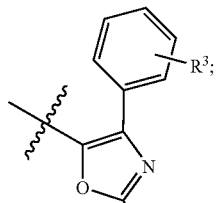 (a)

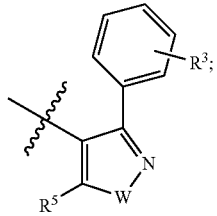 (b)

-continued

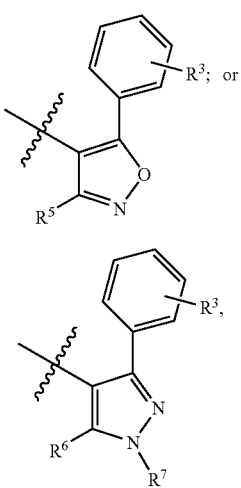

wherein
- R³ is hydrogen, halo, cyano, optionally substituted C₁-C₄ alkyl, optionally substituted C₃-C₆ cycloalkyl, amino or substituted amino;
- R⁴ is hydrogen, amino, substituted amino, alkyl, substituted alkyl, cycloalkyl, cyano, aryl or heterocyclo;
- R⁵ is hydrogen, amino, substituted amino, alkyl, substituted alkyl, cycloalkyl, cyano or heterocyclo;
- R⁶ is amino, substituted amino, hydroxy or alkoxy;
- R⁷ is hydrogen, alkyl, substituted alkyl, cycloalkyl, aryl or heterocyclo; and
- W is O or S.

2. The compound of claim 1 wherein R¹ is —NHCH₃, —NHCH₂CH₃, —NHCH(CH₃)₂, —NH(CH₂)₂CH₃, —NH(CH)₂OCH₃, —NH(CH₂)₂N(CH₃)₂, (R)—NHCH(CH₃)CH₂CH₃, (S)—NHCH(CH₃)CH₂CH₃, (R)—NHCH(CH₃)CH₂CH₂OCH₃, (S)—NHCH(CH₃)CH₂CH₂OCH₃, (R)-tetrahydrofuran-3-ylamino, (S)-tetrahydrofuran-3-ylamino, 4-morpholinoethylamino, 4-morpholinopropylamino, 1-piperidinoethylamino, 1-piperidinopropylamino or cyclopropylamino.

3. The compound of claim 1, wherein A is (a); and R², R³ and R⁴ are each hydrogen.

4. The compound of claim 1, wherein A is (a); R³ is fluoro at the para-position; and R⁴ is hydrogen.

5. The compound of claim 1, wherein A is (a); R³ is fluoro at the meta-position; and R² and R⁴ are each hydrogen.

6. The compound of claim 1, wherein A is (a); R³ is fluoro at the ortho-position; and R² and R⁴ are each hydrogen.

7. The compound of claim 1, wherein A is (a); R² is hydrogen; R³ is fluoro at the ortho-position; and R⁴ is —NH₂.

8. The compound of claim 1, wherein A is (a); R² is fluoro; R³ is fluoro at the ortho-position; and R⁴ is hydrogen.

9. The compound of claim 1, wherein A is (b); W is O; R² is hydrogen; R³ is fluoro at the ortho-position; and R⁵ is —NH₂.

10. The compound of claim 1, wherein A is (d); R² is hydrogen; and R³ is fluoro at the ortho-position.

11. The compound of claim 10, wherein R⁶ is —NH₂, —N(CH₂CH₃)₂, —NHCH₂CH₃, —NH(CH₂)₂CH₃ or —OH.

12. The compound of claim 10, wherein R⁷ is hydrogen, —CH₃, hydroxylethyl or —CH₂CH₃.

13. A pharmaceutical composition comprising at least one compound according to claim 1 and a pharmaceutically-acceptable carrier or diluent.

* * * * *

UNITED STATES PATENT AND TRADEMARK OFFICE
CERTIFICATE OF CORRECTION

| | | |
|---|---|---|
| PATENT NO. | : 7,994,337 B2 | |
| APPLICATION NO. | : 12/333425 | |
| DATED | : August 9, 2011 | |
| INVENTOR(S) | : Chunjian Liu et al. | |

It is certified that error appears in the above-identified patent and that said Letters Patent is hereby corrected as shown below:

In the Specification:

Col. 1, line 8, delete "Jul," and insert -- Jul. --, therefor.

Signed and Sealed this
Twenty-fifth Day of September, 2012

David J. Kappos
*Director of the United States Patent and Trademark Office*